United States Patent
Mershin et al.

(10) Patent No.: US 8,748,111 B2
(45) Date of Patent: Jun. 10, 2014

(54) MULTIPLEXED OLFACTORY RECEPTOR-BASED MICROSURFACE PLASMON POLARITON DETECTOR

(75) Inventors: Andreas Mershin, Cambridge, MA (US); Brian Cook, San Francisco, CA (US); Liselotte Kaiser, Tyreso (SE); Johanna F. Bikker, SE Lexmond (NL); Yoshikatsu Miura, Kyoto (JP); Daisuke Niwa, Osaka (JP); Dai Ohnishi, Ohtsu (JP); Atsushi Tazuke, Kakogawa (JP); Shuguang Zhang, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/015,851

(22) Filed: Jan. 28, 2011

(65) Prior Publication Data

US 2012/0021932 A1    Jan. 26, 2012

Related U.S. Application Data

(63) Continuation of application No. PCT/US2009/052408, filed on Jul. 31, 2009.

(60) Provisional application No. 61/085,298, filed on Jul. 31, 2008.

(51) Int. Cl.

| | |
|---|---|
| *G01N 33/53* | (2006.01) |
| *C07K 2/00* | (2006.01) |
| *B82Y 30/00* | (2011.01) |
| *G01N 33/00* | (2006.01) |
| *G01N 21/55* | (2014.01) |

(52) U.S. Cl.
CPC .............. *G01N 33/0031* (2013.01); *C07K 2/00* (2013.01); *G01N 21/553* (2013.01); *B82Y 30/00* (2013.01)

USPC .................. 435/7.2; 530/300; 422/83; 506/9; 506/35

(58) Field of Classification Search
CPC ........................... G01N 33/5432; G01N 33/53
USPC ............................. 506/9, 35; 422/83; 435/7.2
See application file for complete search history.

(56) References Cited

U.S. PATENT DOCUMENTS 5,606,633 A  *  2/1997  Groger et al. ................... 385/12
7,155,959 B2    1/2007  Su et al.

(Continued)

OTHER PUBLICATIONS

Navratilova et al., Anal. Biochem., 2005, 339:271-281.*

(Continued)

*Primary Examiner* — Christopher M Babic
*Assistant Examiner* — Jeremy C Flinders
(74) *Attorney, Agent, or Firm* — Elmore Patent Law Group, P.C.; Mahreen Chaudhry Hoda; Carolyn S. Elmore

(57) ABSTRACT

The invention provides a bio-sensing nanodevice comprising: a stabilized G-protein coupled receptor on a support, a real time receptor-ligand binding detection method, a test composition delivery system and a test composition recognition program. The G-protein coupled receptor can be stabilized using surfactant peptide. The nanodevice provides a greater surface area for better precision and sensitivity to odorant detection. The invention further provides a microfluidic chip containing a stabilized G-protein coupled receptor immobilized on a support, and arranged in at least two dimensional microarray system. The invention also provides a method of delivering odorant comprising the step of manipulating the bubbles in complex microfluidic networks wherein the bubbles travel in a microfluidic channel carrying a variety of gas samples to a precise location on a chip. The invention further provides method of fabricating hOR17-4 olfactory receptor.

12 Claims, 29 Drawing Sheets

(56) References Cited

U.S. PATENT DOCUMENTS

| | | | |
|---|---|---|---|
| 7,179,784 | B2 | 2/2007 | Zhang et al. |
| 7,295,294 | B2 | 11/2007 | Shimazaki |
| 2003/0008344 | A1 | 1/2003 | Adler et al. |
| 2003/0176335 | A1 | 9/2003 | Zhang et al. |
| 2005/0130197 | A1 | 6/2005 | Do et al. |
| 2005/0176009 | A1 | 8/2005 | Lancet et al. |
| 2006/0003372 | A1 | 1/2006 | Li et al. |
| 2006/0172279 | A1 | 8/2006 | Smela et al. |
| 2006/0188964 | A1 | 8/2006 | Mancia et al. |
| 2006/0280430 | A1 | 12/2006 | Rabinow et al. |
| 2007/0006926 | A1 | 1/2007 | Prakash et al. |
| 2007/0116607 | A1 | 5/2007 | Wang et al. |
| 2007/0157967 | A1 | 7/2007 | Mershin et al. |
| 2007/0286031 | A1 | 12/2007 | Matsumoto |
| 2012/0021932 | A1 | 1/2012 | Mershin et al. |

OTHER PUBLICATIONS

Biacore (Biacore Sensor Surface Handbook, 2003).*
Spehr et al. (Drug News & Perspectives, 2004, 17(3):165, abstract only).*
Prakash et al., Science, 2007, 315:832-835).*
Slavik et al., Biosensors and Actuators B, 1998, 51:311-315.*
Vidic, et al., Quantitive Assessment of Olfactory Receptors Activity in Immobilized Nanosomes: A Novel Concept for Bioelectronic Nose, Lab Chip 6: pp. 1026-1032 (May 2006).
Yeh, et al., Peptergents: Peptide Detergents That Improve Stability and Functionality of a Membrane Protein, Glycerol-3-Phosphate Dehydrogenase, Biochem 44: pp. 16912-16919 (2005).
Zhao, et al., "Designer Short Peptide Surfactants Stabilize G Protein-Coupled Receptor Bovine Rhodospin," PNAS 103(47): pp. 17707-17712 (Nov. 2006).
Hatt, "Molecular and Cellular Basis of Human Olfaction," Chemistry & Biodiversity 1: pp. 1857-1869 (2004).
Maguire, Y., et al., "Ultra-Small-Sample Molecular Structure Detection Using Microsolt Waveguide Nuclear Spin Resonance," PNAS, 104(22): pp. 9198-9203 (2007).
Xu, F., et al., "Simple Approach to Highly Oriented ZnO Nanowire Arrays: Large-Scale Growth, Photoluminescence and Photocatalytic Properties," Nanotechnology, 17: pp. 588-594 (2006).
Vosshall, "Olfaction: Attracting Both Sperm and the Nose," Current Biology 14: pp. R918-R920 (Nov. 2004).
Non-Final Office Action dated Feb. 1, 2011, U.S. Appl. No. 12/183,916.
Final Office Action dated Oct. 6, 2011, U.S. Appl. No. 12/183,916.
Non-Final Office Action dated Jun. 1, 2012, U.S. Appl. No. 12/183,916.
Final Office Action dated Nov. 30, 2012, U.S. Appl. No. 12/183,916.

* cited by examiner

```
     EcoRI    Kozak    Start
CCTGAATTCG CCGCCACCAT GGACGGAGGC AACCAAAGCG AGGGCAGCGA GTTTCTGCTG
CTGGGCATGT CCGAGAGCCC CGAGCAACAG CAGATCCTCT TTTGGATGTT TCTGAGCATG
TATCTGGTCA CCGTGGTCGG AAATGTCCTG ATTATCCTCG CTATTAGCTC CGACAGCAGA
CTCCATACCC CCGTCTACTT CTTTCTGGCT AACCTCTCCT TTACAGACCT GTTTTTCGTC
ACAAACACCA TTCCCAAAAT GCTCGTCAAC CTCCAAAGCC ACAACAAAGC TATTAGCTAT
GCCGGCTGCC TCACACAACT CTATTTTCTC GTGAGCCTGG TGGCCCTGGA TAATCTGATT
CTCGCCGTCA TGGCTTACGA TCGGTACGTG GCTATTTGTT GCCCTCTCCA CTATACAACA
GCTATGAGCC CTAAACTGTG CATCCTGCTC CTGTCCCTGT GCTGGGTGCT CTCCGTGCTG
TATGGACTCA TTCACACACT GCTCATGACA AGAGTGACCT TTTGTGGCTC CAGAAAGATC
CACTACATTT TCTGCGAAAT GTACGTCCTC CTCCGGATGG CCTGTAGCAA CATTCAGATT
AACCATACCG TGCTGATTGC TACCGGATGC TTTATTTTCC TCATCCCCTT CGGATTCGTG
ATCATCAGCT ACGTCCTCAT TATCAGAGCC ATTCTCCGGA TCCCTTCCGT CAGCAAAAAA
TATAAGGCTT TCAGCACCTG TGCCAGCCAT CTGGGAGCCG TCAGCCTGTT TTATGGAACA
CTGTGTATGG TCTATCTCAA ACCTCTCCAC ACCTACAGCG TCAAGGACTC CGTCGCTACA
GTGATGTATG CCGTCGTCAC CCCCATGATG AACCCCTTCA TCTACTCCCT CAGAAACAAA
GATATGCATG GCGCTCTCGG AAGACTCCTG GACAAACACT TTAAAAGACT GACCGGAGGC
ACAGAGACAT CCCAAGTCGC TCCTGCTTAA GCGGCCGCGA
                                Stop  NotI
```

Fig. 19A    SEQ ID NO: 51

```
MDGGNQSEGS EFLLLGMSES PEQQQILFWM FLSMYLVTVV GNVLIILAIS SDSRLHTPVY
FFLANLSFTD LFFVTNTIPK MLVNLQSHNK AISYAGCLTQ LYFLVSLVAL DNLILAVMAY
DRYVAICCPL HYTTAMSPKL CILLLSLCWV LSVLYGLIHT LLMTRVTFCG SRKIHYIFCE
MYVLLRMACS NIQINHTVLI ATGCFIFLIP FGFVIISYVL IIRAILRIPS VSKKYKAFST
CASHLGAVSL FYGTLCMVYL KPLHTYSVKD SVATVMYAVV TPMMNPFIYS LRNKDMHGAL
GRLLDKHFKR LTGGTETSQV APA
               p1D4
```

Fig. 19B    SEQ ID NO: 52

MULTIPLEXED OLFACTORY RECEPTOR-BASED MICROSURFACE PLASMON POLARITON DETECTOR

RELATED APPLICATION

This application is a continuation of International Application No. PCT/US2009/052408, which designated the United States and was filed on Jul. 31, 2009, published in English, and claims the benefit of U.S. Provisional Application No. 61/085,298, filed on Jul. 31, 2008. The entire teachings of the above applications are incorporated herein by reference.

BACKGROUND OF THE INVENTION

The emerging field of bioelectronics seeks to exploit biology in conjunction with electronics in a wider context encompassing, for example, micro or nanoscale biomaterials for information processing, information storage and actuators. A key aspect is the interface between biological materials and electronics since it defines the target, sensitivity, selectivity and speed of the device.

The detection of odorants has also been pursued through the development of electronic noses that are used for environmental monitoring, medical testing, and food and drink production. In the most sophisticated systems, a unique chemical fingerprint can be generated by an array of sensors and then identified by pattern-recognition techniques, such as the smell of a rose (Lundstrom, I., *Nature,* 406:682-3, 2000).

Attempts to measure odors with electronic instruments were made in the 1950s, but the modern field of artificial olfaction, according to Lundstrom (Lundstrom, I., *Nature,* 406:682-3, 2000), began in 1982 with the work of Persaud and Dodd (Persaud, K., and Dodd G., *Nature.* 299:352-5, 1982). They used a small array of gas-sensitive metal-oxide devices to classify odors. While there has been a steady increase in the number of systems using chemical sensor arrays, their success depends not only on the development of new sensor technologies, but also on the availability of powerful pattern-recognition software (Lundstrom, I., *Nature,* 406:682-3, 2000). This last aspect is particularly important for sensor arrays that produce a composite response for detecting targets that emit a characteristic array of odorants. However, these systems suffer from many limitations that are superseded by the olfactory cells in animals.

Olfactory receptor neurons (olfactory cells) are bipolar nerve cells that densely line the olfactory membrane in the recess of the nose, wherein odor receptor proteins that respond to odor molecules, called olfactory receptors, are expressed at high density. In olfactory cells, the chemical substances diffusing in the air from the stimulus source are detected by olfactory receptors and converted to neural signals. These neural signals are transmitted to the brain through the olfactory bulb (mitral cells or tufted cells) and the olfactory cortex such as the piriform cortex (pyramidal cells) and allow humans to sense odors. The interaction of odorants with olfactory receptors on the apical cilia of olfactory neurons is the first step in the perception of smell. The large number (e.g., approximately ~350 in human and 1200 in dog) and structural diversity of the opsin-like GPCRs that function as olfactory receptors underlies the ability to detect and discriminate a vast number of volatile compounds (Buck, L. and Axel, R., *Cell* 65: 175-187, 1991; Fuchs, T. et al., *Hum. Genet.* 108: 1-13, 2001). Olfactory receptors interact with a diverse array of volatile molecules. It is widely accepted that every odorous molecule binds to several ORs and vise versa. This binding pattern generates a unique combinatorial code that generates a specific aroma for each odorant and enables the organism to distinguish it from other molecules. This system is highly sensitive and allows to discriminate between two protein isomers and at times even between two optical enantiomers.

Notwithstanding recent advances in bioelectronic sensing device, a quest for real time bio-sensing nanodevices with improved speed, precision and sensitivity still remains.

SUMMARY OF THE INVENTION

The invention provides an improved bio-sensing microsurface plasmon polariton detector comprising: a stabilized G-protein coupled receptor on a support embedded in a microfluidic device, a test composition delivery system, a real time receptor-ligand binding detection method utilizing surface plasmon polariton (SPP) technology, and a test composition recognition program. In certain embodiments, the test composition is an odorant. The present invention is based on the solutions to the problems of providing odorants to the olfactory receptors, which are maintained in a moist or wet form and delivering the light delivery and signal read out systems of the SPP, that are dry. The present invention relates to improvements of WO2009/018467 filed on Jul. 31, 2008, the contents of which are incorporated herein by reference.

The present invention has been made in view of the foregoing circumstances and an object thereof is to provide improvements for achieving small size and high accuracy for a measuring apparatus.

The detector provided in the optical coupling area interacts with the substance to be detected and, as a result, a coupling state of light in the optical coupling area varies. That is, when there is a substance to be detected, the shifted amount of light from the first waveguide to the second waveguide changes. Thus, the substance to be detected can be analyzed by measuring an amount of outgoing light from the second waveguide. In the present invention, the light shifted to the second waveguide is measured unlike in the conventional method where the measurement is carried out by detecting a small change in the incoming light of high intensity. Thus, favorable measurements with high S/N ratio can be obtained. Moreover, since the measurement sensitivity is high, a short and small optical coupling area suffices, enabling the measuring apparatus to be made smaller. Since it is possible in principle that measurement can be done by the light of a single wavelength; there is no need to use white light as is the case in conventional surface plasmon resonance sensors. Thus, the apparatus can further be made smaller due to the relatively smaller size of available single wavelength light emitters.

Additionally, a structure may be such that the detector contains metal film. By employing this structure, it is possible to carry out a measurement utilizing a change in a state of the surface plasmon resonance, so that the apparatus can be made smaller and the measurement can be made with high accuracy.

The detector may further be structured such that an olfactory receptor which selectively captures an odor or substance to be detected is disposed on a surface of the detector. By implementing this structure, the substance to be detected can be measured in a sensitive manner. Moreover, there may be provided a plurality of detectors and a plurality of different receptors may be placed on the respective plurality of detectors. By implementing this structure, a plurality of substances to be detected can be measured quickly and accurately.

The method for introducing a sample may be any of a method of dropping sample solution, a method in which a flow cell with an exposed detector is provided and sample solution flows through this cell, and others. For example, a structure may be such that there is provided a flow path in contact with the detector and a surface of the detector is exposed on this flow path. By employing this structure, the introduction of sample becomes simplified, so that a plurality of substance to be detected can be measured quickly and accurately.

For example, according to the present invention, there may be provided an optical waveguide sensor which further includes a third waveguide having an exit end for detecting light, wherein there is further provided a detector, disposed between the first waveguide and the third waveguide, which interacts with a substance to be detected.

Within the present invention, there is provided a measuring method in which introduction of a sample in the optical coupling area causes a change in a physical property, such as the refractive index of the optical coupling area; the intensity of detecting light output from the second waveguide is measured; and the presence or absence of a substance to be detected is ascertained or quantified by the measuring. There is also provided a measuring method in which incoming light is introduced in the first waveguide; a sample is introduced which causes binding to an immobilized olfactory receptor and which further changes the refractive index of the optical coupling area; the intensity of detecting light outputted from the second waveguide is measured; and the presence or absence of a substance is ascertained or quantified by the measuring.

According to the present invention, adopted is a system in which a plurality of waveguides are used and the substances to be detected are analyzed by utilizing the optical mode coupling or the surface plasmon resonance, so that the measuring apparatus can be made smaller and the measurement can be done with high precision.

The receptor can be expressed in and purified from a cell-free or cell expression system. In certain aspects, the receptor is purified by a method comprising immunoaffinity purification or chromatography or a combination thereof. Further, the receptor can be stabilized on nanotechnology using suitable surfactants, including, but not limited to, surfactant peptides.

The said nanodevice provides a greater surface area for better precision and sensitivity to odorant detection. The invention further provides a microfluidic chip containing a stabilized receptor immobilized on a support, and arranged in at least two dimensional microarray systems. The invention also provides a method of delivering odorant comprising the step of manipulating the bubbles in complex microfluidic networks wherein the bubbles travel in a microfluidic channel carrying a variety of gas samples to a precise location on a chip. The invention further provides method of fabricating hOR17-4 olfactory receptor. Such chips and microfluidics devises are described, for example, in WO2009/018467 filed on Jul. 31, 2008, which is incorporated herein by reference in its entirety.

The invention relates to an improved physical structure of the olfactory receptor support and the effects of said improvements on Plasmon occurrence and propagation losses typical of the existing design.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Using Superdex 200 GL 5/150 SEC analysis in different detergents, running buffer, SEC buffer (25 mM TrisHCl, 150 mM NaCl, 10% glycerol) supplemented 3×2 CMC cyclofos 5 (gray line), Tri-mix (dashed line), 10×CMC FC14 (black line) and SEC buffer only (black dotted line). The arrow indicates void volume. (B) Monitoring the effect of hOR17-4 aggregation states in different buffers with different pH, NaCl concentration, and reducing agent. (C) SDS/PAGE of the elution fractions from affinity purification with the same buffers as in B.

Figure 16A:
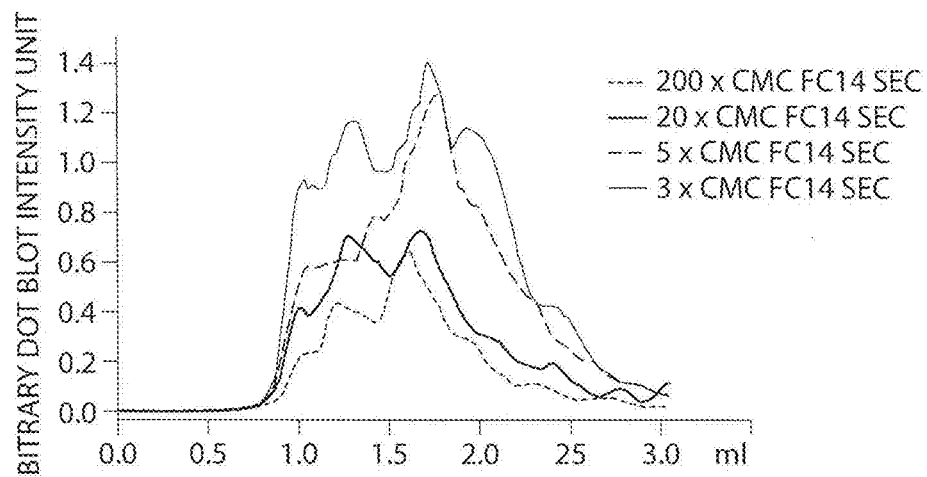
Figure 16B:
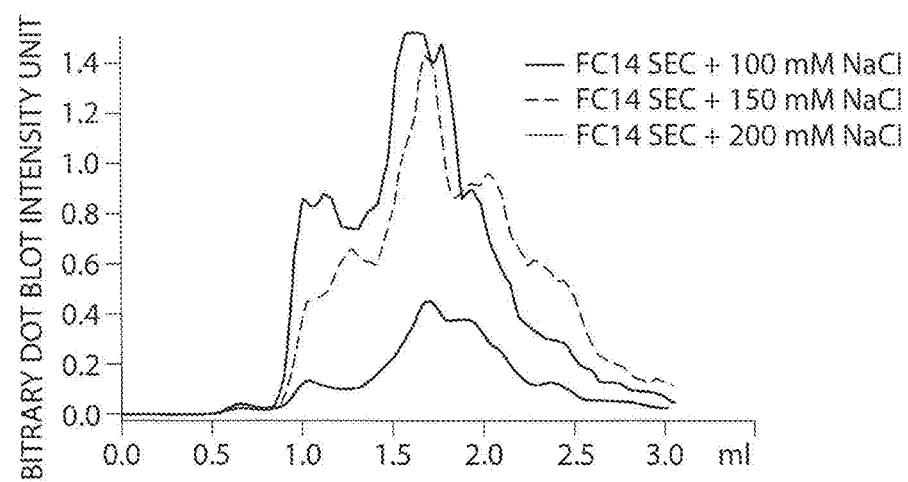
Figure 16C:
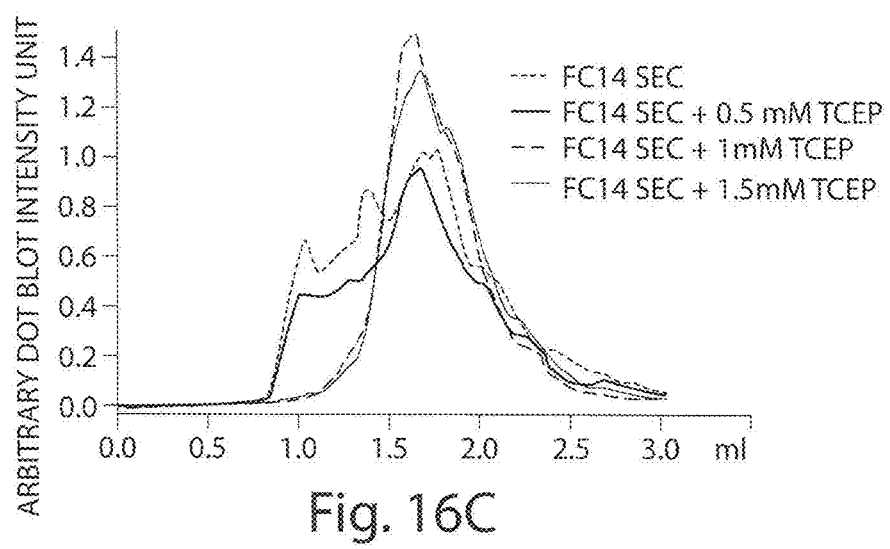

FIGS. 16A-C are plots showing fine coarse SEC analysis of hOR17-4 aggregation states. Different concentrations of FC14 (A), NaCl (B) and TCEP (C) using a Superdex 200 GL 5/150. Running buffer is SEC buffer supplemented with 10×CMC FC4, unless otherwise stated.

Figure 17:
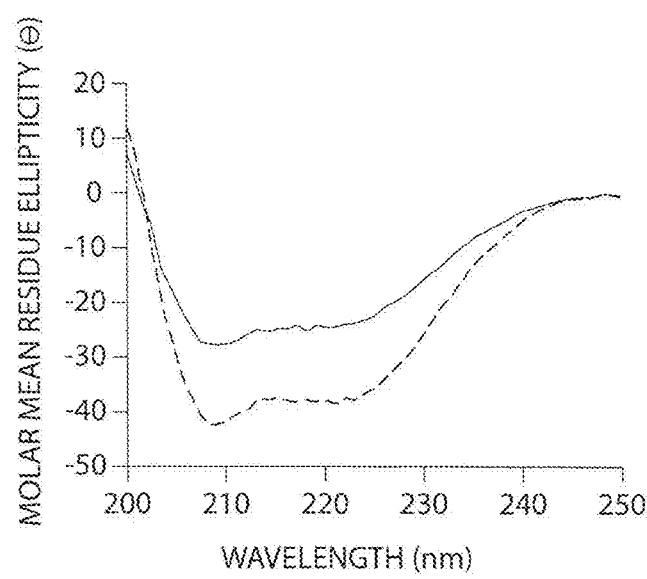

FIG. 17 is a plot of CD spectra of hOR17-4. Purified hOR17-4 diluted to 0.3 mg/ml in Buffer 1 (black line) 25 mM Tris (pH 7), 10% glycerol, 3×CMC FC14 and 200 mM NaCl; and buffer 2 (gray line) 25 mM Tris (pH 7), 10% glycerol, 3×CMC FC14 and 150 mM NaCl and 1 mM TCEP.

Figure 18A:
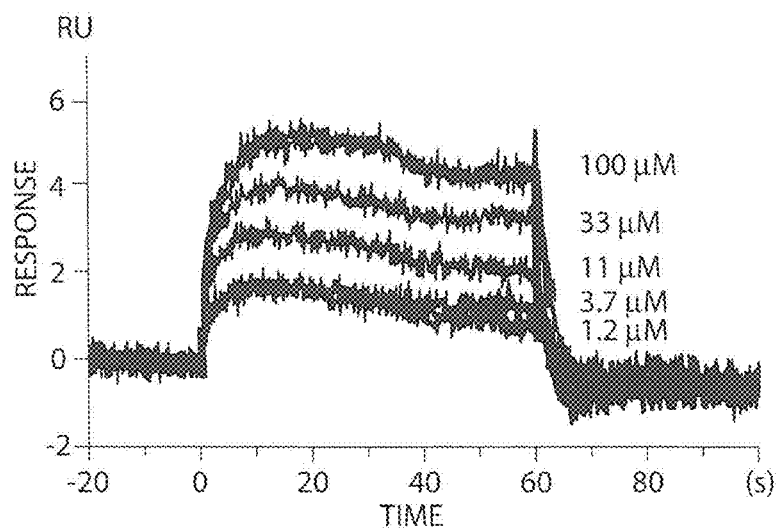

FIGS. 18A and B shows surface Plasmon resonance (SPR) detection of the interaction between hOR17-4 with the known hOR17-4-binding odorant undecanal. (A) Responses from injections at 1.2, 3.7, 11, 33 and 100 uM. Sensorgram are double-referenced and solvent corrected. Experiments with an odorant that is a known non-binder for hOR17-4 did not show any interaction (results not shown). (B) Equilibrium binding responses plotted versus undecanal concentration and fitted to a simple binding isotherm to yield affinity of about 22 uM for hOR17-4.

FIGS. 19A and B shows the codon-optimized hOR17-4 sequence. The DNA (A) and corresponding amino acid (B) sequence of synthetic hOR17-4 olfactory receptor gene. The DNA sequence was human codon-optimized and a mammalian Kozak ribosome binding site introduced upstream of the translation start site. Translation start and stop sites as well as restriction cloning sites are indicated. The engineered construct also contains a C-terminal tag (underlined) consisting of a glycine linker followed by a nonapeptide epitope for the monoclonal rho1D4 antibody.

FIG. 20 shows induction of hOR17-4 in stable HEK293S cell lines. (A) Stable inducible cell lines were generated in HEK293S cells using the T-REx system (Invitrogen) expressing hOR17-4 tagged with the rho1D4 tag (TETSQVAPA (SEQ ID NO: 50)) at the C-terminus. The pooled cells were then subcloned, expanded, and then tested for induction in media supplemented with (+) or without (−) 1 μg/ml tetracycline for 48 hours. Levels of hOR17-4 were probed via SDS-PAGE western blotting using the rho antibody. Clones 1 and 5 showed the highest levels of induction while maintaining undetectable background levels in the absence of tetracycline. Clone 5 was selected for all subsequent experiments. (B) Addition of sodium butyrate enhances induced expression of hOR17-4. Inducible HEK293 was subjected to a dosage time course using the indicated concentrations of tetracycline and sodium butyrate. Samples were harvested, subjected to dot blot analysis (western blot against rho1D4), and the results quantified by spot densitometry. Tetracycline in conjunction with sodium butyrate increased expression by approximately 4-5 fold over tetracycline alone at all time points tested. Tetracycline was necessary to cause induction, as no expression was detected if sodium butyrate was used alone. Additionally, increasing tetracycline concentration to 2 μg/ml had no significant effect on induction levels.

Figure 21A:
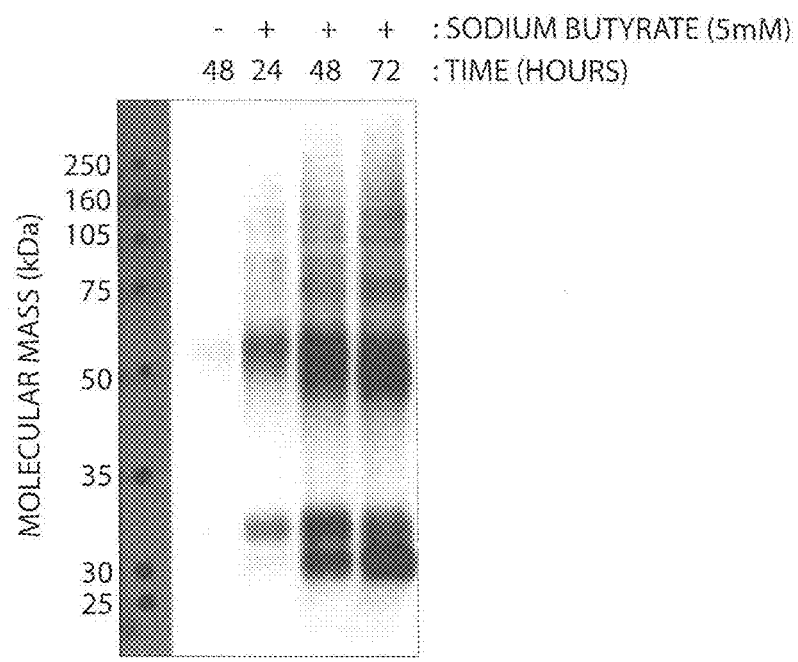

FIGS. 21A and B are gels showing high-level induction correlates with a band shift of hOR17-4. (A) Time point samples (from FIG. 2) were normalized to total protein content and subjected to SDS-PAGE western blotting against rho1D4. All lanes were treated with 1 μg/ml tetracycline with (+) or without (−) sodium butyrate (5 mM) for the time indicated. (B) hOR17-4-inducible HEK293S cells were subjected to a dosage time course using the indicated concentrations of sodium butyrate. All samples were co-treated with 1 μg/ml tetracycline. Samples were normalized to total protein content and subjected to SDS-PAGE western blotting against rho1D4.

Figure 22A:
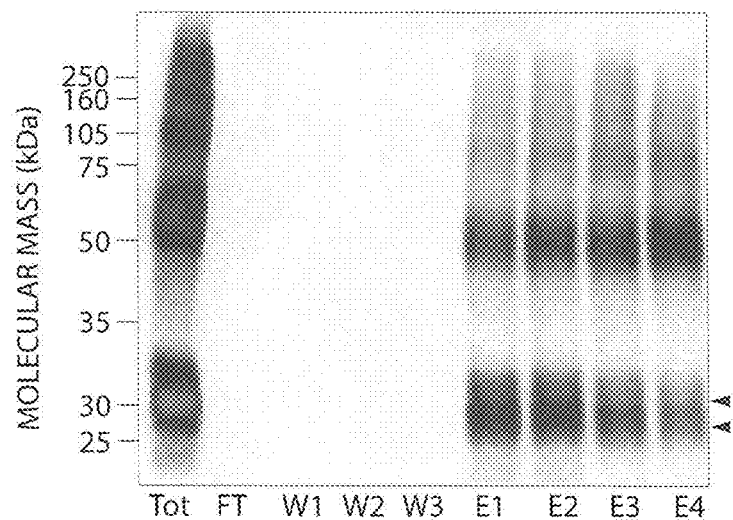

FIGS. 22A and B are SDS PAGE gels showing immunoaffinity purification of hOR17-4. Six 150 mm tissue culture plates of were grown to 90% confluence then induced and treated with tetracycline (1 μg/ml) and sodium butyrate (5 mM) for 48 hours. Plates were scrape harvested, solubilized, and the processed lysate subjected to immunoaffinity purification using rho1D4 antibody linked to sepharose beads for capture. Bound proteins were washed and then eluted using the nonapeptide TETSQVAPA (SEQ ID NO: 50). Samples were subjected to SDS-PAGE followed by either western immunoblotting with rho antibody (A) or total protein staining with Sypro Ruby (B). Black triangles indicate the 30 and 32 kD monomer forms. Tot, total lysate; FT, flow through; W, wash; E, elution.

Figure 23A:
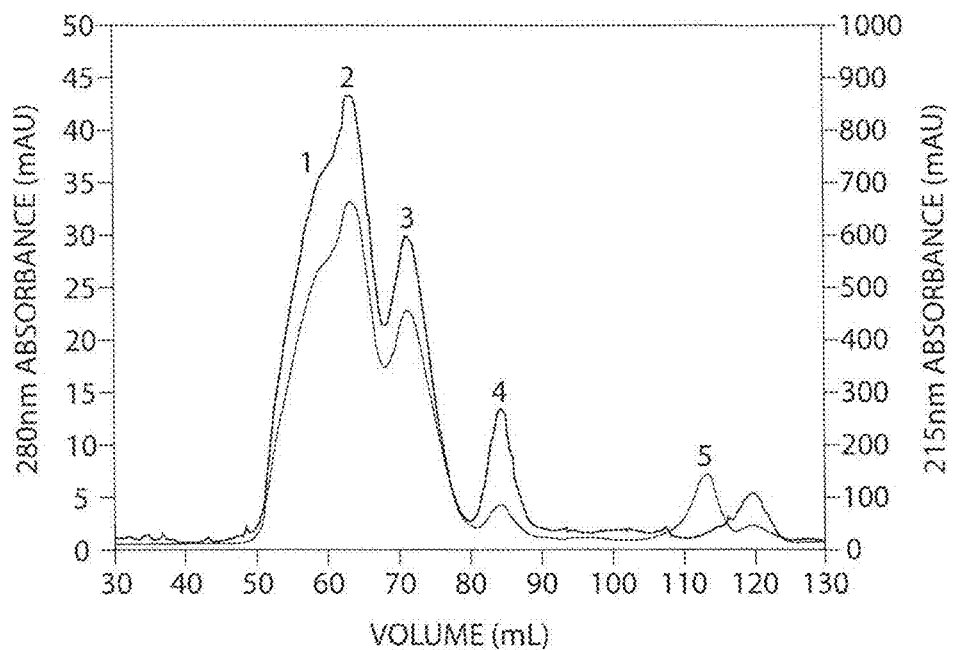

FIGS. 23A and B shows (A) Size exclusion chromatography (SEC) on immunoaffinity-purified hOR17-4. Absorbance was simultaneously recorded at 280 nm (black line, values on left axis) and 215 nm (grey line, values on right axis). The peaks indicated by numbers were pooled and concentrated. Peak 5 consists of the elution nonapeptide from the immunoaffinity purification. (B) Total protein staining of SEC peak fractions. Load is the original immunoaffinity purified sample applied to the chromatography column. Peak numbers refer to those designated in (A). Peak 3 contains monomeric hOR17-4 at >90% purity. Total monomer yield was 2.6 μg per 150 mm culture plate.

FIG. 24 shows construction of hOR17-4-inducible HEK293S GnT1−/− cell lines for use in liquid bioreactor culture. Clones were tested for induction after 48 hours in plain media (−) or media supplemented with 1 ug/mL tetracycline (+) or tetracycline plus 5 mM sodium butyrate enhancer (++). Arrows indicate the position of the 32 kD and 30 kD monomer forms. (A) Levels of hOR17-4 were probed via SDS-PAGE western blotting against the rho tag (rho1D4 mAb). Clones 3 and 8 show high levels of induction following the addition of sodium butyrate but have low levels of the potentially unglycosylated 30 kD monomer form of hOR17-4, unlike Clone 11 and previous clones in the HEK293S system. Clone 3 was selected for subsequent bioreactor experiments. (B) In order to investigate the potential N-linked glycosylation of hOR17-4, the consensus glycosylation sequence (-Asn-Gln-Ser-) was altered using site directed mutagenesis to change the asparagine at position 5 to glutamine (N5Q mutation). Following the generation of new stable hOR17-4(N5Q) inducible clones, the SDS-PAGE migration pattern of receptor monomer was compared to wild-type following induction. Mutation of the glycosylation site (N5Q) eliminated the upper form (32 kD) of hOR17-4 monomer and only lower form (30 kD) is present, indicating the size discrepancy is indeed due to glycosylation on Asn5.

Figure 25:
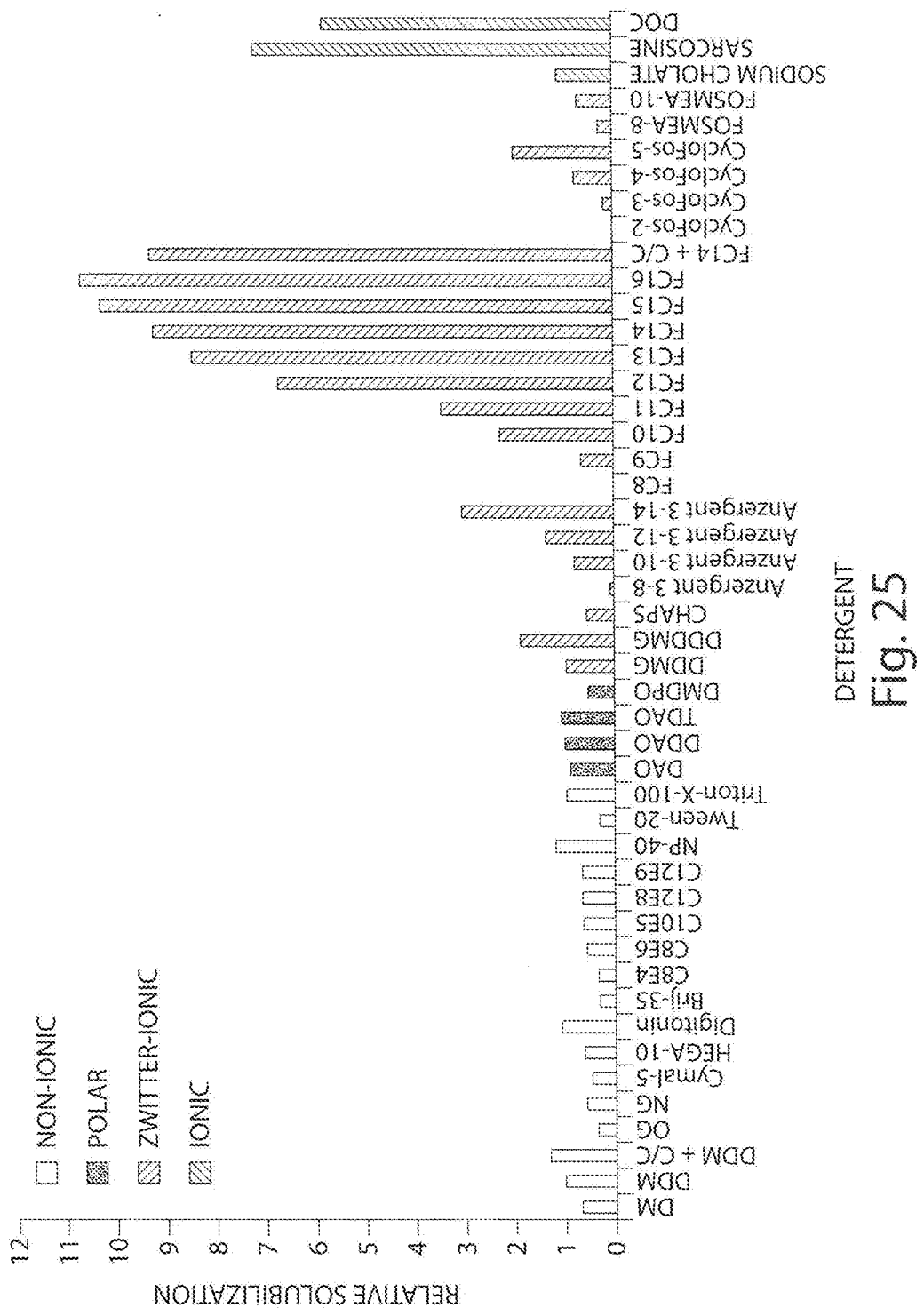

FIG. 25 is a bar graph showing expression of hOR17-4 was induced with tetracycline (1 μg/ml) and sodium butyrate (5 mM) for 48 hours and receptors solubilized in PBS containing detergents for 4 hours at 4° C. All detergents were used at a concentration of 2% wt/vol unless otherwise indicated. Relative solubilization corresponds to the fold increase over dodecyl maltoside (DDM) in solubilizing hOR17-4 monomer/dimer. Detergent abbreviations used are: DM, decyl maltoside; DDM, dodecyl maltoside; C/C, CHAPS (1%) and Cholesterol hemisuccinate (0.2%); OG, octyl glucoside; NG, nonyl glucoside; NP40, nonidet P40; DAO, n-decyl-N,N-dimethylamine-N-oxide; DDAO, n-dodecyl-N,N-dimethylamine-N-oxide; TDAO, n-tetradecyl-N,N-dimethylamine-N-oxide; DMDPO, dimethyldecylphosphine oxide; DDMG, n-decyl-N—N-dimethylglycine; DDDMG, n-dodecyl-N—N-dimethylglycine; sarcosine, sodium dodecanoyl sarcosine; DOC, deoxycholate.

Figure 26A:
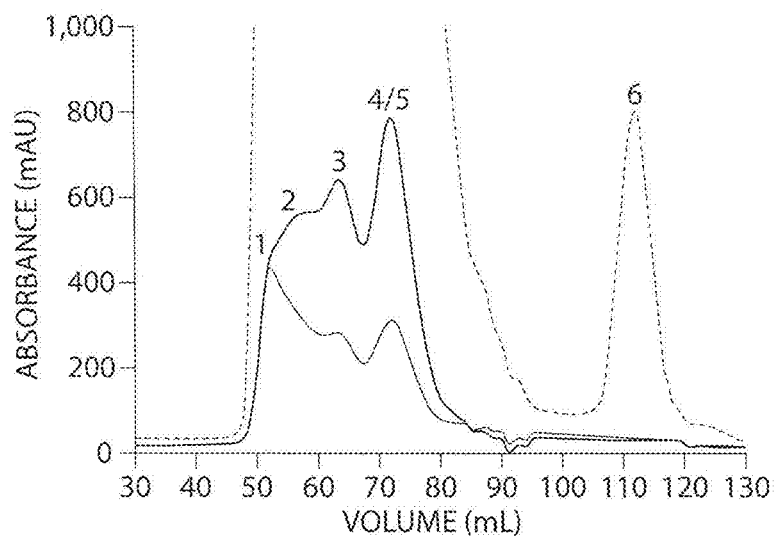

FIG. 26 shows (A) Size exclusion chromatography (SEC) on immunoaffinity-purified hOR17-4. Absorbance was recorded at 280 nm (black), 254 nm (gray), and 215 nm (dashed). Peaks 1-5 (indicated by numbers) were pooled and concentrated. The predicted monomer peak was pooled into an early fraction (4) and a late fraction (5). Peak 6 contains the nine amino acid elution peptide TETSQVAPA (SEQ ID NO: 50) from the immunoaffinity purification. (B) Total protein staining of SEC peak fractions. Column fractions were collected and subjected to SDS-PAGE followed by staining with Sypro Ruby. Load is the original immunopurified sample applied to the chromatography column. Peak numbers refer to those designated in (A). Peaks 4 and 5 contain monomeric hOR17-4 at >90% purity.

FIG. 27 shows characterization of purified hOR17-4 by circular dichroism spectroscopy. Purified hOR17-4 monomer was analyzed by both far-UV and near-UV circular dichroism spectroscopy. (A) Far-UV CD spectrum of hOR17-4 displaying secondary structure of 49% alpha helix. Spectrum shown is the average of 5 replicate scans. Mean residue ellipticity [θ] (degree×cm$^2$×dmol$^{-1}$). (B) Near-UV CD spectrum of hOR17-4 showing distinct tertiary structure peaks. Functional bovine rhodopsin has a similar peak in this region, while non-functional opsin mutants show flat spectra characteristic of a misfolded globular state.

Figure 28A:
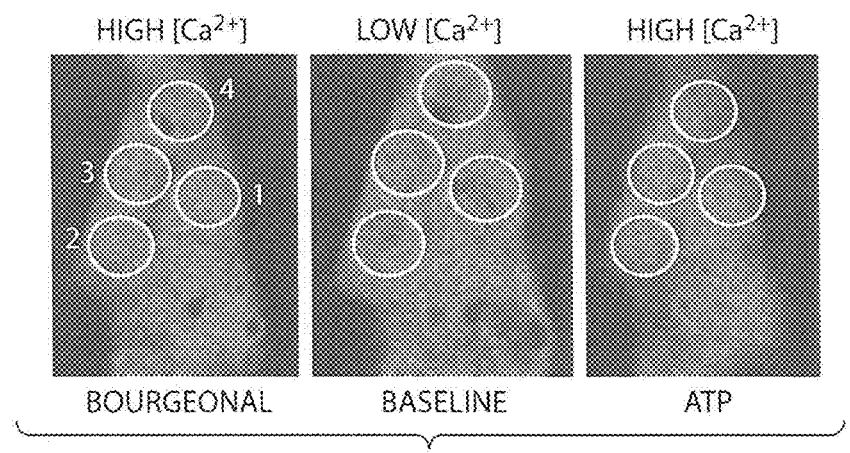
Figure 28B:
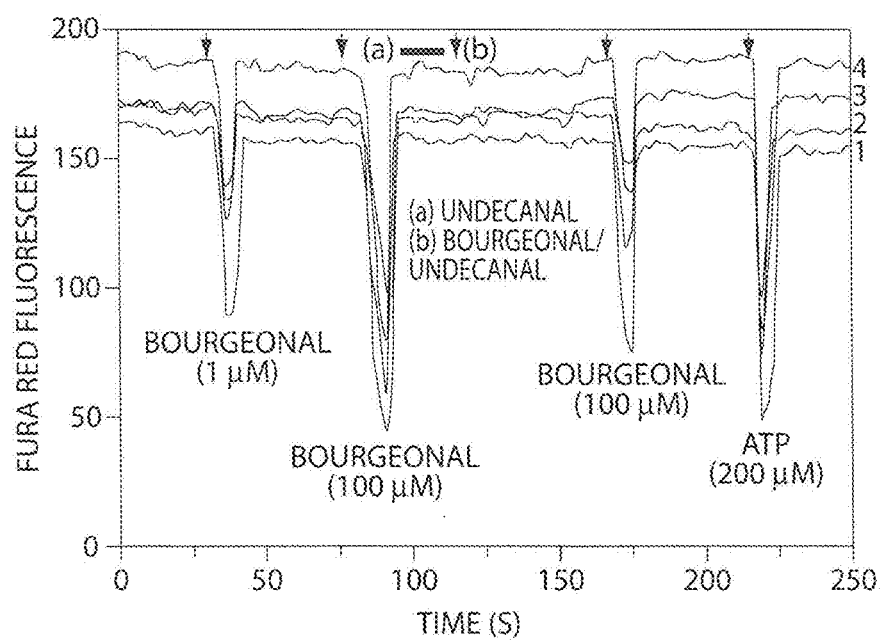

FIG. 28 shows the results of calcium-influx assays of cell surface expressed hOR17-4. hOR17-4 expressed in a stable inducible HEK293S cell line exhibits specific activation by its cognate ligand bourgeonal. (A) Transient changes of the cytosolic $Ca^{2+}$ concentration were recorded with confocal microscopy using Fura-Red (Ex 488 nm/Em 650 nm) as a fluorescent $Ca^{2+}$ indicator. The decrease of the fluorescence signal induced by receptor activation in response to bourgeonal (100 µM) corresponds to an increase of the cytosolic $Ca^{2+}$ concentration. The application of 200 µM adenosine triphosphate (ATP) served as a control of HEK293S cell excitability. (B) In a randomly selected field of view, Fura Red fluorescence intensities of odorant-induced $Ca^{2+}$ responses were recorded on four individual cells (1, 2, 3, 4) as a function of time. hOR17-4 induces transient $Ca^{2+}$ signaling to consecutive stimulations by bourgeonal (1 µM; 100 µM). Arrows indicate the time point of odorant application. The preincubation (black bar) with the hOR17-4 antagonist undecanal (100 µM) inhibited hOR17-4 activation by bourgeonal (100 µM) during co-application (arrow) with undecanal (100 µM). After subsequent odorant washout, cells were again excitable with bourgeonal (100 µM).

Figure 29A:
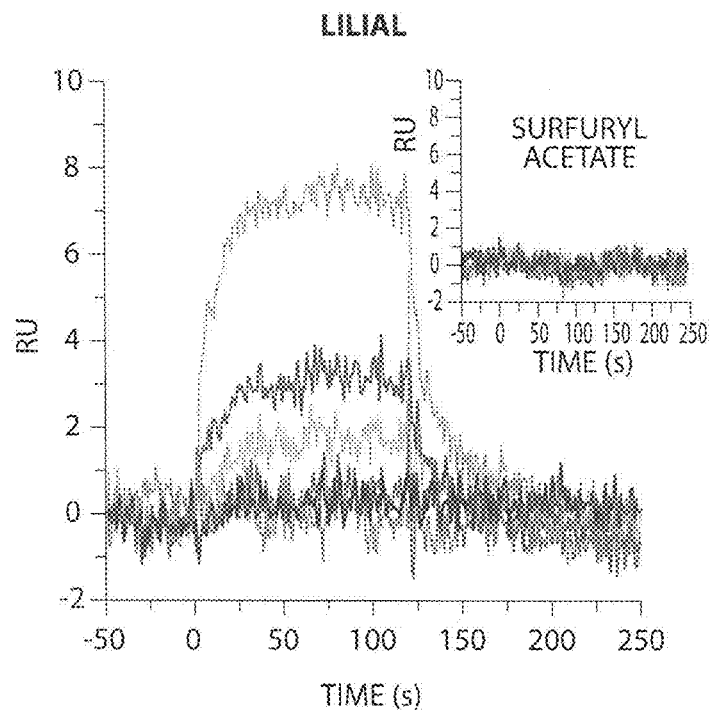
Figure 29B:
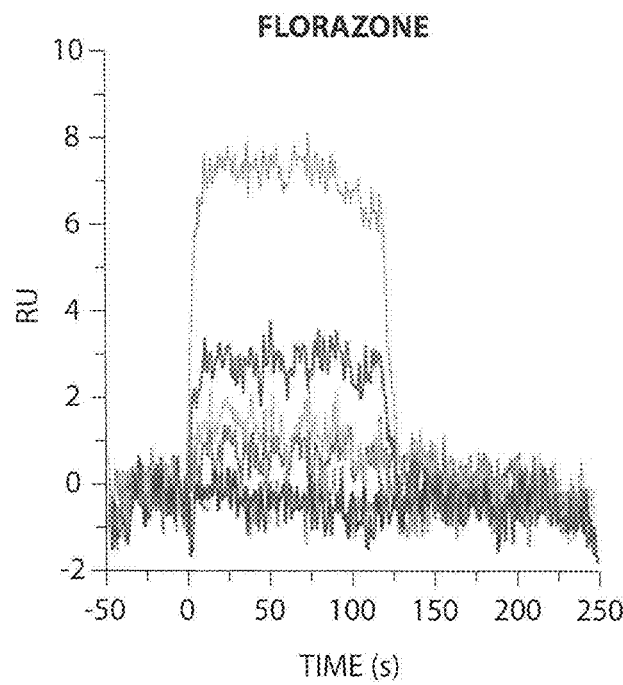

FIG. 29 shows the detection of odorant binding activity of OR was monitored in real time using a Biacore A100 SPR instrument. The hOR17-4 was first captured on the SPR chip surface via a covalently immobilized rho1D4 mAb. Time courses of odorant binding were recorded following odorant application. The receptor bound the specific odorants lilial (A) and floralozone (B) in a concentration dependent manner. Odorant binding curves shown are: blank control (black), 5 µM (red), 10 µM (light blue), 20 µM (dark blue), and 40 µM (green). No response was seen for the non-binding control odorant sulfuryl acetate, as indicated by the 40 µM application (orange curves) and the full series of concentration data (inset). All results were simultaneously subtracted from a reference channel containing mAb and blank buffer.

DETAILED DESCRIPTION OF THE INVENTION

The present invention features a bio-sensing nanodevice comprising: a stabilized, G-protein coupled receptor [2] on a support, a real time receptor-ligand binding detection method [6], a test composition delivery system [5] and a test composition recognition program [7]. The G-protein coupled receptor [2] can be stabilized on nanotechnology using a surfactant, such as a surfactant peptide. The said nanodevice provides a greater surface area for better precision and sensitivity to odorant detection.

The test composition is a composition delivered to the device for detecting potential binding to the G-protein coupled receptor. In certain aspects, the test composition comprises an odorant.

SPPs are generally known in the art and are described, for example, in U.S. Pat. No. 7,295,294, which is incorporated herein by reference. In particular, the SPP comprises a first optical waveguide sensor that includes: a first waveguide having an inlet end for incoming light; a second waveguide having an exit end for detecting light; and an optical coupling area where said first waveguide and said second waveguide are positioned within a predetermined interval therebetween, wherein in the optical coupling area there is provided a detector, disposed between the first waveguide and the second waveguide, which interacts with a substance to be detected. The incoming light is led to the first waveguide. Part of the incoming light shifts to the second waveguide. A shifted amount of light varies according to the presence or absence of the substance to be detected, so that the light extracted from the exit end of the second waveguide is measured as the detecting light.

The detector of the present invention which is provided in the previously described optical coupling area, interacts with the substance to be detected and, as a result, a coupling state of light in the optical coupling area varies. That is, when there is a substance to be detected, the shifted amount of light from the first waveguide to the second waveguide changes. Thus, the substance to be detected can be analyzed by measuring an amount of outgoing light from the second waveguide. In the present invention, the light shifted to the second waveguide is measured unlike in the conventional method where the measurement is carried out by detecting a small change in the incoming light of high intensity. Thus, favorable measurements with high S/N ratio can be obtained. Moreover, since the measurement sensitivity is high, a short and small optical coupling area suffices, enabling the measuring apparatus to be made smaller. Since it is possible in principle that measurement can be done by the light of a single wavelength; there is no need to use white light as is the case in conventional surface plasmon resonance sensors. Thus, the apparatus can further be made smaller due to the relatively smaller size of available single wavelength light emitters.

A second optical waveguide sensor according to the present invention, includes: a first waveguide having an inlet end for incoming light; a second waveguide having an exit end for detecting light; an optical coupling area where said first waveguide and said second waveguide are positioned within a predetermined interval there between; and a detector, interacting with a substance to be detected, which is positioned in close proximity to the first waveguide and is located within an area covered from the inlet end up to the optical coupling area. In this sensor, the incoming light is led to the first waveguide. Part of the incoming light shifts to the second waveguide. A shifted amount of light varies according to the presence or absence of the substance to be detected, so that the light extracted from the exit end of the second waveguide is measured as the detecting light. The detector is provided in the close proximity of the first waveguide and is located within an area covered from the inlet end up to the optical coupling area. The detector interacts with a substance to be detected, thereby causing a change in the lost amount of light in the optical coupling area. Thus, if substance to be detected is present, a shifted amount of light from the first waveguide to the second waveguide will change. Then, the substance to be detected can be analyzed by measuring an amount of outgoing light from the second waveguide. With this sensor, the light shifted to the second waveguide is to be measured unlike in the conventional measuring equipment where the measurement is carried out by detecting a small change in the incoming light of high intensity. Thus, favorable measurements with high S/N ratio can be obtained. Moreover, since the measurement sensitivity is high, a short and small optical coupling area suffices, enabling the measuring apparatus to be made smaller. Moreover, since it is possible in principle that measurement can be done by the light of a single wavelength; there is no need of using white light as in the conventional SPR sensor. Thus, the apparatus can be made smaller.

In the second optical waveguide sensor, a structure may be such that the detector contains metal film. By employing this structure, it is possible to carry out a measurement utilizing a change in a state of the surface plasmon resonance, so that the apparatus can be made smaller and the measurement can be made with high accuracy.

The detector according to the present invention may be structured such that an olfactory receptor which selectively captures an odor or substance to be detected is disposed on a surface of the detector. By implementing this structure, the substance to be detected can be measured in a sensitive manner. Moreover, there may be provided a plurality of detectors and a plurality of different receptors may be placed on the respective plurality of detectors. By implementing this structure, a plurality of substances to be detected can be measured quickly and accurately.

The method for introducing a sample may be any of a method of dropping sample solution, a method in which a flow cell with an exposed detector is provided and sample solution flows through this cell, and others. For example, a structure may be such that there is provided a flow path in contact with the detector and a surface of the detector is exposed on this flow path. By employing this structure, the introduction of sample becomes simplified, so that a plurality of substance to be detected can be measured quickly and accurately.

For example, according to the present invention, there may be provided an optical waveguide sensor which further includes a third waveguide having an exit end for detecting light, wherein there is further provided a detector, disposed between the first waveguide and the third waveguide, which interacts with a substance to be detected.

Moreover, according to the present invention, there is provided a measuring method in which used is a sensor having a first waveguide, a second waveguide and an optical coupling area where said first waveguide and said second waveguide are positioned within a predetermined interval there between, the method including: introducing incoming light in the first waveguide; introducing a sample in the optical coupling area to cause a change in a physical property, for example, the refractive index, of the optical coupling area; measuring the intensity of detecting light outputted from the second waveguide; and detecting the presence or absence of a substance to be detected or quantitating the substance by the measuring. Moreover, according to the present invention, there is provided a measuring method in which used is a sensor having a first waveguide, a second waveguide and an optical coupling area where said first waveguide and said second waveguide are positioned within a predetermined interval there between, the method including: introducing incoming light in the first waveguide; introducing a sample, in an area in contact with the first waveguide between an introducing end of the incoming light and the optical coupling area, to cause binding to an immobilized olfactory receptor and change the refractive index, of the optical coupling area; measuring the intensity of detecting light outputted from the second waveguide; and detecting the presence or absence of a substance to be detected or quantitating the substance by the measuring.

With these measuring methods, the light to be introduced may be monochromatic light, so that the structure of the apparatus can be simplified. The light to be introduced may be a single light beam or various types of light beams. According to the present invention described as above, adopted is a system in which a plurality of waveguides are used and the substances to be detected are analyzed by utilizing the optical mode coupling or the surface plasmon resonance, so that the measuring apparatus can be made smaller and the measurement can be done with high precision.

In some embodiments, the stabilized G-protein coupled receptor is purified from an expression system and is in a stabilized form on the support. In one embodiment, the G-protein coupled receptor [2] is stabilized with a surfactant peptide. G-protein coupled receptors are cell-membrane 7-transmembrane-type receptors coupled with trimeric G-protein. This type further falls into the cAMP system producing cAMP as the second messenger and the inositol phospholipid transmitter system producing inositol-1,4,5-triphosphate ($IP_3$) or diacyl glycerol (DG) as the second messenger. cAMP can activate some pathways in single or parallel. In some types of nerve cells, such as olfactory-receptor nerve cells, cAMP-dependent ion-channels are opened, the cellular membrane is depolarized, and $Ca^{2+}$ enters the cell through the channel, transiently increasing intracellular $Ca^{2+}$ concentration. cAMP activates cAMP-dependent kinase (A kinase), phosphorylates serine and/or threonine residues of function-protein, and modifies its activity. On the other hand, $IP_3$ binds to $IP_3$ receptors on the endoplasmic reticulum and accelerates the release of $Ca^{2+}$ into a cell. Diacyl glycerol promotes the action of hormones and the like by activating C kinase.

In one preferred embodiment, the G-protein coupled receptor [2] is an olfactory receptor. In some embodiments, the olfactory receptor is a mammalian receptor. In another embodiment, the olfactory receptor is selected from the group consisting of OR17-4, OR23 and S51. In another embodiment, the olfactory receptor is selected form the group consisting of hOR17-4 (human), mOR23 (mouse), mS51. In yet another embodiment, the olfactory receptor is hOR17-4. The olfactory receptor is preferably stabilized. Stabilization can be accomplished by mixing the olfactory receptor with a surfactant. A preferred class of surfactants is protein stabilizing surfactants. Protein stabilizing surfactants include commercially available surfactant including, but not limited to, n-Tetradecylphosphocholine 12, 13, 14, 15, 16 (also called FC12, FC13, FC14, FC15, FC16), digitonin and trimix [CHAPS (3-cholamidopropyl-dimethylammonio-1-propane sulfonate), CHS (Cholesteryl hemisuccinate), and DDM [n-dodecyl-beta-D-maltopyranoside)]. Protein stabilizing surfactants also include surfactant peptides. The surfactants of the present invention preferably self-assemble in solution. The surfactant, together with the olfactory receptor, forms a new self-assembled nanostructure. The surfactants are amphiphilic molecules that tend to aggregate in order to isolate the hydrocarbon chain from contact with water. The common feature for this self-association is the formation of a polar interface, which separates the hydrocarbon and water regions, in many instances, forming a spherical micelle consisting of typically 50-100 lipid molecules arranged so that their hydrocarbon tails form the interior of the micelle, and the polar head groups act as a shield against the surrounding water. Depending on the surfactant and its concentration, various structures can be found, including liposomes, lamellar phase, and hexagonal, cubic or tubular structures.

A surfactant peptide is a short peptide with a hydrophilic head group and a lipophilic tail group. In some embodiments, the surfactant peptide has a sequence of less than or equal to 10 amino acids. The hydrophilic head group is comprised of a polar and/or charged (either positively or negatively charged at physiological pH) amino acid. The hydrophobic head group is comprised of a hydrophobic amino acid such as a non-polar and/or uncharged amino acid. In one embodiment, the hydrophilic amino acid is positively charged at physiological pH. In another embodiment, the hydrophilic amino acid is negatively charged at physiological pH. When dissolved in water or in an ionic solution, the peptide surfactants undergo self-assembly to form micelles, nanovesicles or nanotubes. Surfactant peptides have been described, for example, in U.S. Pat. No. 7,179,784, U.S. Patent Application Publication 2003/0176335 A1 and U.S. Patent Application Publication No. 2006/0211615 A1, the teachings of which are incorporated by reference herein.

In certain aspects, the surfactant peptides used in accordance with the present invention are peptides having a formula selected from the group consisting of:

a. $(\Phi)_m(+)_n$ (Formula (1)), b. $(+)_n(\Phi)_m$ (Formula (2)), c. $(\Phi)_m(-)_n$ (Formula (3)), d. $(-)_n(\Phi)_m$ (Formula (4)), e. $(-)_n(\Phi)_m(-)_n$ (Formula (5)), f. $(+)_n(\Phi)_m(+)_n$ (Formula (6)), g. $(\Phi)_m(-)_n(\Phi)_m$ (Formula (7)), h. $(\Phi)_m(+)_n(\Phi)_m$ (Formula (8)), i. $(+)_n(\Phi)_m(-)_n$ (Formula (9)), j. $(-)_n(\Phi)_m(+)_n$ (Formula (10)), k. $(\tau)_m(\Phi)_m$ (Formula (11)), l. $(\Phi)_m(\tau)_n$ (Formula (12)), m. $(\tau)_n(\Phi)_m(\tau)_n$, (Formula (13)), and n. $(\Phi)_m(\tau)_n(\Phi)_m$, (Formula (14)), wherein:

($\Phi$) represents independently for each occurrence, a natural or non-natural amino acid comprising a hydrophobic side-chain; preferably alanine, valine, leucine, isoleucine or proline;

(+) represents independently for each occurrence a natural or non-natural amino acid comprising a side-chain that is cationic at physiological pH; preferably histidine, lysine or arginine;

(−) represents independently for each occurrence a natural or non-natural amino acid comprising a side-chain that is anionic at physiological pH; preferably aspartic acid or glutamic acid;

($\tau$) represents independently a polar amino acid containing a non-charged side chain at physiological pH, for example, serine, threonine, asparagine and glutamine;

wherein the terminal amino acids are optionally substituted;

m for each occurrence represents an integer greater than or equal to 5; and n for each occurrence represents an integer greater than or equal to 1;

under conditions suitable for self-assembly of the peptides into a nanostructure and allowing the nanostructure to be formed.

Reading each of the Formulae (1) to (14) from left to right corresponds to the amino acid sequence from the N-terminus to the C-terminus. In other words, the first amino acid in the sequence is the N-terminus and the last amino acid in the sequence is the C-terminus.

In a further embodiment, the N-terminus of the surfactant peptide is blocked, e.g., acylated or acetylated. In an additional embodiment, the C-terminus of the surfactant peptide is blocked, e.g., esterified or amidated. In one aspect, the peptides having the formula 1, 3, 4, 5, 7, 8, or 10 at the N terminal amino acid can be substituted by an acyl (e.g. acetyl or butyloxycarbonyl group) or other blocking group to remove the terminal charge. In another aspect, the peptides having the formula 1, 2, 4, 6, 7, 8, or at the C terminal amino acid can be substituted by an amino or alcohol group to form an amide or ester, or other blocking group to remove the terminal charge. Indeed, one or both termini and any side chains residues can be optionally blocked or further substituted to modify (remove or add) charge, and/or increase or decrease hydrophobicity and/or hydrophilicity of the surfactant. Blocking groups that can be used to control charge, hydrophobicity or the ability to self-assemble in the surfactant include esters and amides of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: N.Y., 1991), which is incorporated by reference.

In a further aspect, the surfactant peptide forms a nanotube or a nanovessicle with a diameter between about 30 to about 50 nm. In an additional embodiment, the peptide surfactant has a critical aggregation concentration in a few μM to millimolar range.

Most preferably, the surfactant peptide is selected from:

| | |
|---|---|
| AAAAAAD, | (SEQ ID NO: 1) |
| VVVVVVD, | (SEQ ID NO: 2) |
| AAAAAADD, | (SEQ ID NO: 3) |
| VVVVVVDD, | (SEQ ID NO: 4) |
| LLLLLLDD, | (SEQ ID NO: 5) |
| KKIIIIII, | (SEQ ID NO: 6) |

| | | |
|---|---|---|
| KKLLLLLL, | (SEQ ID NO: 7) | |
| KKAAAAAAA, | (SEQ ID NO: 8) | |
| KKVVVVVV, | (SEQ ID NO: 9) | |
| DDDDDDDDDDAAAAAAAAAA, | (SEQ ID NO: 10) | |
| AAAAAAAAAADDDDDDDDDD, | (SEQ ID NO: 11) | |
| EEEEEEEEEEAAAAAAAAAA, | (SEQ ID NO: 12) | |
| AAAAAAAAAAEEEEEEEEEE, | (SEQ ID NO: 13) | |
| DDDDDDDDDDVVVVVVVVVV, | (SEQ ID NO: 14) | |
| VVVVVVVVVVDDDDDDDDDD, | (SEQ ID NO: 15) | |
| DDDDDDDDDDPPPPPPPPPP, | (SEQ ID NO: 16) | |
| PPPPPPPPPPDDDDDDDDDD, | (SEQ ID NO: 17) | |
| AAAAAAAAAAHHHHHHHHHH, | (SEQ ID NO: 18) | |
| HHHHHHHHHHAAAAAAAAAA, | (SEQ ID NO: 19) | |
| KKKKKKKKKKAAAAAAAAAA, | (SEQ ID NO: 20) | |
| AAAAAAAAAAKKKKKKKKKK, | (SEQ ID NO: 21) | |
| RRRRRRRRRRAAAAAAAAAA, | (SEQ ID NO: 22) | |
| AAAAAAAAAARRRRRRRRRR, | (SEQ ID NO: 23) | |
| DDDDDDDDDDAAAAAAAAAADDDDDDDDDD, | (SEQ ID NO: 24) | |
| EEEEEEEEEEAAAAAAAAAAEEEEEEEEEE, | (SEQ ID NO: 25) | |
| DDDDDDDDDDVVVVVVVVVVDDDDDDDDDD, | (SEQ ID NO: 26) | |
| DDDDDDDDDDPPPPPPPPPPDDDDDDDDDD, | (SEQ ID NO: 27) | |
| HHHHHHHHHHAAAAAAAAAAHHHHHHHHHH, | (SEQ ID NO: 28) | |
| KKKKKKKKKKAAAAAAAAAAKKKKKKKKKK, | (SEQ ID NO: 29) | |
| RRRRRRRRRRAAAAAAAAAARRRRRRRRRR, | (SEQ ID NO: 30) | |
| AAAAAAAAAADDDDDDDDDDAAAAAAAAAA, | (SEQ ID NO: 31) | |
| AAAAAAAAAAEEEEEEEEEEAAAAAAAAAA, | (SEQ ID NO: 32) | |
| VVVVVVVVVVDDDDDDDDDDVVVVVVVVVV, | (SEQ ID NO: 33) | |
| PPPPPPPPPPDDDDDDDDDDPPPPPPPPPP, | (SEQ ID NO: 34) | |
| AAAAAAAAAAHHHHHHHHHHAAAAAAAAAA, | (SEQ ID NO: 35) | |
| AAAAAAAAAAKKKKKKKKKKAAAAAAAAAA, | (SEQ ID NO: 36) | |
| AAAAAAAAAARRRRRRRRRRAAAAAAAAAA, | (SEQ ID NO: 37) | |
| KKKKKKKKKKAAAAAAAAAADDDDDDDDDD, | (SEQ ID NO: 38) | |
| KKKKKKKKKKAAAAAAAAAAEEEEEEEEEE, | (SEQ ID NO: 39) | |
| RRRRRRRRRRVVVVVVVVVVDDDDDDDDDD, | (SEQ ID NO: 40) | |
| KKKKKKKKKKPPPPPPPPPPDDDDDDDDDD, | (SEQ ID NO: 41) | |
| HHHHHHHHHHAAAAAAAAAAEEEEEEEEEE, and | (SEQ ID NO: 42) | |
| AAAAAAK. | (SEQ ID NO: 47) | |

Each of the above amino acid designations, (e.g., A, D, E, etc.) are intended to include substituted or blocked forms, e.g. N-acetyls or COO-alkyls. Further discussion of surfactant oligopeptides and di- and tri-block peptide copolymers that can be used according to the present invention can be found, for example, in U.S. Pat. No. 7,179,784 and U.S. Pat. Application Publication No. 2009069547, the contents of each of which are hereby incorporated by reference.

In one instance of the invention, G-protein coupled receptor [2] is immobilized on a support [15]. Examples of materials used for supports include any material capable of forming a solid surface, such as, without limitation, gold, silver, platinum, glass, silica, silicon, ceramics, silicon dioxide, plastics, metals (including alloys), naturally-occurring and synthetic polymers (e.g., polystyrene, cellulose, chitosan, dextran, and nylon), and the like. A support [15] may be formed of layers made of a plurality of materials. For example, a support may be made of an inorganic insulating material, such as glass, quartz glass, alumina, sapphire, forsterite, silicon oxide, silicon carbide, silicon nitride, or the like. A support [15] may be made of an organic material, such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile co-polymer, acrylonitrile-butadiene-styrene co-polymer, silicone resin, polyphenylene oxide, polysulfone, and the like. Also in the present invention, nitrocellulose film, nylon film, PVDF membrane, or the like, which are used in blotting, may be used as a material for a support [15]. When a material constituting a support is in the solid phase, such as a support is herein particularly referred to as a "solid phase support". A solid phase support [15] may herein take the form of a plate, a microwell plate, a chip, a glass slide, a film, beads, a metal (surface), or the like. A support may or may not be coated.

The term "coating" in relation to a solid phase support or substrate refers to an act of forming a film of a material on a surface of the solid phase support or substrate, and also refers to a film itself. Coating is performed for various purposes, such as, for example, improving the quality of a solid phase support and substrate (e.g., elongation of life span, improvement in resistance to hostile environment, such as resistance to acids, etc.), affinity to a substance integrated with a solid phase support or substrate, and the like. Various materials may be used for such coating, including, without limitation, biological substances (e.g., DNA, RNA, protein, lipid, etc.), polymers (e.g., poly-L-lysine, MAS (available from Matsunami Glass, Kishiwada, Japan), and hydrophobic fluorine resin), silane (APS (e.g., γ-aminopropyl silane, etc.)), metals (e.g., gold, etc.), in addition to the above-described solid phase support and substrate. The selection of such materials is within the technical scope of those skilled in the art and thus can be performed using techniques well known in the art.

Immobilization of the G-protein coupled receptor [2] onto the support [15] can be achieved by various methods known in the art. The support can comprise a receptor binding surface to which the receptor is attached. One example uses the G-protein coupled receptor [2] attached to the metal oxide nanowires. The G-protein coupled receptor [2] can be bound to the nanowire covalently or non-covalently through the G-protein coupled receptor [2] or through the surfactant or other organic/inorganic intermediates (adapters). Direct attachment (where G-protein coupled receptor [2] directly contacts the metal oxide nanowire surface) and indirect attachment (where intermediate layers are required for attachment) are included. In the context of this invention, methods of attachment of G-protein coupled receptors [2] (such as olfactory receptors) to the metal oxide nanowires include, but are not limited to, covalent chemical coupling, photochemical cross-linking, surface coating/modification, gold surface chemistry, protein affinity tags, biotin-streptavidin linkages, antibody immobilization, and engineered surface-binding peptide sequences. In certain aspects, the olfactory receptor is captured on an antibody covalently attached to the support. In another aspect, the olfactory receptor comprises an oligonucleotide sequence tag that binds non-covalently to the antibody immobilized on the surface. In certain aspects, the oligonucleotide sequence tag can, for example, be a rho1D4 tag as described below.

Another method is the direct attachment of the G-protein coupled receptor [2] on metal oxides using peptide binding sequences. For example, in the case of ZnO nanowires, the G-protein coupled receptor can be directly attached to ZnO nanowires using a ZnO-binding peptide sequence. These binding peptide sequences are obtained by screening a vast combinatorial library of random peptide sequences for binding to the metal oxide surface. To allow binding sequences to be enriched, the peptides are coupled to a biological vector. Some examples are viruses (phage display), cell surface display (using bacteria or yeast), or small biomolecules (ribosomes or antibodies). For a review of these methods, please see Sarikaya et al. (2003) "Molecular biomimetics: nanotechnology through biology" *Nature Materials.* 2(9), 577-585. A typical protocol consists of incubating the peptide library (attached to a biological vector) with the metal oxide surface, then washing the surface thoroughly to remove sequences that bind weakly. Those that bind strongly are then eluted from the surface with a low pH buffer and the population amplified by allowing the vector to multiply. These screened binding sequences can be determined by direct sequencing. The process is repeated with increasingly stringent wash conditions until only one or several binding peptide sequences remain, which will bind the surface with high affinity.

A specific example for such a method is the use of an M13 bacteriophage library (phage display) to generate ZnO nanowire-binding sequences. This protocol has been adapted from Whaley et al. (2000) "Selection of peptides with semiconductor binding specificity for directed nanocrystal assembly" *Nature.* 405, 665-668, the contents of which are incorporated by reference herein. The library contains approximately 1 billion ($10^9$) random peptide sequences expressed on the viral coat which are screened for their ability to bind ZnO nanowires. After washing, the bound phage are eluted (pH 2.2) and amplified by allowing them to infect their bacterial host (*E. Coli* ER2537). After 5-6 successively more stringent rounds of selection an optimal ZnO-binding sequence is determined.

Examples of a ZnO-binding sequence includes, but not limited to, RSNTRMTARQHRSANHKSTQRARS (SEQ ID NO: 43) or a binding fragment thereof, GLHIPTSHR (SEQ ID NO: 44), EAHVMHKVAPRP (SEQ ID NO: 45), and RIGHGRQIRKPL (SEQ ID NO: 46). The coupling can be accomplished synthetically or recombinantly (That C K, et al., *Biotechnol. Bioeng.*, 2004, 87, 129-137, which is hereby incorporated by reference by its entirety).

As used herein the term "nanowire" means a wire (or other filamentous structure) with a diameter scale on the order of nanometers (nm). Growth of nanowires having various aspect ratios, including nanowires with controlled diameters, is described in, e.g., Gudiksen et al. (2000) "Diameter-selective synthesis of semiconductor nanowires" *J. Am. Chem. Soc.* 122, 8801-8802; Cui et al. (2001) "Diameter-controlled synthesis of single-crystal silicon nanowires" *Appl. Phys. Lett.* 78, 2214-2216; Gudiksen et al. (2001) "Synthetic control of the diameter and length of single crystal semiconductor nanowires" *J. Phys. Chem. B* 105, 4062-4064; Morales et al. (1998) "A laser ablation method for the synthesis of crystalline semiconductor nanowires" *Science* 279, 208-211; Duan et al. (2000) "General synthesis of compound semiconductor nanowires" *Adv. Mater.* 12, 298-302; Cui et al. (2000) "Doping and electrical transport in silicon nanowires" *J. Phys. Chem. B* 104, 5213-5216; Peng et al. (2000) "Shape control of CdSe nanocrystals" *Nature* 404, 59-61; Puntes et al. (2001) "Colloidal nanocrystal shape and size control: The case of cobalt" *Science* 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" *J. Am. Chem. Soc.,* 124, 1186; and Yun et al. (2002) "Ferroelectric Properties of Individual Barium Titanate Nanowires Investigated by Scanned Probe Microscopy" *Nanoletters* 2, 447. The nanowires of this invention can be substantially homogeneous in material properties, or in certain embodiments can be heterogeneous (e.g., nanowire heterostructures). The nanowires can be fabricated from essentially any convenient material or materials, and can be, e.g., substantially crystalline, substantially monocrystalline, polycrystalline, or amorphous. It should be appreciated that although nanowires are frequently referred to, nanostructures, such as nanorods, nanotubes, nanotetrapods, nanoribbons and/or combinations thereof can also be employed.

The metal oxide nanowires used in accordance with this invention include, but are not limited to, titanium oxide, zinc oxide, tin oxide, alumina, zirconia, ceria, silica, yttria, boronia, magnesia, strontium titanate, potassium titanate, barium titanate, calcium titanate, calcia, ferrite, hafnia, tungsten trioxide, iron oxide, copper oxide, nickel oxide, cobalt oxide, barium oxide, strontium oxide, vanadium oxide, indium oxide, barium titanate, aluminosilicate, niobium oxide and calcium phosphate. These compounds can be selected depending on the intended use, and may be used singly or in combination. Among these metal oxide nanowires, titanium oxide, zinc oxide, tin oxide, indium oxide and tungsten oxide are most preferable due to the wide energy gaps of 3 eV or wider.

For example, to form GaAs semiconductor nanocrystals, a solution of Ga and As precursors may be prepared by dissolving an organic complex of Ga and As powder into tributyl phosphine. About 2 ml of this solution (kept at $-10°$ C.) may then be quickly injected into about 4 grams of a heated bath comprising a binary mixture of (99% pure) tri-octyl phosphine oxide (TOPO) and 17 molar % hexyl phosphonic acid (HPA) which had been preheated to a temperature of about 360° C. After the injection, the temperature of the binary mixture bath drops to approximately 300° C. and is kept at this temperature for about 5-10 minutes for the fast growth of rod-like GaAs semiconductor nanocrystals. After this time period, the binary mixture bath is rapidly cooled. The same procedure may be used to form spherical semiconductor nanocrystals by reducing the concentration of the HPA down to, for example, about 4 molar % and increasing the reaction time at 300° C. up to several hours. Similar results may be obtained substituting other particular Group III metals (Al or In) for Ga and/or substituting other particular Group v precursors (P or Sb) for As.

To form CdSe semiconductor nanocrystals, a solution of Cd and Se precursors is prepared by dissolving 0.82 grams of $Cd(CH_3)_2$ and 0.4 grams of Se powder into 15.3 grams of tributyl phosphine. 2 ml of this solution (kept at −10° C.) was then quickly injected into 4 grams of a heated bath comprising a binary mixture of (99% pure) tri-octyl phosphine oxide (TOPO) and 17 molar % hexyl phosphonic acid (HPA) which had been preheated to a temperature of about 360° C. After the injection, the temperature of the binary mixture bath drops to approximately 300° C. and is kept at this temperature for about 5-10 minutes for the fast growth of rod-like semiconductor nanocrystals. After this time period, the binary mixture bath is rapidly cooled. The same procedure may be used to form spherical semiconductor nanocrystals by reducing the concentration of the HPA down to, for example, about 4 molar % and increasing the reaction time at 300° C. up to several hours.

To form ZnO nanowires, ZnO powder and graphite powder can be mixed in a weight ratio 1:3 to 3:1 and loaded into a graphite boat, placed into a quartz tube being flushed with Ar gas with a flow rate between 100 and 2000 sccm. The gas can contain between 1 and 10 ppm oxygen. A (100) $SrTiO_3$ single crystal substrate coated with a film of gold with a thickness between 1 and 100 nm can be placed in the tube downstream of the graphite boat where the temperature gradient between the graphite boat and the substrate can be approximately 300° C. The quartz tube can be heated to between 900° C. and 1000° C. for 0.25 to 1 hour to grow the nanowires. Alternatively, zinc metal can be used as the metal vapor source, in which case the tube furnace was heated to between 500° C. and 700° C. The nanowires can be grown on the single crystal surface in a uniform diameter and length, ranging from 10 to 50 nm and 1 to 2 nm, respectively.

In a preferred embodiment, the nanowires can be grown from a ZnO foil. One such protocol that has been used in obtaining functional bio-photovoltaic devices was as follows: A 0.075 M $ZnSO_4$ aqueous solution (40 ml) containing $NH_4Cl$ (molar ratio of $NH^{+4}/Zn^{+2}=20:1$) was formed. The pH was adjusted to 11.7 with NaOH pellets. Pieces of 0.25 cm² Zn foil were suspended in the solution and the vial containing the solution was transferred to a water bath at 60° C. and left overnight for 12-15 h at 60° C. The effects of varying pH were studied showing that at pH 13, the nanowires produced were black in color indicating a lower bandgap. This process requires very little heat and only a small number of steps and does not require the use of harmful chemicals. The varying of the pH levels provides an improvement over the protocol of F. Xu et al. (*Nanotechnology* 17 (2006) 588-594), which is hereby incorporated by reference by its entirety.

In one embodiment, the real time receptor-ligand binding detection method [6] of the bio-sensing nanodevice is selected from Surface Plasmon Resonance (SPR), micro-slot nuclear magnetic resonance (microNMR), scanning tunneling microscopy (STM)/impedance spectroscopy, atomic force microscopy (AFM), ZnO nanowire surface passivation, optical microscopes, confocal microscopes, and reading devices using a laser light source. In a preferred embodiment, the receptor-binding detection method is selected from ultraviolet-visible absorption and fluorescence resonant energy transfer. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jonsson et al. (1993) Ann. Biol. Clin. 51:19; Jonsson et al. (1991) Biotechniques 11:620-627; Johnsson et al. (1995) J. Mol. Recognit. 8:125; and Johnnson et al. (1991) Anal. Biochem. 198:268.

The term "surface passivation" is used to refer to the formation of a protective oxide (preferably ZnO) or nitride layer on the surface of the metallic layer freshly deposited by the process of the invention. Such passivation is produced, without limitation, by a plasma source or ion beam operated in the presence of molecular oxygen and/or nitrogen to produce an activated layer of molecular, ionized and atomic particles that passivate the surface of the metal layer being treated, particularly aluminum, by the formation of superficial oxides and/or nitrides.

Optical sensors for fluorescence or luminescence have the ability to detect emitted light of very low intensity at specific wavelengths and the ability to block light at other wavelengths which can interfere with the signal being detected. Such sensors are often used in conjunction with the application of molecules known as fluorescent probes. Many fluorescent probes have been designed to localize components within a biological specimen or to respond to a specific stimulus. Because of the maturity of fluorescent probe technology, probes can be obtained from many manufacturers, including Invitrogen (Carlsbad, Calif.), Martek Biosciences Corporation (Columbia, Md.), and Sigma-Aldrich Corporation (St. Louis, Mo.). Specific useful probes can indicate a broad set of cellular features and properties such as ion concentration, proteins, nucleic acids, pH, membrane potential, and other characteristics known to those skilled in the art.

Fluorescence sensing systems typically have at least four components: (1) a light source; (2) optical filters; (3) detectors (i.e., light sensors); and (4) signal processing circuitry. The light source is designed to deliver sufficient optical power, the filters to be capable of discriminating wavelengths, and the detectors to distinguish fluorescent emission, even in the presence of interfering excitation light. The cell must be illuminated within an appropriate range of wavelengths in order for the fluorescence to occur. This "excitation" light can be generated by a separate component integrated with the system such as a vertical-cavity surface-emitting laser (VCSEL) or a light emitting diode (LED) or by a semiconductor photon source integrated on-chip. The light can be directly shone on the cells or guided to the cells using an optical waveguide integrated on-chip.

Optical sensors for imaging the cells have the ability to measure light intensity using a dense array of photosensitive pixels. For the purposes of this invention, such sensors can be used in either a conventional imaging configuration with optical elements such as lenses that focus the image onto an imaging array as in a standard camera or light microscope, or in a "contact" imaging configuration which does not use intervening optics and which generates a representation of a specimen directly coupled to the surface of the chip. The photosensitive elements of the contact imager capture light that is transmitted through the cells. Preferably, imagers are compatible with CMOS technology to enable the implementation of other sensors and circuitry on the same substrate. Many pixel designs are suitable for imagers and are well known in the field of digital imaging technology, including passive pixels, current-mode pixels, and active pixel sensor (APS) pixels.

As used herein, the term "real time" means that a certain state is substantially simultaneously displayed in another form (e.g., as an image on a display or a graph with processed data). In such a case, the "real time" lags behind an actual event by the time required for data processing. Such a time lag is included in the scope of "real time" if it is substantially negligible. Such a time lag may be typically within 10 seconds, and preferably within 1 second, without limitation. A time lag exceeding 10 seconds may be included in the scope of "real time" for certain uses.

In one embodiment, the odorant delivery system [5] of the bio-sensing nanodevice can be either passive exposure to air or microfluidic bubble logic operation. The microfluidic bubble logic operation comprises micron-sized droplets and bubbles of chemical in a microfluidic chip [11]. Control of routing of packets of gas bubbles in a microfluidic chip [11] allows for implementation of complex detection schemes. The term "bubble logic" employs micron-sized (nanoliters) droplets and bubbles of chemicals to mimic the actions of the electrons moving through the circuits of a microprocessor. Thus bubbles traveling in a microfluidic channel can carry a variety of gas samples to precise locations on a chip [11]. They can be stored in memory elements, routed on-chip, merged or split and transported at high throughputs. The term "microfluidic" generally refers to a system or device having channels and chambers that are fabricated with a cross-sectional dimension (e.g. depth, width, or diameter) of less than a millimeter. The channels and chambers typically form fluid channel networks that allow the transportation, mixing, separation and detection of very small quantities of materials. Microfluidics are particularly advantageous because they make it possible to perform various chemical and biochemical reactions, macromolecular separations, and the like with small sample sizes, in automatable, high-throughput processes. Microfluidic systems are particularly well adapted for analyzing small sample sizes. Sample sizes are typically are on the order of nanoliters and even picoliters. Similar apparatus and methods of fabricating microfluidic devices are also taught and disclosed in U.S. Pat. Nos. 5,858,195; 5,126,022; 4,891,120; 4,908,112; 5,750,015; 5,580,523; 5,571,410; 5,885,470; and 6,793,753 incorporated herein by reference.

Microfluidic devices can be fabricated out of any material that has the necessary characteristics of chemical compatibility and mechanical strength. One exemplary material is silicon since a wide range of advanced microfabrication and micromachining techniques have been developed for it and are well known in the art. Additionally, microfluidic devices can be produced directly in electrically insulating materials. The most widely used processes include isotropic wet chemical etching of glass or silica and molding of plastics. The channels are typically defined by photolithographic techniques and etching away the material from around the channel walls produces a freestanding thin walled channel structure. Freestanding structures can be made to have very thin or very thick walls in relation to the channel width and height. The walls, as well as the top and bottom of a channel can all be of different thickness and can be made of the same material or of different materials or a combination of materials such as a combination of glass, silicon, and a biologically-compatible material such as PDMS. Sealed channels or chambers can be made entirely from biologically-compatible material such as PDMS.

In one embodiment, the odorant recognition program [7] of the bio-sensing nanodevice comprises a 1 dimensional peak-recognition program. For instance, the system is first "trained" on known odorants and the signatures are recorded. Then the system is exposed to unknown odorants or combinations of odorants and the signatures are matched with the known database of odors. Thus, the products and methods of the inventions can be used in a number of commercially interesting areas. For example, the devices can detect the presence, absence or quality of specific odoriferous chemical compounds or biological substances (including bacteria, mold, mildew, fungi, and viruses). It can be used to detect the presence of illegal substances or controlled substances (e.g., in an airport, customs or similarly controlled environment). It can be used to detect pathogens or toxins, such as in an air quality management program in a residential, industrial or other working or living environment. It can be used to detect contaminants in products, such as food, drugs, medical devices, sterile products, and the like. It can be used to determine the quality or acceptability of food products, drugs, consumer products and perfumes. It can be used in medical fields and diagnostics by detecting human odors, including the breath or other body odors. It can be used to detect, identify or locate materials, including chemicals, tissues and the like, such as in industrial, medical and forensics applications. In another embodiment, application software for measurement and presentation typically includes software for setting conditions for applying stimuli or conditions for recording detected signals. With such a measurement and presentation application, a computer can have a means for applying a stimulus to cells and a means for processing signals detected from cells, and in addition, can control an optically observing means (a SIT camera and an image filing device) and/or a cell culturing means. As such, the invention can include a computer processing unit which is programmed to identify a test composition's "fingerprint" (e.g., the specific combination of receptors that are activated and/or not activated) and compare it to one or more standards (e.g., the specific combination of receptors that are activated and/or not activated) and identify the exact match or close match(es).

Real time display can also be performed using techniques well known in the art. For example, after all images are obtained and stored in a semi-permanent memory, or substantially at the same time as when an image is obtained, the image can be processed with appropriate application software to obtain processed data. For example, data may be processed by a method for playing back a sequence of images without interruption, a method for displaying images in real time, or a method for displaying images as a "movie" or "streaming" showing irradiating light as changes or continuation on a focal plane. By inputting stimulus variables on a parameter setting screen using a keyboard, a touch panel, a mouse, or the like, it is possible to set desired complicated conditions for stimulation. In addition, various conditions, such as a temperature for cell culture, pH, and the like, can be set using a keyboard, a mouse, or the like. A display screen displays a time-lapse profile detected from a cell or information derived therefrom in real time or after recording. In addition, another recorded profile or information derived from of a cell can be displayed while being superimposed with a microscopic image of the cell. In addition to recorded information, measurement parameters in recording (stimulation conditions, recording conditions, display conditions, process conditions, various conditions for cells, temperature, pH, etc.) can be displayed in real time. The present invention may be equipped with a function of issuing an alarm when a temperature or pH departs from the tolerable range.

On a data analysis screen, it is possible to set conditions for various mathematical analyses, such as Fourier transformation, cluster analysis, FFT analysis, coherence analysis, correlation analysis, and the like. The present invention may be equipped with a function of temporarily displaying a profile, a function of displaying topography, or the like. The results of these analyses can be displayed while being superimposed with microscopic images stored in a recording medium.

In an embodiment, in the sensor of the present invention, the d) means for providing information comprises d-1) signal processing member for using a stimulus species categorizing method based on the stimulus element tuning specificity of a cell having a chemical receptor to add a first signal output by predetermined plurality of said sensors, to calculate a value of sensory elemental information expressing a sensation, and outputting a calculation result as a second signal; and d-2) evaluation member for effecting qualitative and/or quantitative evaluation using the second signal output by the signal processing member. Such means for providing information is described herein in detail elsewhere in the specification, and is enabled. It is currently possible to conduct quantitative or qualitative evaluation which was not achievable by the conventional methods, by conducting such information analysis. Preferably, the stimulus species categorizing method used in the aforesaid means for providing information advantageously uses classification according to the species of the chemical receptor. Classification allows more detailed or specific analysis.

In an embodiment, the signal processing member reduces as used in the present sensor, when one of first signals output by the plurality of sensors exceeds a predetermined value, the first signal output by a sensor different from the sensor and uses the reduced signal for producing the second signal. Such analysis allows more detailed analysis.

In another embodiment, the signal processing member used in the sensor of the present invention comprises: a plurality of selection members and addition members corresponding to sensory elemental information; a plurality of amplification members corresponding to each of the sensors; a coefficient calculation member for controlling the amplification member, wherein the selection members multiplies a plurality of the first signal with the coefficient designated by each of the sensors to produce a plurality of third signals; the addition members add the plurality of third signals output by the corresponding selection member to produce a plurality of fourth signal; the coefficient calculation member detects the maximum value among the plurality of fourth signals and normalizes each of the fourth signals using the maximum value to calculate control signals; the amplification members use the corresponding control signals to produce the second signals corresponding to the intensity of sensory elemental information. Such a step allows normalization of signals for presenting analyzed data such that subsequent analysis can be simplified.

In another embodiment, in the sensor of the present invention, when a stimulus such as a chemical including gustatory source, olfactory source and the like, is presented, the first signal output by the sensor, is transiently produced directed to a predetermined value corresponding to the intensity or concentration of the stimulus from zero level, wherein the zero level is set as a status where no response is found in response to no stimuli; the third signal is transiently produced associated therewith directing to a predetermined value corresponding to the intensity or concentration of a stimulus from zero level: the coefficient calculation member determines a sensor response starting at base time when one of the first signals is determined to be the signal output in response to a stimulus by the sensor for the first time, and calculates at a predetermined time as an elapsed time from the base time, the control signal for controlling the amplification member using the third signal at the predetermined time; controls the amplification member using the control signal which was calculated at the last time until a control signal is calculated at the predetermined time. Such a step allows more detailed analysis.

In another embodiment, in the present invention, when a stimulus such as olfactory sources and the like, is presented, the first signal output by the sensor, is transiently produced directed to predetermined value corresponding to the intensity or concentration of the stimulus from zero level, wherein the zero level is set as a status where no response is found in response to no stimuli; the third signal is transiently produced associated therewith directing to a predetermined value corresponding to the intensity or concentration of a stimulus from zero level; the coefficient calculation member determines a sensor response starting at base time when one of the first signals is determined to be the signal output in response to a stimulus by the sensor for the first time; during a period of time when the predetermined number of the plurality of third signals change from augmentation to reduction, and calculates, at each time when the third signal is determined to start occurring significant output as a corresponding sense element, and when the third signal is determined to have achieved a plurality of boundary values which divide the section between the significant output value and the maximum value preset to the third signal into a plurality of segments; controls the amplification member using the control signal which was calculated for the last time until the control signal is calculated. Such a step allows representation of more detailed analysis in a normalized manner.

In a further embodiment, a microfluidic chip [11] for use in detecting odorant comprising a stabilized G-protein coupled receptor immobilized on a support, and arranged in at least two dimensional microarray system is provided. In one embodiment, the microfluidic chip can be disposable or non-disposable. A non-disposable microfluidic chip [11] can be obtained by making the G-protein coupled receptor in situ and on demand from oligonucleotide sequences. The microwell chip is regenerated by microfluidic channels after each reading either by washing each well and/or apply fresh G-protein coupled receptor for binding. The term "array" refers to a substrate (e.g., a chip, etc.) which has a pattern of composition containing at least one (e.g., 1000 or more, etc.) target substances (e.g., DNA, proteins, transfection mixtures, etc.), which are arrayed. Among arrays, patterned substrates having a small size (e.g., 10×10 mm, etc.) are particularly referred to as microarrays. The terms "microarray" and "array" are used interchangeably. Therefore, a patterned substrate having a larger size than that which is described above may be referred to as a microarray. For example, an array comprises a set of desired transfection mixtures fixed to a solid phase surface or a film thereof. In a preferred embodiment the number of sensors and size of the two dimensional microarray system of the microfluidic chip [11] is selected from:

| total # of sensors | dimensions (mm) |
|---|---|
| 36 | 4 × 4 |
| 100 | 6 × 6 |
| 400 | 11 × 11 |
| 900 | 16 × 16 |

As used herein, the terms "chip" or "microchip" are used interchangeably to refer to a micro integrated circuit which has versatile functions and constitutes a portion of a system. Examples of a chip include, but are not limited to, DNA chips, protein chips, and the like. Chips may comprise tubing for supplying a solution. Such tubing may be made of any material as long as no adverse effect is given to the substance of interest in a sample of interest. When administering the stimulus as a solution, a flow rate may be about 1-4 mm/second, preferably about 2.5 mm/second so that cells are not affected by mechanical stimulation by hydraulic pressure, and the entire cell can receive the stimulus in a short period of time. When administering a stimulus in a gaseous form, a gas of interest is introduced into the center of the sensor in an array format. Such a method may be any known method in the art. As an example, the sensor member is enclosed, the exhaust pump is subjected to a weak negative pressure by connecting thereto, the opening of a tubing for introducing a gas of interest from outside is fixed to the vicinity of the sensor member, and when introducing a gas into a solution in which a cell is soaked, in order that a physical fluctuation arisen by wind to the water interface, does not give effects on a signal of interest, the liquid interface is maintained at place by subjecting glass cover onto the site of measure on a sensor array. The introduced gas may be equally distributed onto the sensor member by spraying the gas above the cell in a solution having no odor which soaks the cell and flows at a determined flow rate. Further, in another embodiment, it is possible that no glass cover is arranged onto the above of the sensor member and the introduced gas is directly subjected to the sensor array at a flow rate so that signals have no effects of water interface fluctuation by wind. In this instance, the water depth of the sensor member is about 1-2 mm and the sensor member may be in a condition where a solution should not repel from the sensor member by subjecting stimulus hydrophobic components to the sensor member. In order to maintain the cleanliness in the vicinity of a cell, twenty to thirty seconds after the measurement, it may be necessary to replace the solution in the vicinity with a solution without the chemical of interest.

In a further embodiment, a method of manipulating of the bubbles in complex microfluidic networks, wherein the bubbles travel in a microfluidic channel carrying a variety of gas samples to a precise location on a chip, thereby improving sensitivity and precision in odorant detection is provided.

Yet in another embodiment, a method of fabricating an olfactory receptor using expression system selected from cell-free, bacterial, fungal and mammalian expression systems is provided. In certain aspects, the fabricated olfactory receptor is used in a device according to the present invention. In one embodiment, the olfactory receptor is selected from the group consisting of OR17-4, OR23 and S51. In a further embodiment, the olfactory receptor is hOR17-4. In some embodiments, the method comprises expressing an olfactory receptor using an expression system followed by purifying the olfactory receptor. The term "cell" is herein used in its broadest sense in the art, referring to a structural unit of tissue of a multicellular organism, which is capable of self replicating, has genetic information and a mechanism for expressing it, and is surrounded by a membrane structure which isolates the cell from the outside. In one embodiment, cells used herein may be either naturally-occurring cells or artificially modified cells (e.g., fusion cells, genetically modified cells, etc.). Examples of cell sources include, but are not limited to, a single-cell culture; the embryo, blood, or body tissue of normally-grown transgenic animals; a mixture of cells derived from normally-grown cell lines; and the like. Preferably, a cell which is easily transformed or transfected is used. Cells used in the present invention are preferably cells which are easily cultured and/or maintained on a support and/or cultured in suspension.

Cells used herein may be derived from any organism (e.g., any unicellular organisms (e.g., bacteria and yeast) or any multicellular organisms (e.g., animals (e.g., vertebrates and invertebrates), plants (e.g., monocotyledons and dicotyledons, etc.)). For example, cells used herein are derived from a vertebrate (e.g., Myxiniformes, Petronyzoniformes, Chondrichthyes, Osteichthyes, amphibian, reptilian, avian, mammalian, etc.), mammalian (e.g., monotremata, marsupialia, edentate, dermoptera, chiroptera, carnivore, insectivore, proboscidea, perissodactyla, artiodactyla, tubulidentata, pholidota, sirenia, cetacean, primates, rodentia, lagomorpha, etc.). In one embodiment, cells derived from Primates (e.g., chimpanzee, Japanese monkey, human) are used. Particularly, without limitation, cells derived from a human are used. The above-described cells may be either stem cells or somatic cells. Also, the cells may be adherent cells, suspended cells, tissue forming cells, and mixtures thereof. The cells may be used for transplantation.

In one embodiment, the fungal expression system is a yeast expression system. In another embodiment, the yeast expression system is *Pichia pastoris*. In another embodiment, the expression system is a mammalian cell expression system. In some embodiments, the mammalian cell expression system is selected from the group consisting of HEK293 (HEK293S), CHO, COS-7, neuroblastoma, NG108-15 and the like. In further embodiment, the mammalian expression system is HE293S expression system. In a further embodiment, the olfactory receptor is purified from an adherent culture. In yet another embodiment, the olfactory receptor is purified from a suspension culture. In additional embodiments, the olfactory receptor is purified from a suspension culture in a bioreactor. Scale-up production using a bioreactor has been described for bovine rhodopsin has been described, for example, in Chelikani et al. (2006). The synthesis and high-level expression of a B2-adrenergic receptor gene in a tetracycline inducible stable mammalian cell line. Protein Sci. 15: 1433-1440, the contents of which are incorporated by reference herein.

In a further embodiment, the expression system is a cell-free expression system. In certain aspects, the cell-free expression system is an extract from a source selected from the group consisting of rabbit, insect, wheat germ and bacteria. Using such extracts can be advantageous because the extracts contain the necessary components from transcription and translation without the cell membranes. In some embodiments, the cell free expression system is a bacterial extract. In one embodiment, the bacterial extract is an *E. coli* extract. In yet another embodiment, the cell free expression system is a wheat germ extract. The olfactory receptor can be cloned into a suitable vector such as pVEX1.3 and pVEX1.4 with an optional tag (such as, a histidine tag). In one embodiment, the olfactory receptor is cloned into a pVEX1.3 vector. As will be understood by the skilled artisan, a detergent can be used to solubilize the olfactory receptor. In some embodiments, the detergent is selected from the group consisting of Brij-58Foscholine 14 (FC14), Tri-mix and digitonin. In one embodiment, the detergent for solubilizing olfactory receptor in a cell free system is digitonin.

Purification of the olfactory receptor from the expression system can comprise immunoaffinity purification, chromatography or a combination thereof. The purification can comprise immunoaffinity purification, for example, capturing the protein on antibody-coated beads (for example, anti-rhodopsin antibody coated beads). An example of immunoaffinity purification comprises the use of a rho1D4-tag and rho1D4 antibody coated beads as described, for example, in Tekayama et al. (2008). High-level expression single-step immunoaffinity purification and characterization of human tetraspanin membrane protein CD81. PLoS ONE 3: e2314; Reeves et al. (1996). Structure and function in rhodopsin: high level expression of a synthetic bovine opsin gene and its mutants in stable mammalian cell lines. PNAS 93: 11487-11492; Reeves et al. (2002). Structure and function in rhodopsin: a tetracycline-inducible system in stable mammalian cell lines for high level expression of opsin mutants. PNAS 99: 13413-13418, the contents of each of which are expressly incorporated by reference herein. In some embodiments, the olfactory receptor is purified from a mammalian expression system comprising immunoaffinity purification followed by size exclusion chromatography.

In one embodiment, the protein expressed from a cell-free system is purified by immunoaffinity followed by exchange into a buffer comprising a suitable detergent. In some embodiments, the detergent is selected from the group consisting of Anzergent3-14, Brij58 and FC14. In another embodiment, the detergent is FC14.

As described above, the method of fabricating an olfactory receptor comprises purifying the olfactory receptor from the expression system. When a cell expression system is utilized, the protein can be solubilized from the cell membrane. Any suitable detergent can be used to solubilize the protein. In one embodiment, the method of fabricating an olfactory receptor comprises expressing the receptor in an inducible mammalian cell followed by solubilization with a detergent followed by purification of the receptor. In certain aspects, the detergent is a Fos-choline detergent. In another embodiment, the detergent is Fos-choline 14 (FC-14). In some embodiments, the method of fabricating the olfactory receptor comprises expressing the receptor in HEK293 S cells, solubilizing the receptor using a suitable detergent and purifying the receptor, wherein the purification comprises immunoaffinity purification followed by size-exclusion chromatography.

Another embodiment includes a substrate with a cell located thereon, the cell having the nucleic acid molecule introduced (for example, by transformation, transduction, transfection and the like) therein, may be prepared by fixing the cell with the nucleic acid molecule introduced therein to a substrate, or introducing (for example, by transformation, transduction, transfection and the like) the nucleic acid molecule to a cell after the cell is fixed to a substrate. Cell as used herein may be any cell as long as the cell may express a nucleic acid introduced therein. Preferably, cells that can be easily maintained on a substrate are desirable. Such a cell may include, but is not limited to, for example, HEK293 (HEK293S), CHO, COS-7, neuroblastoma, NG108-15 and the like. Any substrate may be used with any material or form, as long as the substrate can be used as a sensor of the present invention. Preferably, the material is advantageously biocompatible. The sensor of the present invention uses a mechanism using expression sustaining biological activity of a chemical receptor in a cell, and therefore the survival of the cell is preferable. Accordingly, when no biocompatible material is used, it may be desirable to coat such a material with a biocompatible material. Preferable form may be for example, quadrangle such as square, as this form is amenable for normalization.

An embodiment of the invention incorporating the specified improvements will have the olfactory receptor binding surface and support comprising a dielectric/metal/dielectric sandwich structure. A laser light source will be irradiated across the metal layer on a horizontal plane, preferably via light fiber. The refractive indexes of the top and bottom dielectrics may have to be adjusted in order to maximize LR-SPP generation. With existing structures, when an adsorption layer was formed under the metal surface, Plasmon could not be generated due to high propagation losses. As a result of the improved structure and the light being applied horizontally, Plasmon can be generated on both sides of the metal layer, providing for more accurate detection and measurement inputs.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Protocols:

A) Fabrication (Purification) and Stabilization/Regeneration of ORs i) Expressing protein in bulk: Human embryonic kidney cell, E-coli and cell-free expression systems (CFES) for the expression and purification of large quantities of the human OR17-4 receptor have been studied. Protocols for expression, stabilization, solubilization, functional assays, binding/adsorption to a variety of surfaces, spectroscopic assays etc. have been developed that aim at the mass-production of this receptor. These protocols can be modified to fit other receptors.

This technology can be used to make disposable micro-well chips where each well contains a different smell receptor. Once the chip has been exposed to the gas/air of interest it is read and discarded.

ii) Making the smell receptors in situ and on demand from oligonucleotide sequences is another way to operate the smell sensor. In this case, the micro-well chip is not disposable but rather is regenerated by microfluidic channels after each reading either by washing each well and/or applying fresh smell receptors for binding. Preliminary experiments have been done expressing human olfactory receptors in-situ using a CFES kit as well as expressing GFP that has been shown to be functional upon microfluidic assisted expression.

Example 1

Production of Human Smell Receptor in Cell Free Expression System

Genes coding for human smell receptor 17-4 (hOR17-4) and production constructs for expression in cell-free systems, bacteria (*E. coli*) and yeast have been molecular engineered using a high-cycle number PCR-based method of gene synthesis. This method has also enabled us to achieve optimal codon usage in the different production systems.

One advantage of using a cell free system for production of membrane proteins is that surfactants can be present during translation and folding of the protein. By using the constructs mentioned above, the optimal surfactant and surfactant concentration for production of soluble receptor has been identified. Interestingly the addition of a stabilizing peptide surfactants developed in our lab significantly enhanced production levels at least five fold. The receptor has been partially purified using affinity purification, based on a tag engineered to the N-terminal of the protein, and subsequently by size exclusion chromatography. The production is currently being scaled up and should result in enough receptor to start crystallisation trials and prototype sensing nanodevice chip fabrication.

It is known that production of membrane proteins in *E. coli* can result in membrane insertion or formation of inclusion bodies containing unfolded protein. To efficiently monitor expression yield and membrane insertion in vivo has green fluorescent protein (GFP) been fused to the C-terminal of the receptor, as GFP only emits green color when correctly folded, namely, not in inclusion bodies. The production of the smell receptor was optimized for signal sequence, culturing time, temperature and media. During the optimization phase, we successfully increased the production yield of membrane inserted smell receptor up to 4 mg/L culture, a very good yield for such system.

Therefore the fluorescence from the smell receptor-GFP fusion has also been used for identifying a suitable surfactant for solubilization of the protein from the membrane. Foscholine-14 (FC-14) is currently the most effective surfactant tested, it can solubilize up to ~95% of the receptor. In addition, using a microscope equipped with the correct filters we have been able to localize the expressed smell receptors to the cell membrane.

Example 2

Large Scale Production of Smell Receptor in Yeast

*Pichia pastoris* as Expression System

The methylotrophic yeast *Pichia pastoris* has been used for many years for producing a wide range of recombinant proteins. This *Pichia pastoris* production system has a highly inducible promoter (methanol). Genomic integration of the production cassette has the advantage that the production vector will not be lost on induction. Yeast *Pichia pastoris* is particularly efficient, it grows rapidly, reaches high cell densities, does not make hyperglycosylation and possesses extremely efficient secretory machinery. Several similar receptors to smell receptors have been functionally produced in *Pichia pastoris*. Expression levels vary from 0.4-100 pmol/mg membrane proteins.

Production of Smell Receptor in *Pichia pastoris*

Our results showed that we could successfully produce the smell receptor hOR17-4 in *Pichia pastoris*. This is the first time, to our knowledge, that a smell receptor has been expressed in *Pichia pastoris*. We used 2 different vectors (Invitrogen, CA): pPICZ (with a signal sequence) and pPICZ (without signal sequence). Three different *Pichia pastoris* strains, X-33, KM71H and GS115, were transformed with both vectors respectively, resulting in six different clones containing the construct with an N-terminal His-tag for affinity purifications. Six different *Pichia pastoris* clones produced the smell receptor as detected by immunoblotting. Interestingly the wild type *Pichia pastoris* strain X-33, which produced the receptor with a signal sequence (for targeting to the membrane) showed the highest production level. Optimization of the production by varying production conditions (e.g. induction time, induction temperature, methanol concentration, medium) made an additional 2-fold increase. Synergistic effects are under investigation. The production level of the smell receptor is ~50 pmol/mg membrane protein. This is a high yield compared to production of similar proteins in *Pichia pastoris* (0.4-100 pmol/mg). As *Pichia pastoris* has been developed into a highly successful system for the large-scale production of recombinant proteins, production of large quantities of smell receptors is highly feasible.

Example 3

Large-Scale Mammalian Cell Line Production of Smell Receptors

Optimization of the extraction procedure for smell receptors transiently produced in the mammalian cell line HEK293S. The research was focused on several areas in order to enable the mass production of smell receptors. First, we engineered and constructed new producer cell lines in which production of the smell receptor can be directly controlled (a so called "inducible" system). This allows large-scale cell culture batches to be grown and then, when desired, concerted production of fresh smell receptor to be induced in 100% of the cells, with minimal toxicity.

Figure 2A:
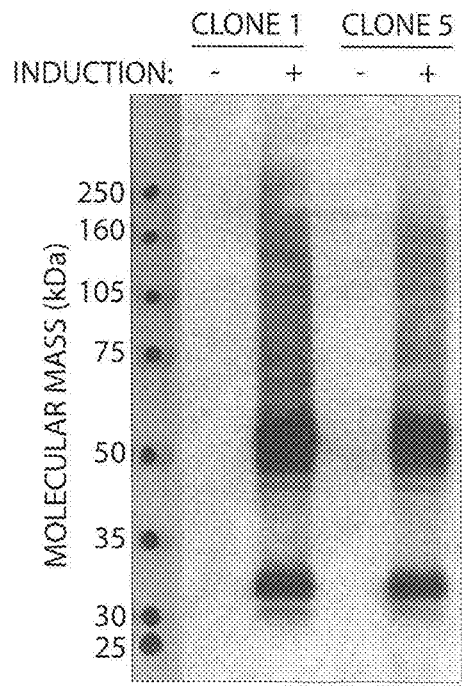
FIG. 2: (a) Western blot of smell receptor purifications. There are two cell line clones, 1 and 5. – indicates no induction, + indicates inductions with tetracyclin/NaBu. The monomers and dimmers in both clones are clearly seen. The molecular size markers are on the left lane. (b) Inductions time with different concentration and combinations of tetracyclin/NaBu. The results clearly showed that 5 mM NaBu significantly enhanced the smell receptor production.
Figure 2B:
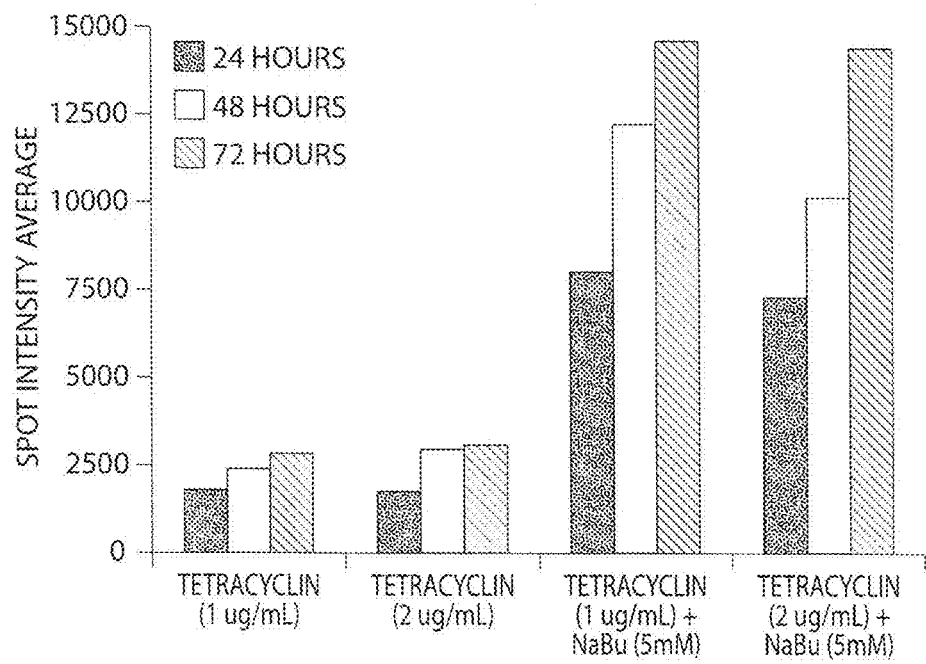

To obtain the highest amount of smell receptors, we have also optimized the induction protocol for each cell line generated with respect to time, concentration of inducer (tetracycline), and addition of a synergistic enhancer (sodium butyrate=NaBu). The results of the optimization are shown in FIG. 2.

Figure 3:
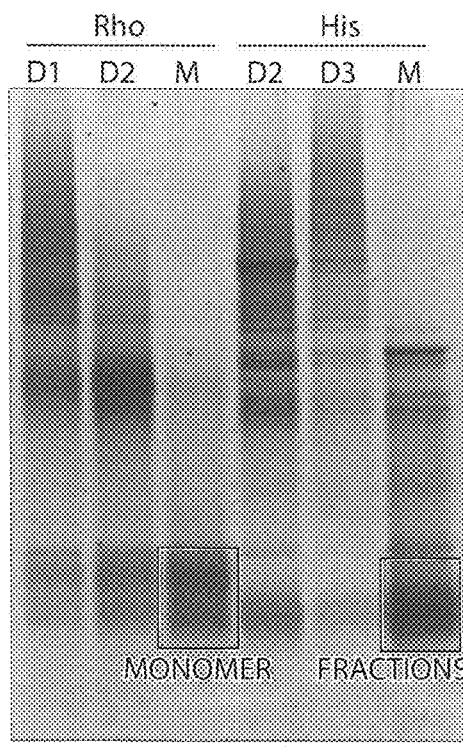
FIG. 3 illustrates smell receptor purification and examines its purity using gel electrophoresis. Two different purification Tags were used. Both Tags work well. M denotes monomer receptor, D denote dimmer protein fractions.

Using this protocol, we carried out a medium-scale purification trial on two versions of the smell receptor hOR17-4. The first version (hOR17-4-Rho) uses the "Rho" affinity tag at the C-terminus of the protein while the second (HF-hOR17-4) uses the "His" affinity tag at the N-terminus. Each smell receptor version was separately extracted, solubilized and purified using affinity-based chromatography. Additionally, we have now incorporated the use of a second purification step, gel filtration chromatography, to further polish the final product to a highly pure monomeric form (see FIG. 3). Using this method we successfully purified 0.13 mg of hOR17-4-Rho to >90% purity and 0.39 mg of HF-hOR17-4 to >70% purity.

We have begun using purified smell receptors for crystallization, a necessary step to obtaining high-resolution structural data using X-ray crystallography. Additionally, we have used this purified smell receptor in newly devised experiments testing for stability, functionality and odorant binding (Examples 11-13). These experiments rely on fluorescence spectroscopy, Circular Dichroism, Biacore (also called Surface Plasmon Resonance), and single-molecule microscopy.

In order to complete our scale-up operation, we have converted the system over from adherent culture plates to a large volume (5-10 liter) liquid bioreactor (Example 12).

Fabrication (Purification) and Stabilization/Regeneration of ORs i) Expressing protein in bulk: Human embryonic kidney cell, E-coli and cell-free expression systems (CFES) for the expression and purification of large quantities of the human OR17-4 receptor have been studied. Protocols for expression, stabilization, solubilization, functional assays, binding/adsorption to a variety of surfaces, spectroscopic assays etc. have been developed that aim at the mass-production of this receptor. These protocols can be modified to fit other receptors.

This technology can be used to make disposable micro-well chips where each well contains a different smell receptor. Once the chip has been exposed to the gas/air of interest it is read and discarded.

ii) Making the smell receptors in situ and on demand from oligonucleotide sequences is another way to operate the smell sensor. In this case, the micro-well chip is not disposable but rather is regenerated by microfluidic channels after each reading either by washing each well and/or applying fresh smell receptors for binding. Preliminary experiments have been done expressing human olfactory receptors in-situ using a CFES kit as well as expressing GFP that has been shown to be functional upon microfluidic assisted expression.

Smell Receptor Gene Fabrication

To adapt the olfactory receptor genes (such as hOR17-4) for use in mammalian cell expression and purification, the following sequence modifications were made using the DNA-Works3.0 software (http://helixweb.nih.gov/dnaworks):

i. Human codon optimization;

ii. Addition of C-terminal rho1D4 epitope tag "TETSQVAPA" (SEQ ID NO: 50) (preceded by a two glycine linker) to facilitate purification;

iii. Addition of NotI restriction site at 3' end of gene;

iv. Addition of EcoRI restriction site and Kozak sequence (GCCACCACC (SEQ ID NO: 53)) at 5' end of gene.

The designed oligos were purchased from IDT (Coralville, Iowa) with a maximum length of 45 bp. The assembly PCR was run for 45 cycles (much higher than the normal 25-30 cycles, the key for our success) using a mixture of all oligo DNA at a concentration of 25 nM each. The amplification PCR was run for 30 cycles using 1 μl of the assembly PCR (in a total reaction volume of 50 μl) and each end oligo at a concentration of 300 nM each. PCR reactions were then analyzed by gel electrophoresis and stained with ethidium bromide. Full-length product was exised, extracted, and then digested with the pertinent restriction enzymes. The genes were then ligated into the T-REx pcDNA4/To inducible expression plasmid (Invitrogen, Carlsbad, Calif.), sequenced, and a correct clones grown up using a MaxiPrep kit (Qiagen, Valencia, Calif.). The plasmid containing the optimized hOR17-4 gene was designated pcDNA4/To-hOR17-4rho.

Inducible Cell Line Generation

HEK293S (suspension adapted HEK293 cells) containing the stable expression of pcDNA6/Tr (Invitrogen), which encodes the Tet repressor protein (TetR) had previously been generated and cloned. The pcDNA4/To-hOR17-4rho plasmid was then transfected into these cells using Lipofectamine 2000 (Invitrogen) and after 48 hours cells were subjected to drug selection in 5 μg/ml blasticidin and 250 μg/ml zeocin for 2 weeks and then subcloned. Colonies were expanded and screened for inducible expression using tetracycline (1 μg/ml) alone as well as tetracycline plus sodium butyrate (5 mM, from Sigma) for 48 hours. Samples were then scrape harvested, solubilized in phosphate buffered saline (PBS) with 2% w/v Fos-Choline-14 (Anatrace, Maumee, Ohio) and Complete Protease Inhibitor Cocktail (Roche, Basel, CH) for 1 hour at 4° C. Expression was assayed via dot blotting and SDS-PAGE western blotting using the mouse monoclonal antibody 1D4. The colony showing the best expression of hOR17-4rho under induction conditions while maintaining undetectable expression without induction was chosen and expanded into large-scale culture. The hOR17-4rho inducible line was designated HEK293S rho5 and were maintained 5 μg/ml blasticidin and 250 μg/ml zeocin.

Smell Receptor Protein Purification

For initial small-scale experiments, 150 mm tissue culture plates were used per condition. Briefly, HEK293S rho5 cells were seeded at a density of 5×10$^6$ cells per 150 mm dish and grown for 72 hours at 37° C., at which point they reached 80-90% confluency. The cells were then induced with medium containing tetracycline (1 μg/ml) plus sodium butyrate (5 mM). After 24-40 hours, the cells were harvested by scraping (at 4° C.) each plate into 2 ml PBS containing Complete Protease Inhibitor Cocktail. The cells were then snap frozen in liquid nitrogen and stored at −80° C. until purification was carried out.

For purification, cells were thawed on wet ice and spun down by centrifugation at 2000 rpm for 1 minute. All further steps were performed at 4° C. unless noted. The membrane proteins were then solubilized by resuspending the cells (1-2 ml per 150 mm plate) in PBS with 2% w/v Fos-Choline-14 and Complete Protease Inhibitor Cocktail and rotating for 4 hours. The non-solubilized fraction was then pelleted using an ultracentrifuge at >100,000 g for 30 minutes. The resulting supernatant was removed and stored at 4° C. A small amount of supernatent (100 μl) was set aside, labeled "total lysate" and stored at −20° C.

For immunoaffinity purification, the remaining supernatant was then mixed with 1D4-coupled sepharose bead slurry (50 uL per 150 mm plate) and rotated overnight to capture the tagged olfactory receptors. The beads were then pelleted by centrifugation at 2000 rpm for one minute and the supernatant collected, labeled as "flow-through" and stored at −20° C. The beads were then washed five times with 100× bead volume with wash buffer (PBS+0.2% Fos-Choline-14), and 100 μl of each sequential wash was saved, labeled, and stored at −20° C. After the final wash, the beads were pelleted again and transferred to a new tube for elution. Five 1-hour elutions were then carried out, each using 1× bead volume elution buffer (PBS+0.2% DM+100 μM TETSQVAPA (SEQ ID NO: 50) peptide), and each elution fraction was in turn labeled and stored at −20° C.

For further purification, hOR17-4rho proteins were subjected to gel filtration chromatography using a HiLoad 16/60 Superdex 200 column on an Akta Purifier system (GE Healthcare). The column was first equilibrated using wash buffer (PBS+0.2% w/v Fos-Choline-14). Pooled elution fractions from the 1D4 immunoaffinity purification concentrated to less than 500 μl using 10 kD MWCO filter columns (Millipore) and then applied to the Akta system. After loading, column was run with wash buffer at 1 ml/min and protein fractions collected and monitored with the UV detector at 215 and 280 nm.

Collected fractions were assayed via dot blotting or polyacrylamide gel electrophoresis (SDS-PAGE) under reducing and denaturing conditions. SDS-PAGE gels were run in tandem with one being used for total protein staining using SYPRO-Ruby (a more sensitive alternative to Coomassie; Invitrogen) and the other transferred to a 0.45 μm nitrocellulose membrane and subjected to western immunoblotting using the 1D4 as primary antibody, followed by secondary (goat anti-mouse HRP), and ECL-Plus Kit detection.

The method of purification was adapted from that described for rhodopsin. For further details concerning these protocols (as well as cell culture and bioreactor conditions), please see the following references:

Reeves P J, Kim J M, and Khorana H G. (2002) Structure and function in rhodopsin: a tetracycline-inducible system in stable mammalian cell lines for high-level expression of opsin mutants. *Proc Natl Acad Sci* 99, 13413-13418; and Reeves P J, Thurmond R L, and Khorana H G. (1996) Structure and function in rhodopsin: high-level expression of a synthetic bovine opsin gene and its mutants in stable mammalian cell lines. *Proc Natl Acad Sci* 93, 11487-11492; the contents of each of which are incorporated by reference herein.

Protocol for Production of Olfactory Receptor hOR17-4 in Yeast *Pichia pastoris*

Materials

Invitrogen EasySelect™ *Pichia* Expression Kit (Invitrogen, Carlsbad, Calif.)

Oligonucleotides were from Integrated DNA technologies, (Coralville, Iowa)

TOPO cloning reaction kit (Invitrogen, Carlsbad, Calif.)

Complete protease inhibitors (Roche)

Fos-choline 14 (Anatrace, Maumee, Ohio)

Methods

Cloning

The gene coding for olfactory receptor with an N-terminal his tag was assembled from oligonucleotides using gene assembling technique through PCR. The oligonucleotides were designed using DNA works (http://molbio.info.nih.gov/dnaworks).

Two restriction sites, EcoRI and XbaI were included in the design of the gene to allow cloning of the gene into pPICZ-A at a later stage. After assembling of the gene, it was cloned into pCRII-blunt-TOPO vector using the TOPO cloning reaction kit. After the gene was cloned into pPICZ-A *Pichia* expression vector. The wild-type *Pichia* strain X-33 was transformed using electroporation.

Expression of hOR17-4

Before induction, biomass of the transformed *P. pastoris* X-33 was accumulated by growing in BMGY (1% (w/v) yeast extract, 2% (w/v) peptone, 1% glycerol, 0.1 M phosphate buffer, pH 7.5) to an optical density (OD) of 2-6. Receptor expression was induced after elimination of medium by centrifugation (1000 g, 10 min) and addition of a buffered methanol-containing medium BMM to OD 1 (0.1 M phosphate buffer pH 7.5, 1.34% yeast nitrogen base, $4*10^{-5}$% biotin, 1% (v/v) methanol). After induction for 40 hrs at 30° C., cells were harvested by centrifugation and frozen at −80° C.

Isolation of Crude Membranes and Solubilization hOR17-4

Cells were thawed and were resuspended in breaking buffer (PBS, 5% glycerol, 1 mM EDTA, protease inhibitors) and were broken by French press, 3 runs at 30,000 Psi at 4° C. Unbroken cells and other larger cell material were eliminated by centrifugation (1,000 g, 10 min, 4° C.). Membranes were pelleted from the supernatant at 100,000 g for 45 min at 4° C., and resuspended in PBS with 2% Fos-choline 14 at 4° C. for 2 hrs.

Cell-free production for smell receptor 17-4

Materials

RTS proteomaster, Roche Diagnostics GmbH, Mannheim Germany

Wheat germ RTS 500 cell free expression kit, Roche Diagnostics GmbH, Mannheim Germany Digitonin 10% solution, EMD Chemicals Inc, Darmstadt, Germany Ac-A6D-COOH 1% solution hOR17:4-Rho ORF in PIVEX expression plasmid from Roche Diagnostics GmbH Mannheim Smell receptor protein production procedure Expression is set up according to Roche's manual and table I. Expression is performed at 24° C. for 24 hours at 900 rpm.

TABLE I

| 17-4 plasmid | Template | | | |
|---|---|---|---|---|
| | Reaction chamber | | Feeding chamber | |
| (μg) | detergent I | detergent II | detergent I | detergent II |
| 60 | Dig. (0.3%) | $A_6D$ (0.1%) | Dig. (0.3%) | $A_6D$ (0.1%) |

Purification of 17-4 from Cell-Free Lysate

Materials

Beads coupled with 1D4 antibody (Pharmacia Sepharose-4B, CNBr activated beads GE Healthcare, Piscataway, N.J., USA FC14, Anatrace, Maumee, Ohio, USA Superdex 200 100/300, GE Healthcare, Piscataway, N.J., USA ÄKTA purifier 10 chromatography system, GE Healthcare, Piscataway, N.J., USA Centricon concentration devices, Millipore, Billerica, Mass., USA Protein Purification Procedure hOR17.4 purification was started immediately after cell free expression was finished.

Figure 1:
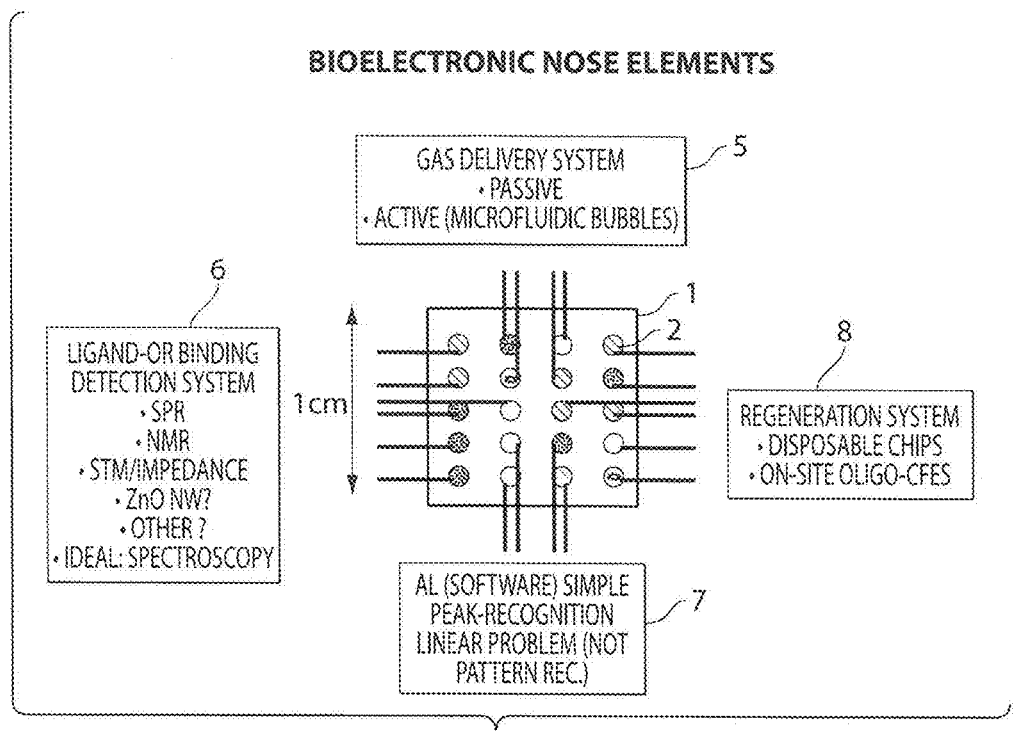
FIG. 1 illustrates elements of an exemplary bio-sensing nanodevice according to the invention.

1. The pellet of unsolubilised material by centrifugation at 15,000×g for min was spun down;
2. The supernatant (900 ul from a 1 ml RTS 500 reaction) was added to 600 μl bead coupled with 1D4 antibodies directed against the Rho-tag and is incubated over night at 4° C.;
3. The beads were spun at 800×g for 1-2 min at 4° C.;
4. The supernatant was removed;
5. Multiple washes of about 10 min each using 100 bed volumes each wash of PBS+10% glycerol+0.1% FC-14 (rotation at 4° C. during incubation, spin down beads between the washes);
6. Five elutions of the receptor using one hour each using one bead volume of elution buffer (PBS+10% glycerol+0.1% FC-14+100 μM peptide (TETSQVAPA (SEQ ID NO: 50))—keep at ROOM TEMPERATURE (rotate at 4° C. during incubation, spin down beads between the elutions);
7. the elution fractions were concentrated to 600 μl using centricon concentration devices with a molecular cut off of 10000 kDa;
8. 2×300 ul were applied to a Superdex 200 100/300 column attached to a ÄKTA purifier 10 chromatography system equilibrated with PBS+10% glycerol+0.1% FC-14;
9. Fractions containing FC14 stabilized monomer were collected at about 112 kDa. The receptor is 36 kDa and bound FC14 is calculated to 76 kDa, see FIG. 1.

Calcium-Influx Activity Assay

To determine if receptors expressed at the surface of induced HEK293S rho5 cells was functional, we performed calcium-influx assays. In our heterologous HEK293S system, olfactory receptors can signal through the inositol triphosphate (IP3) pathway to release intracellular Ca2+, using the "promiscuous" G-protein Gαq.

HEK293S rho5 cells were seeded and grown on glass coverslips until they reached 80-90% confluency. Expression of hOR17-4 was then induced with media containing tetracycline (1 μg/ml) for 48 hours. Cells were then washed with PBS and loaded with the calcium sensitive dye Fluo-3 (Invitrogen) according to the manufacturers instructions. Coverslips were then mounted and visualized using time-lapse confocal microscopy. Experiments were conducted in PBS and odorant stocks were added by hand using a pipettor to final concentrations between 1-100 μM. Both specific and non-specific odorants were tested. As an additional control to test whether cells could increase internal calcium levels, 1 mM ATP was added.

Protocol is Adapted from:

Jacquier V, Pick H, and Vogel H. (2006) Characterization of an extended receptive ligand repertoire of the human olfactory receptor OR17-40 comprising structurally related compounds. *J Neurochem* 97, 537-544.

Example 4

Functionality Smell Receptor Binding Determination Using Surface Plasmon Resonance One of the most important issues of smell receptor production is the functionality and the stability of the synthesized receptor. As there are no standard protocols to detect the interaction between odorant and solubilized smell receptor we have developed such a method using Surface Plasmon Resonance (SPR, Biacore instrument) (described, for example, in Examples 10-12 below). The detection of the binding of the very small smell molecules, the odorants are usually smaller than 250 in molecular weight compared to the ~35,000 in molecular weight receptor, is a very big challenge but not impossible using SPR. Our recent results showed that our produced receptor (from yeast and cell free) is still active after solubilization from the membrane using a phosphocholine (surfactant). This means that the receptor is not only produced in its functional form, but also it is still stable after the solubilization. Obviously, this result is a milestone in the development of the smell biosensor.

Currently, using a set of known agonists and antagonist, as well as non-binding smell molecules, we are investigating the binding of different smell molecules to smell receptors, both qualitatively and quantitatively.

Example 5

Figure 4:
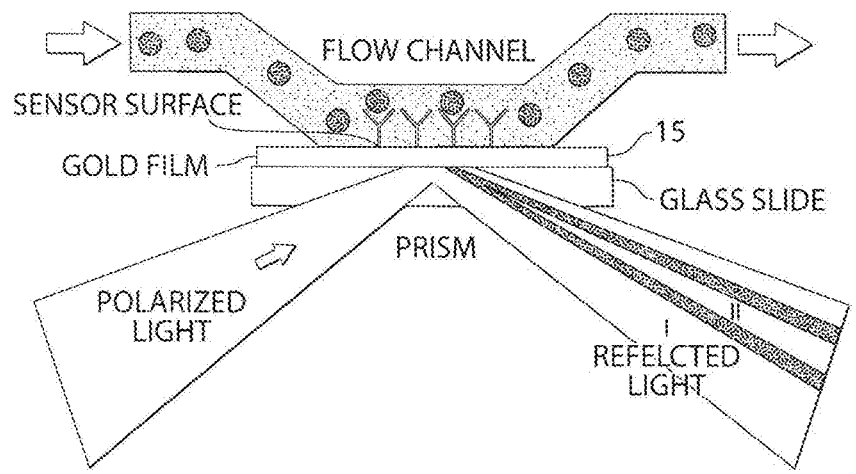
FIG. 4 illustrates physics, optics and chemistry of how Surface Plasmon Resonance works. Binding of smell molecules (red) to a smell receptor (Y) using Surface Plasmon Resonance. This system can be made into an array with thousands of receptors on a biotech chip.
Figure 5:
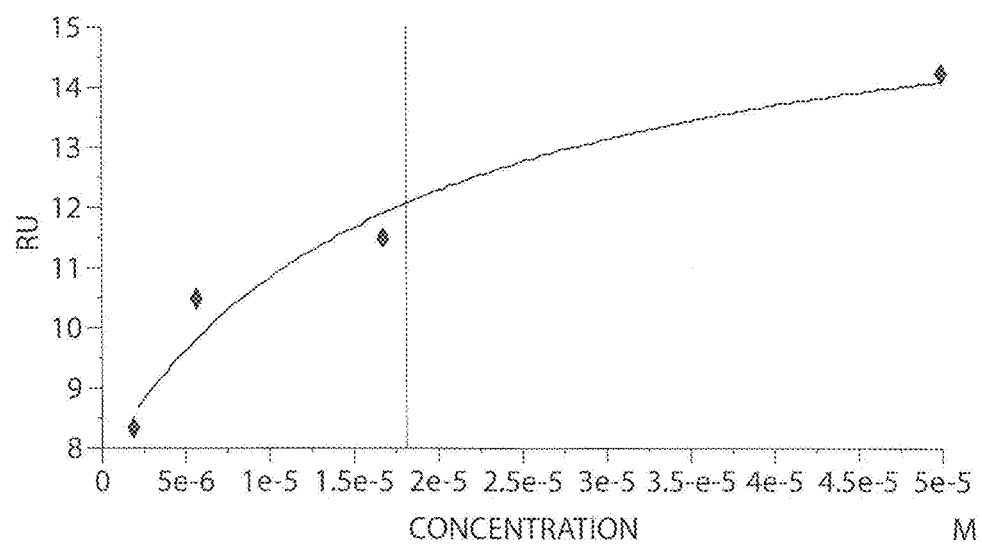
FIG. 5 represents a graph of measured binding of a smell molecule to the smell receptor hOR17-4. The graph shows a dose-response curve indicative of specific interaction between the smell molecule and the receptor. The vertical bar indicates the calculated affinity constant (16 µM).

Stabilization of the Olfactory Receptors in Solution Using Different Chemical Surfactants and Peptide Surfactants Previous work of our lab has successfully kept membrane proteins functionally stable in both wet (aqueous) and dry states for several weeks with the use of the peptide surfactants $A_6K$, $A_6D$ and $V_6D$ As described below, we have used SPR for detection of smell molecules in a SPR based biosensor using an array of receptors from different species and different types of smell molecules. A conceptual embodiment of an SPR sensor is shown in FIG. 4 to illustrate the underlying principles. A sample interaction of a smell molecule and the receptor found on the SPR sensor are shown in FIG. 5. It should be noted that SPR could be miniaturized for the smell receptor based biosensing nanodevice.

Example 6

Structural Determination of the Smell Receptors

Understanding the functional mechanism of olfactory receptors can only be achieved through detailed structural analysis. Considerable evidence suggests that the surfactant peptides will facilitate the crystallization of purified olfactory receptors for X-ray diffraction and may additionally enable the use of both solution and solid-state NMR spectroscopy. In order to perform these studies we need milligram quantities of purified receptors. We currently have stocks prepared from a large-scale production, enough receptor for crystal screenings. This automated screen tests >2000 separate crystallization conditions and results will be applied to crystallizations for completely X-ray diffraction studies.

Example 7

Testing the Vibrational Theory of Olfaction Using Scanning Tunneling Microscopy (STM)

The dominant theory of olfaction is that the shape of the odorant molecule is what olfactory receptors recognize. This theory is problematic because molecules that are shaped exactly alike (for instance an odorant with all its hydrogen atoms replaced by deuterium ones) not only smell different[3], but also give different neural activation patterns. On the other hand, structurally unrelated molecules smell alike (a well-known example is the at least 75 dissimilar shaped molecules-all smelling of bitter almond).

One hypothesis, the "vibrational theory of smell", postulates that when an appropriate odorant molecule binds to an olfactory receptor protein electrical conductance through the receptor increases, activating an intricate biochemical and neural pathway, which ultimately results in the conscious perception of an odor. Although the biochemical aspects of this are well documented, the first step—a local change in conductance—is yet determined.

The most direct way to test the vibrational theory of smell is the method as follows: immobilize an olfactory receptor, in its active form, in a scanning-tunneling microscopy (STM) chamber and measure the efficiency of electron tunneling before and after the receptor is exposed to its odorant. If there is a significant increase in the tunneling efficiency when the receptor has bound its odorant, versus when it is exposed to random odorants, we will have the first ever evidence for the vibrational theory of smell. With this method we will be addressing single molecules in a highly controlled environment.

The most important problem is that the olfactory receptor protein, being a membrane protein, is sensitive and unstable, extremely hard to produce, and nearly impossible to keep functional in unnatural environments such as the insides of an STM chamber. However, in our laboratory we have succeeded in keeping similar proteins (of the G-Protein Coupled Receptor—GPCR family) functional by using custom-designed surfactant peptides to play the role of their natural lipid bilayer environment.

The second problem is assaying that we have a layer of immobilized olfactory receptors on a conducting surface. Following protocols for immobilizing other GPCRs, we have started using SPR to monitor immobilization of monolayers.

We have already confirmed that proteins work well for STM. We have started experimenting with Carbonic-anhydrase protein immobilized on platinum electrodes to understand the thermal and other behavior.

Figure 6:
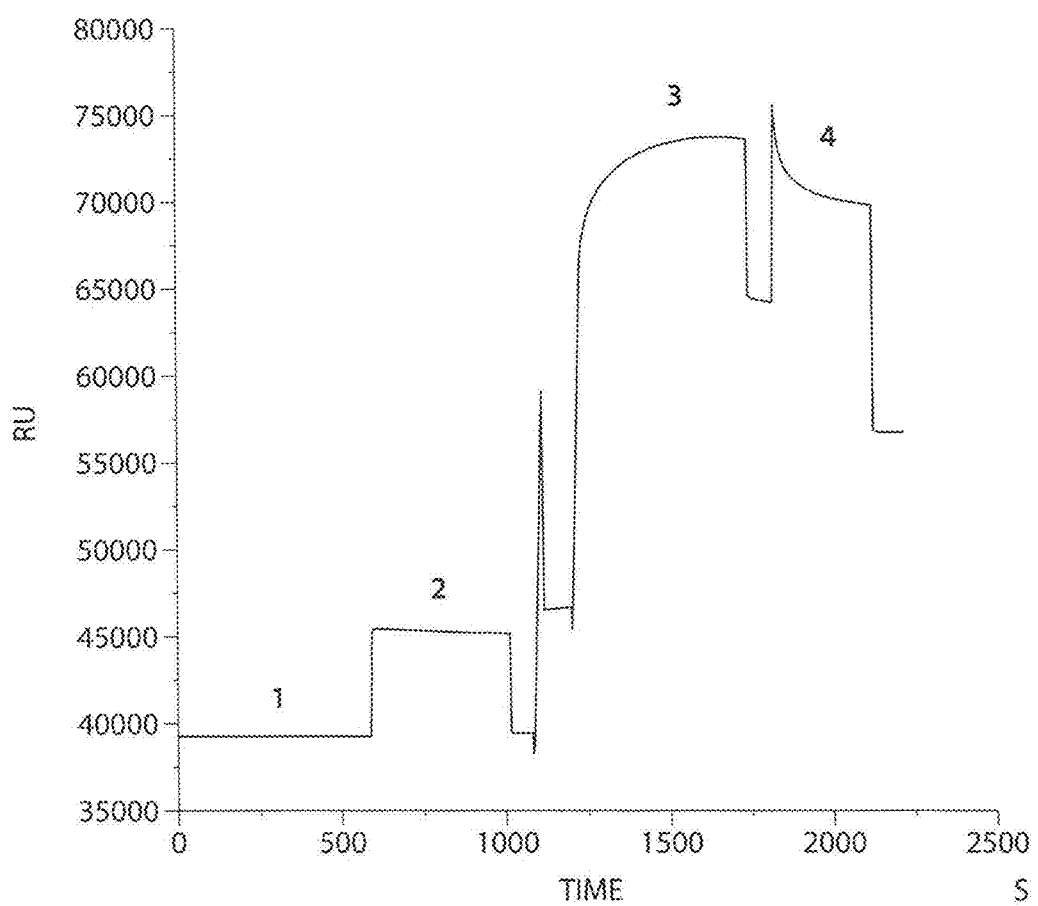
FIG. 6 represents a surface Plasmon resonance graph of the immobilization of ID4 antibody: (1) Running buffer: HBS, flow rate 10 ml/min. (2) Surface activation: Amine coupling: 7-min injection of a 1:1 ratio of 0.4M EDC/0.1M NHS. (3) Immobilization: 3-min injection of 0.05 mg/ml ID4 in 10 mM sodium acetate pH 5.5. (4) Deactivation: 7-min injection 1 M ethanolamine.
Figure 7:
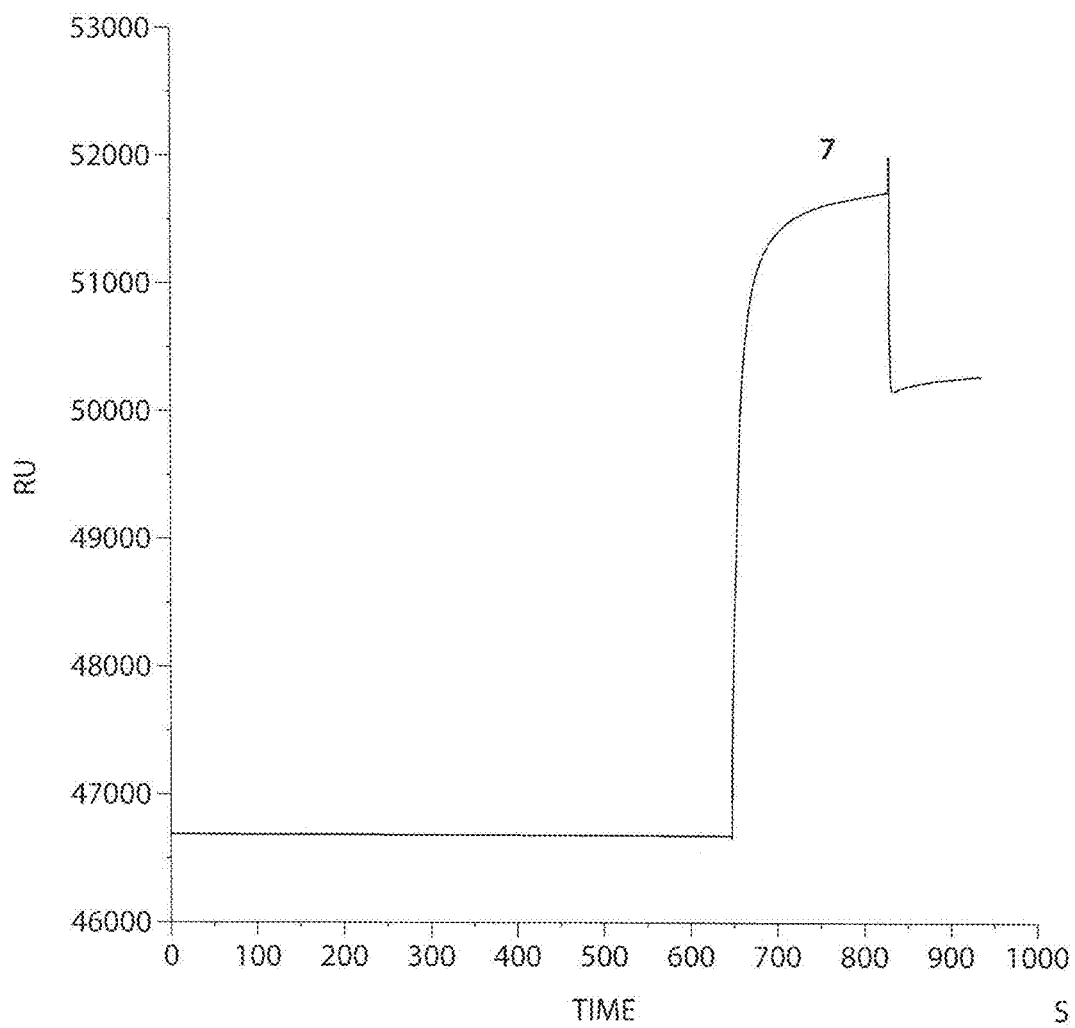
FIG. 7 shows a surface Plasmon resonance graph of the capturing of the olfactory receptor hOR17-4.
Figure 8:
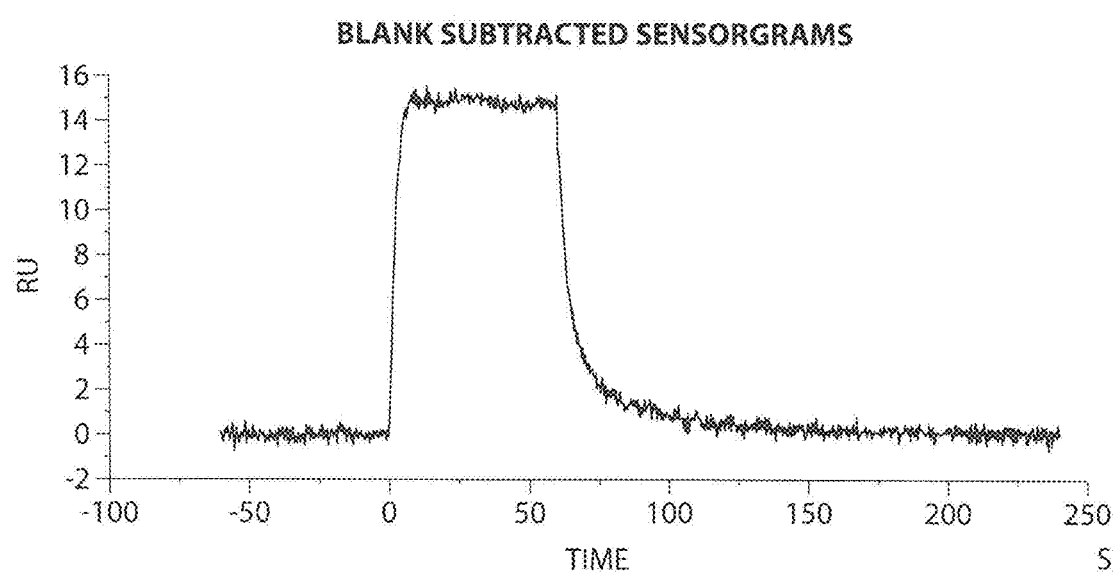
FIG. 8 shows a ligand binding diagram.

Surface Plasmon Resonance of Odorant Binding to Smell Receptor
Materials
Biacore system: T100 and A100
Biasensor chip CM4 (carboxylated dextran immobilized on Au) (Biacore)
EDC: ethyl-3-(3-dimethylaminopropyl) carbodiimide hydrochloride (Biacore)
NHS: N-hydroxy succinimide (Biacore)
Ethanolamine (Biacore)
PBS: 10 mM phosphate buffer pH 7.4; 2.3 mM KCl; 0.137 M NaCl (Biacore)
HBS: 10 mM Hepes pH 7.4; 0.15M NaCl (Biacore)
ID4 antibody (Cell essentials, Boston Mass.)
Ethanol
Floralozone (Flavor Sciences, Stamford Conn.)
Immobilization of ID4 Antibody (See FIG. 6)
 1. Running buffer: HBS, flow rate 10 ml/min.
 2. Surface activation: Amine coupling: 7-min injection of a 1:1 ratio of 0.4M EDC/0.1M NHS.
 3. Immobilization: 3-min injection of 0.05 mg/ml ID4 in 10 mM sodium acetate pH 5.5.
 4. Deactivation: 7-min injection 1 M ethanolamine.
Capture of Olfactory receptor hOR17-4 (see FIG. 7)
 1. Change buffer: PBS, 0.1% (w/v) CHAPS/0.05% CHS/ 0.1% DDM, 1% (v/v) ethanol. Flow rate 10 µl/min.
 2. 2× priming of system.
 3. Capture of olfactory receptor: 3-min injection of hOR17-4 from cell free expression.
Ligand Binding (see FIG. 8)
Injection of odorant solution: contact time 60 s; flow rate 80 µl/min; dissociation time 120 s. Injection of at least 5 different concentrations (1-100 µM, injection from low to high concentration). Preparation of odorant solution: fresh 50 mM stock solution in 100% ethanol, then further dilutions in running buffer.

Example 8

Highly Parallel Receptor-Ligant Interaction Detection System

The goal of this project is to be able to detect a measurable change in the nuclear-magnetic resonance spectrum of the binding of a ligand (smell source or other small molecule) to a receptor protein. The proposal is to create a parallel array of microslot devices [1] which will be able to collect information on these proteins in parallel. The microslot is a recent innovation to improve the sensitivity of magnetic resonance for detecting small quantities of protein. In [1], it was experimentally shows that $10^{14}$ molecules (1.57 nanomoles) of ribonuclease-A in 188 mL of solution could be measured using this technique.

Figure 9:
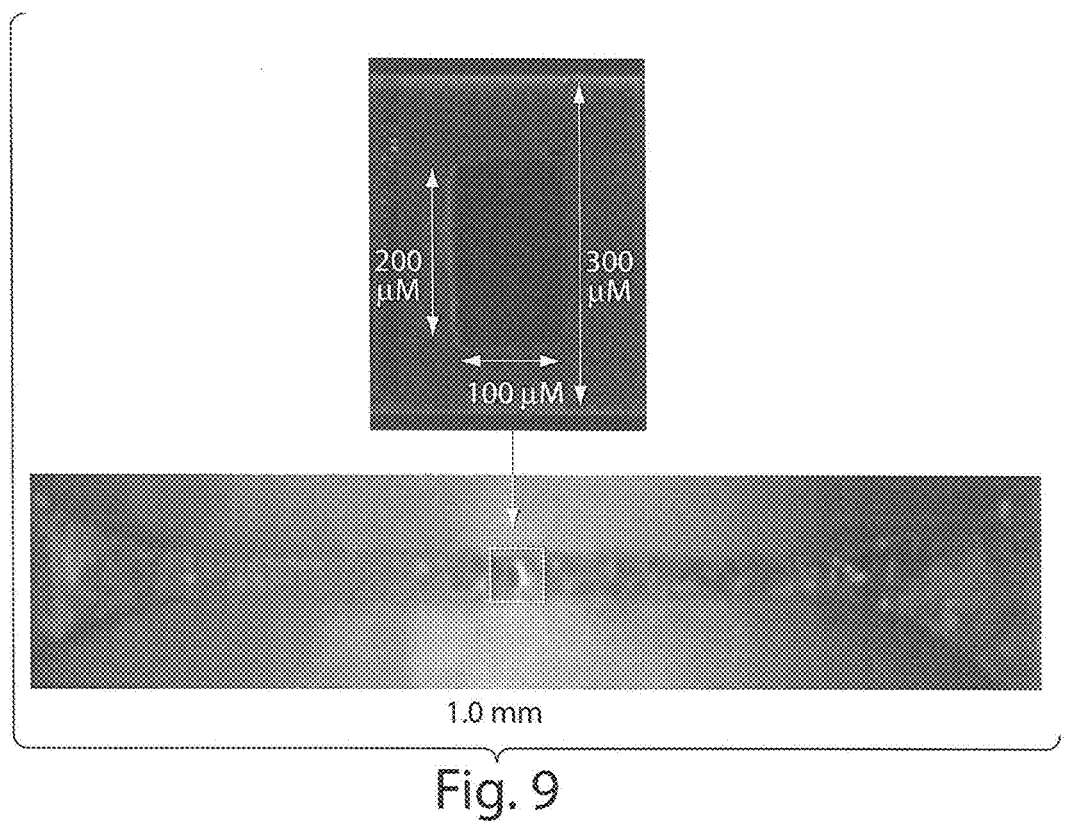
FIG. 9 is a depiction of a microslot probe.
Figure 10A:
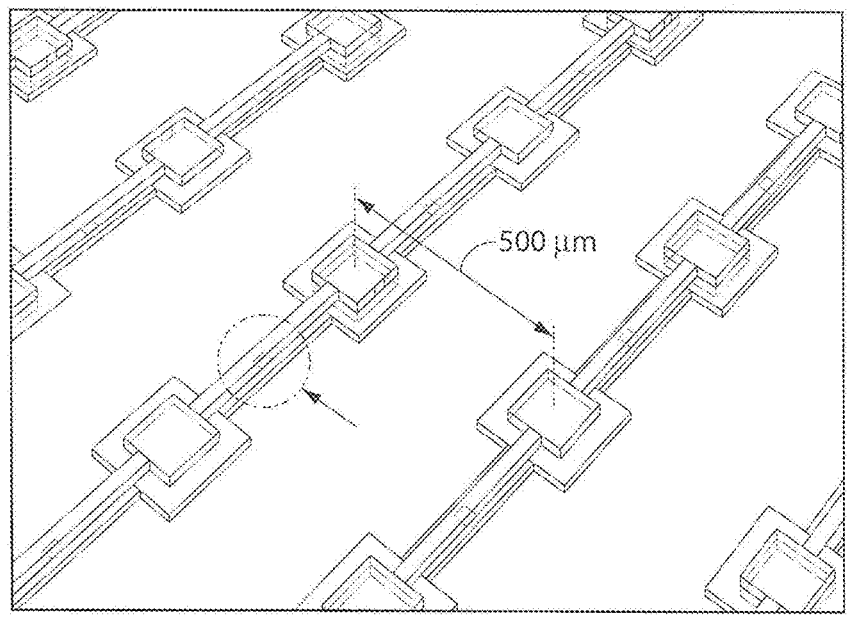
FIG. 10: (a) a close up of the detector element shown with a microfluidic network placed on top, (b) a schematic of a 4×4 mm chip which contains 36 sensors.
Figure 10B:
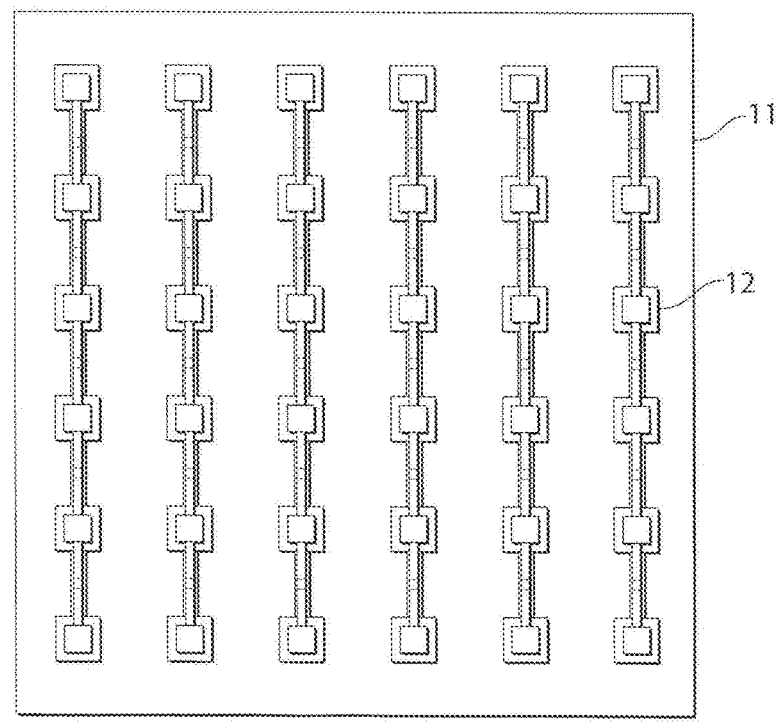

The microslot probe (FIG. 9) was manufactured using conventional circuit board fabrication techniques followed by a fast post-processing step using an excimer laser, which is a highly automated, fast and inexpensive technique. One of the features of this design is that is can be highly parallelized. A visualization of this is shown in FIGS. 10 (a) and (b). The image on the left shows a close up of the detector element shown in the figure above with a microfluidic network placed on top. The image to the right of that is a schematic of a 4×4 mm chip, which contains 36 sensors. The size of the sensor for N elements is 0.5 mm×N+1 mm by 0.5 mm×N+1 mm. A table of this is shown below:

| total # of sensors | dimensions (mm) |
|---|---|
| 36 | 4 × 4 |
| 100 | 6 × 6 |
| 400 | 11 × 11 |
| 900 | 16 × 16 |

The current specifications of each sensor:
984 μmul/$Hz^{1/2}$ at 600 MHz. This scales at $B_0^{7/4}$ with magnetic field strength. This allows 1D spectral determination of $10^{14}$ molecules in up to 200 nL of solution.

REFERENCES

Yael Maguire, Isaac L. Chuang, Shuguang Zhang, and Neil Gershenfeld. Ultra-small-sample molecular structure detection using microslot waveguide nuclear spin resonance. Proceedings of the National Academy of Sciences. pp. 9198-9203. v. 204, no. 22. May, 2007, which hereby incorporated by its entirety.

Example 9

Microfluidic Integration of Olfactory Receptors and Gas Delivery for Bio-Sensing Nanodevice Complex odorant cocktails require a combinatorics approach for detection. Thus a regulated mechanism for exposure of olfactory receptors to test sample is necessary. Receptors on the membrane, sit inside a mucus layer. This thin fluid film is necessary for stability of olfactory receptors in the membrane. The electronic nose needs to imitate such a gas-liquid transport mechanism. For sensitive detection of and fast rejuvenation of olfactory receptors, controlled exposure time to a variety of gas samples is necessary. Increasing the surface area to volume ratio of gas samples by using nano-liter volume bubbles, allows for fast diffusion of odorant molecule into the ambient fluid, improving device sensitivity. For example, a single odorant molecule would take seconds to diffuse to the surface for 1 ml gas sample, while it would take μ seconds to diffuse to a surface of 1 nl bubble. This requires breaking down a test sample into nanoliter bubbles at high frequency. Control of routing of packets of gas bubbles in a microfluidic chip [11] allows us to implement complex detection schemes. We have invented a new family of generalized tools for manipulation of bubbles in complex microfluidic networks. "Bubble Logic" employs micron-sized (nanoliters) droplets and bubbles of chemicals to mimic the actions of the electrons moving through the circuits of a microprocessor. A single bubble represents a bit. Now bits can simultaneously represent and manipulate materials and information. This new paradigm merges chemistry with computation. We have already demonstrated numerous digital logic components employing nanoliter volume bubbles in microfluidic networks; including AND-OR-NOT gates, flip-flops, ripple-counters, constant frequency bubble generators, modulators and ring oscillators. Thus bubbles traveling in a microfluidic channel can carry a variety of gas samples to precise locations on a chip. They can be stored in memory elements, routed on-chip, merged or split and transported at high throughputs.

Figure 11:
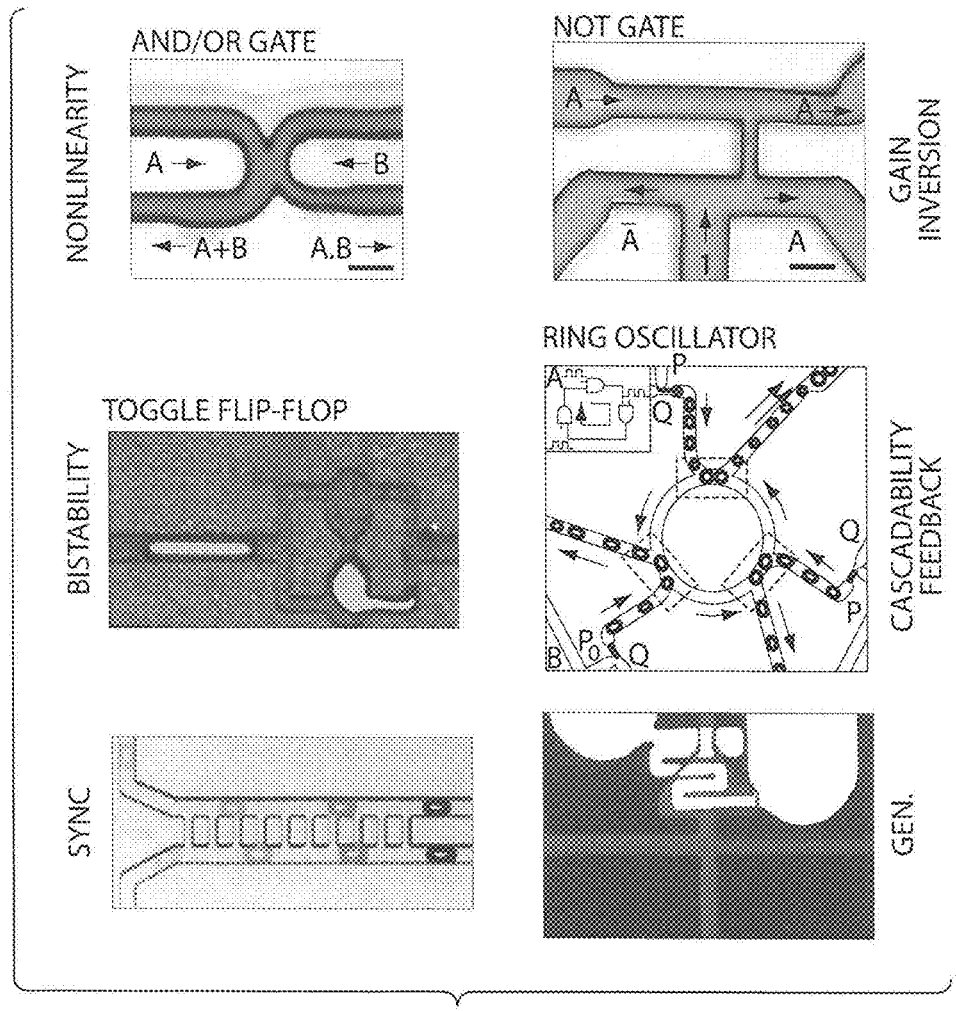
FIG. 11 illustrates numerous digital logic components employing nanoliter volume bubbles in microfluidic networks; including AND-OR-NOT gates, flip-flops, ripple-counters, constant frequency bubble generators, modulators and ring oscillators.

As shown in FIG. 11, numerous digital logic components employing nanoliter volume bubbles in microfluidic networks are possible; including AND-OR-NOT gates, flip-flops, ripple-counters, constant frequency bubble generators, modulators and ring oscillators.

Figure 12:
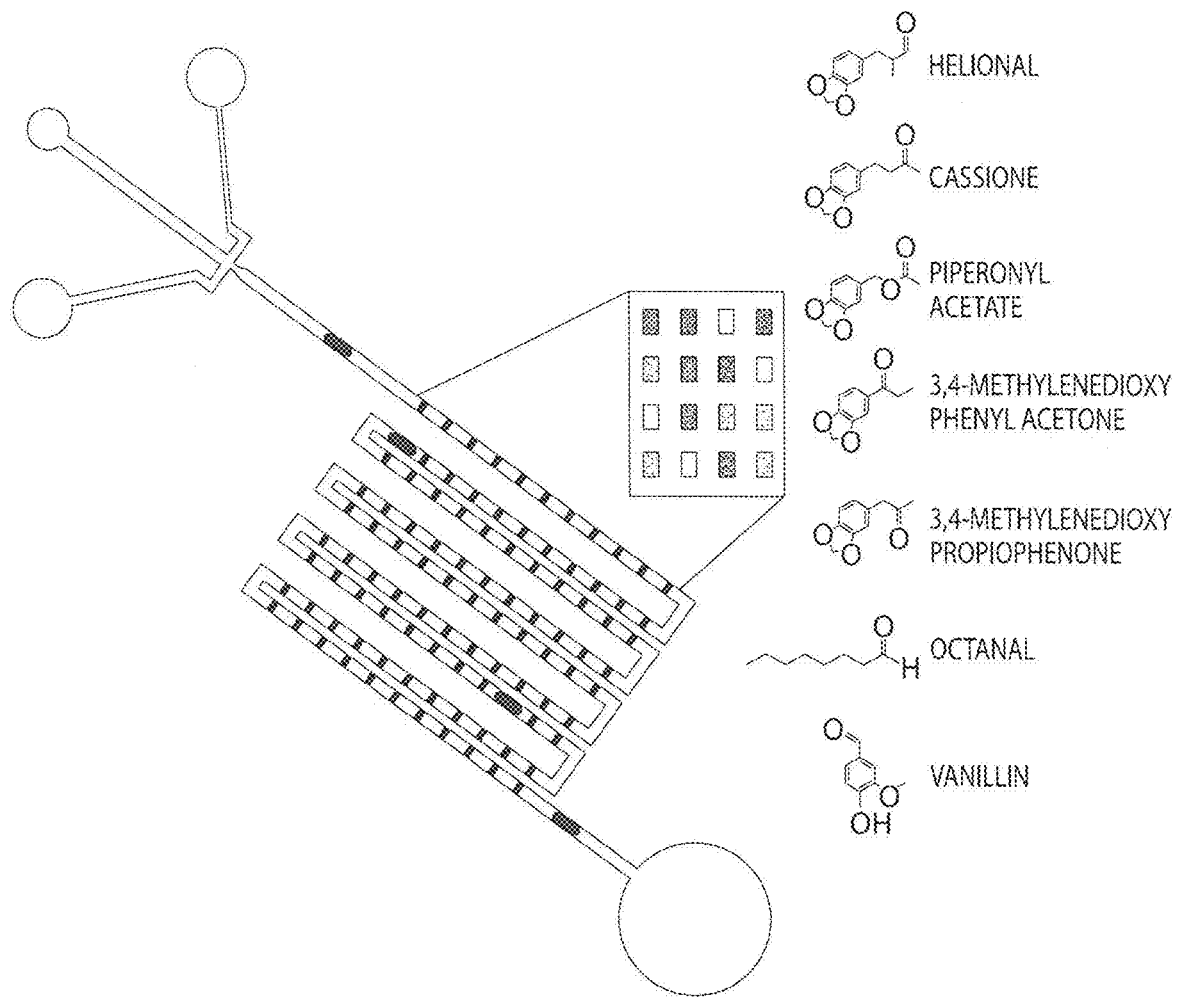
FIG. 12 represents an example of a bubble logic based gas detection schemes.

FIG. 12 represents an example of a bubble logic based gas detection schemes.

Example 10

Efficient Cell-Free Production of Olfactory Receptors—Detergent Optimization, Structure, and Ligand Binding Analyses High-level production of membrane proteins, particularly of G-protein coupled receptors (GPCRs) in heterologous cell-systems encounters a number of difficulties from their inherent hydrophobicity in their transmembrane domains, which frequently cause protein-aggregation, cytotoxicity, thus reduce the protein yield. Recent advances in cell-free protein synthesis circumvent those problems to produce membrane proteins with a yield sometimes exceeding the cell-based approach. Here we report cell-free production of a functional olfactory receptor 17-4 (hOR17-4) using the wheat-germ extract. Using the simple method, we successful produced two additional olfactory receptors. In order to obtain soluble olfactory receptors and to increase yield, we directly added different detergents in varying concentrations to the cell-free reaction. To identify a purification buffer system that maintained the receptor in a non-aggregated form, we developed a method using small volume size exclusion column chromatography combining with rapid and sensitive dot-blot detection. Different buffer components including salt concentration, various detergents and detergent concentration, as well as reducing agent and its concentrations were evaluated for their ability to maintain the cell-free produced protein stable and non-aggregated. The purified olfactory receptor displays a typical a α-helical circular-dichroism spectrum. Using surface plasmon resonance measurement, the hOR17-4 is shown to bind a known ligand undecanal. Our approach to produce high-yield of purified olfactory receptor is a milestone toward obtaining large quantity of olfactory receptors for designing bionic sensors. Furthermore, this simple approach may be broadly useful not only for other classes of GPCRs but also for other membrane proteins.

Introduction

Membrane proteins play vital roles in all living systems. Approximately ~30% of all genes in almost all sequenced genomes code for membrane protein (1-3). However, our understanding of their structures and function falls far behind that of soluble proteins. As of June 2008, there are only 160 unique membrane protein structures of total 375 variations known (http://blanco.biomol.uci.edu/Membrane_Proteins_xtal.html) among over 50,000 structures in the Protein Data Bank (http://www.rcsb.org/pdb/home/home.do). The reason is that there are several notoriously difficult steps to obtain membrane proteins that include: 1) production of large quantities, 2) purification of stable and functional membrane proteins and 3) long-term stabilization of non-aggregated membrane proteins. Membrane proteins are exquisitely nature-made molecular devices that will be very useful for a wide range of applications including solar energy harvesting and ultra-sensitive sensing. In order to accelerate membrane protein structural studies and use them for design and fabrication of nanobiodevices, new and simple methods are crucial.

Among membrane proteins, G-protein coupled receptors (GPCRs) represent the largest family (4, 5). The olfactory receptor is the most common class of GPCRs (6, 7) and perhaps is one of the oldest sensory GPCRs. Although olfaction is an important part of our perception, the olfactory receptor molecular structure currently remains unknown. How the finite numbers of olfactory receptors recognize seemingly infinite odorants remains an enigma. This lack of understanding is mainly due to the difficulty to obtain large quantities of olfactory receptors.

Heterologous expression of olfactory receptors is extremely difficult with only a few examples found in the literature (8-10). The heterologous expression system is often performed in *Escherichia coli* (*E. coli*), yeast or a mammalian cell line. Olfactory receptors expressed in such systems are not only partly located in the membrane, but also found in cell organelles or in inclusion bodies, probably due to inappropriate processing, and the expression levels are often low (11). In addition, expression in mammalian cell lines is time-consuming and expensive (12). For structural, biochemical, and biophysical studies, as well as nanobiodevice design, high yield production is a prerequisite. Therefore the expression of the gene of interest is often driven by a strong promoter resulting in overloading of the different translocation machineries in the cell (13, 14). When production levels increase, so does the burden on the translocation machinery resulting in cellular toxicity and eventually cell death. High level production of membrane proteins in cells as bacteria, yeast and mammalian cells therefore has an inherent fundamental problem.

Cell-free protein production employing extract from various sources as rabbit, insect, wheat germ and *E. coli* provide an attractive alternative since the extract contains all the necessary components for transcription and translation but without membranes. To compensate for the lack of a natural membrane, addition of suitable detergent is crucial for the solubilization and conservation of the freshly produced membrane protein. In addition to detergents, other additives can be supplemented to the reaction to enhance folding such as GroE and DnaK (15).

Recent advances in cell-free protein production technology have improved the protein yields, with the single most important development being continuous exchange feeding systems developed by Spirin and colleagues (16) in which up to ~9.7 mg protein/ml reaction solution have been produced (17). Cell-free production is also fast and convenient in a high-throughput setting, and is currently routinely used at RIKEN Japan for protein synthesis for their structural genomics projects (18). Currently, more than 1000 soluble protein structures have been determined from proteins synthesized by cell-free method (19). However, not a single membrane protein structure has been determined from proteins using the cell-free method.

Klammt et al. investigated the effects of 24 different detergents on the cell-free production of membrane proteins including the GPCR V2R in *E. coli* extracts (20). Most detergents did not affect the yield of either total or soluble membrane proteins. However, detergents such as phosphocholines inhibited the transcription and translation machinery, despite their similarity to natural lipids in the cell membrane. Glycosidases and CHAPS, although both are known as mild detergents, also inhibited protein production. The optimal detergent was found to be protein specific. In the case of a GPCR vasopressin receptor digitonin and Brij generated the highest yields of soluble receptor. Similar results have also been reported for ten other GPCRs produced in *E. coli* cell-free based extracts (20, 21). While the selection of the optimal detergent is crucial to achieve the highest possible yield of soluble membrane protein the composition of the buffer for subsequent purification and storage is equally important.

The ultimate technique for screening buffers composition for optimal membrane protein stability is a protein activity assay. However, these assays are difficult to develop for many membrane proteins (22, 23) and particularly for olfactory receptors. A more feasible approach is to study the protein homogeneity using size exclusion chromatography (SEC). SEC provides information about the protein size and monodispersity as a single symmetrical protein peak indicates that the protein is correctly folded and stable, making it a promising candidate for functional and structural studies (24, 25). By using a short SEC column with a small bed volume, the protein quantity needed per run is small, the short running time allowing for multiple runs per day and efficient buffer scouting. Additionally, a small bed volume reduces the required amount of buffer containing costly detergent.

We here report high-level protein production of three olfactory receptors, hOR17-4, mOR23 and mS51, using cell-free protein production technology as well as a time efficient downstream buffer optimization and stabilization method. The purified protein yields a one milligram per three ml cell-free reaction solution. This quantity is enough to carry out secondary structural and odorant binding functional analyses as well as crystallization screening trials.

Results and Discussion

General Considerations.

Following the reports in the literature of producing GPCRs using *E. coli* extract, also for the lower price consideration of *E. coli* extract as compared to wheat germ based extract; we first used *E. coli* cell-free extracts from both Roche Diagnostics and Qiagen. However we found both produced hOR17-4 both soluble and insoluble at very low or non-detectable levels (results not shown).

Since *E. coli* thioredoxin has been shown to greatly enhance the levels of GPCRs in *E. coli* based extracts, hOR17-4 was cloned into a plasmid including a thioredoxin N-terminally of hOR17-4. The addition of thioredoxin did however not affect the production yield of hOR17-4. The production is driven by a T7-promotor and any vector carrying a T7-promotor and termination sequence and ribosomal binding site should suffice for hOR17-4. Roche Diagnostics provides optimized vectors and linear generation template kits for high-yield production. When production was performed using a linear template, the production levels were not improved.

For production in wheat germ extract the hOR17-4 gene was cloned into pVEX1.3 and pVEX1.4 including a 6-residue histidine tag at either C- or N-terminal, respectively. Compared to production in *E. coli*, wheat germ lysate produced the olfactory receptor in detectable amounts. In addition, pilot studies showed that production from pVEX1.3 was far superior to pVEX1.4 (results not shown).

Effect of Detergents for Olfactory Receptor Yield and Solubility.

Figure 13A:
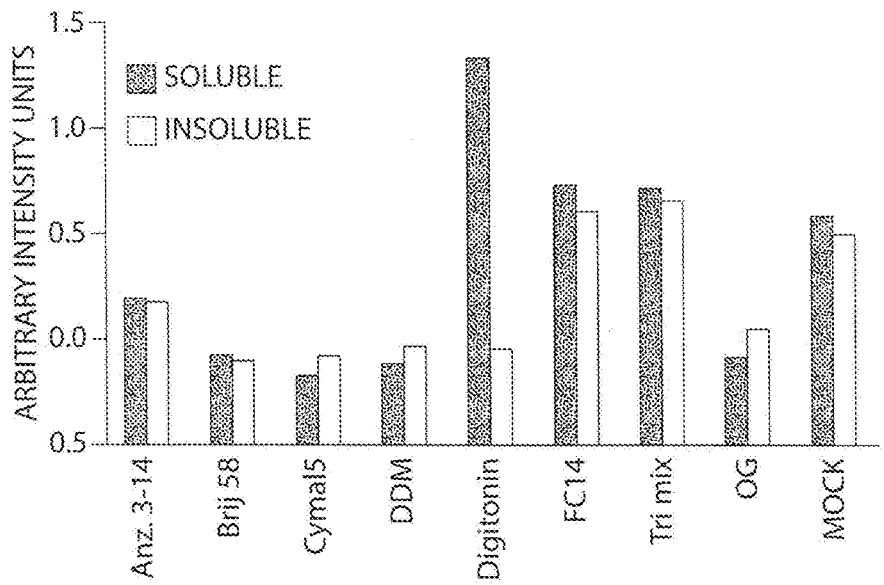
FIGS. 13A and B are bar graphs showing the effects of the first screen of different detergents on olfactory receptor production levels in wheat germ cell-free production systems; (A) The amount of soluble (black bars) and insoluble (gray bars) produced hOR17-4 in different detergents, and (B) Titration of detergent concentration for production of soluble hOR17-4.

Detergents are a prerequisite when working with membrane proteins in solution, and this also holds true for membrane proteins produced in cell-free extracts since both *E. coli* and wheat germ extracts are devoid of lipids. We therefore carefully studied the optimal types and concentrations of various detergents in the cell-free system. A panel of eight detergents was chosen based on their efficacy in previous studies of GPCR production in cell-free extracts or on their ability to solubilize GPCRs expressed in vivo (Table 1). The detergents were all tested at concentrations above their respective critical micelle concentration (CMC) value measured by the suppliers. The detergents effect on the amount of soluble and insoluble produced hOR17-4 was quantitatively measured using the dot blot method (FIG. 13A). OG, DDM, Cyma15 and Brij58 all reduced the production level and Anzergent3-14, FC14 and the Tri-mix either did not or only marginally affected the production level. Digitonin was found to be very effective in maintaining the protein soluble, with no insoluble protein detected. This is in agreement with previous studies of other GPCRs produced in *E. coli* based systems (20).

Figure 13B:
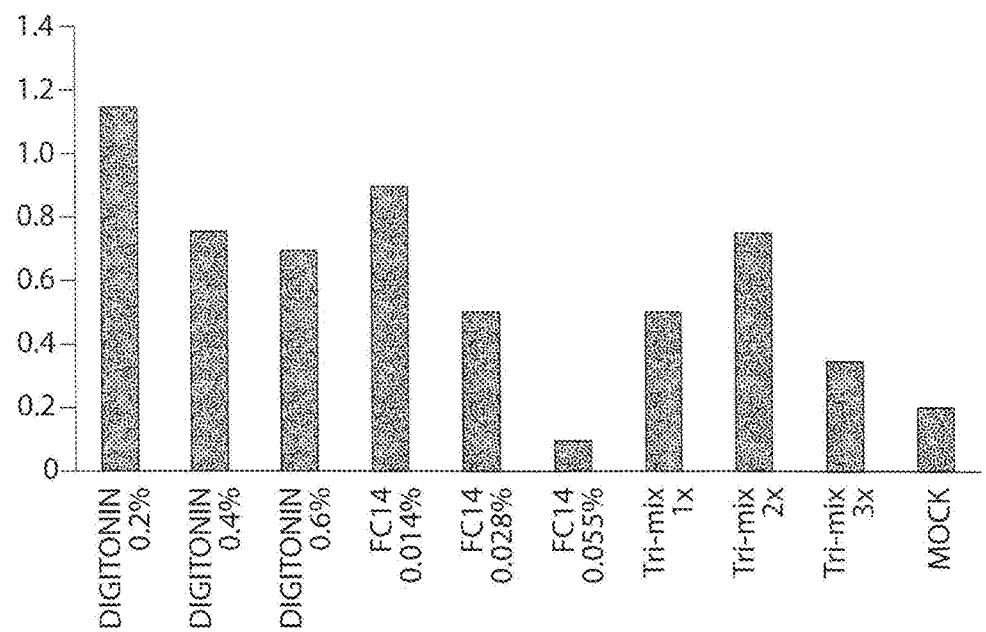
Figure 14A:
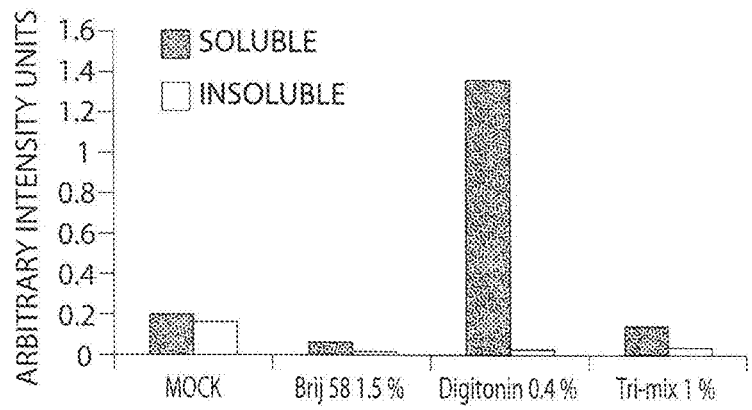
FIGS. 14A-E are bar graphs showing the effect of additional screen of different detergents on olfactory receptor production levels in wheat germ cell-free production system. The amount of soluble (black bars) and insoluble (gray bars) produced in mOR23 (A) and mS51 olfactory receptor production (C) with Brij58, digitonin and Tri-mix. Titration of detergent concentration for production of soluble mOR23 (B) and mS51 (D and E).
Figure 14B:
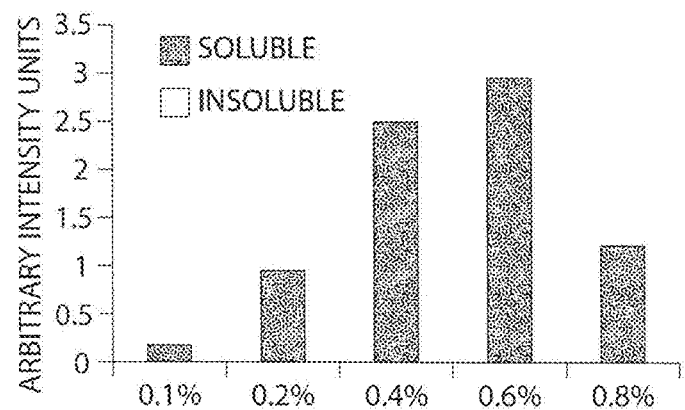
Figure 14C:
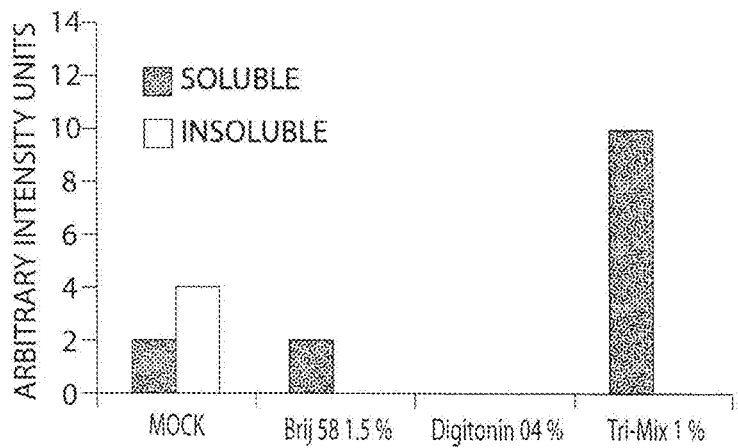
Figure 14D:
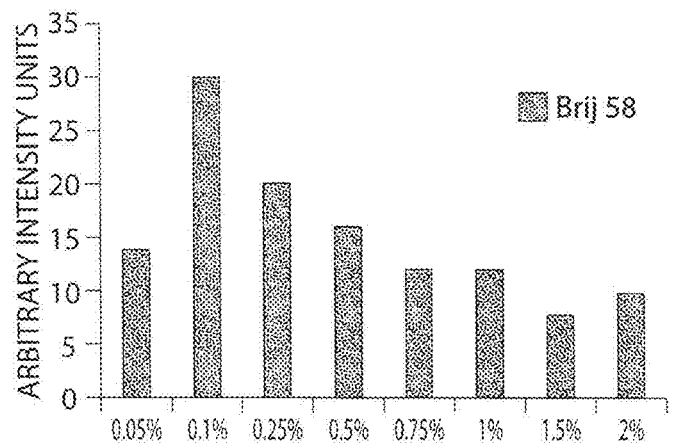
Figure 14E:
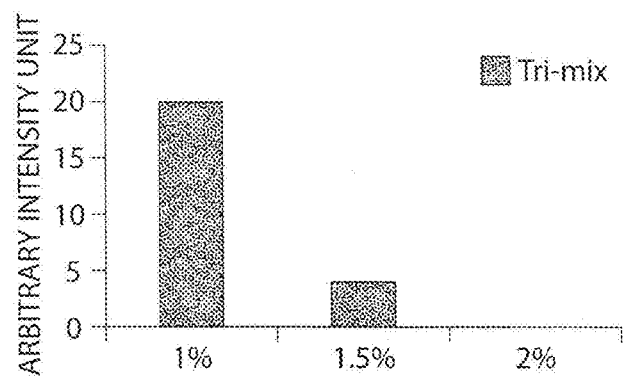

To avoid large protein-detergent micelles and to avoid inhibiting the production system at high concentrations of detergents, we systematically optimized detergent concentration from either decreasing or increasing its concentrations. Increasing the digitonin concentration resulted in very low levels of insoluble protein. In addition to digitonin, the optimal concentration of FC14 and the Tri-mix was also evaluated by increasing the concentration, since the productions levels were reasonable, but the protein was not completely soluble. The yield of soluble receptor could not be increased from increasing concentrations of FC14 or Tri-mix. This is most likely due to an inhibitory effect of these detergents on the cell-free production system (FIG. 13B). The most favorable digitonin concentration was found to be 0.2% and consequently chosen as the standard concentration (FIG. 13B).

To test whether the identified production conditions would also be suitable for other olfactory receptors, mouse receptors mOR23 and mS51 were also produced. The initial detergent screen was reduced to three detergents, namely FC14, Brij58 and the Tri-mix, mainly chosen for their efficacy in producing soluble hOR17-4. Production of soluble mOR23 was similar to the production of hOR17-4, with the highest yield in digitonin, but at a slightly higher digitonin concentration: 0.6% (FIG. 14). The mS51 on the other hand was not produced at all in digitonin, but Brij58 at 0.1% and the Tri-mix at 1× produced high levels of soluble protein (FIG. 14). Once the detergent composition was optimized, production in cell-free extract was proven to be very efficient in producing soluble olfactory receptors, as well as time saving compared to other production systems.

Optimizing Buffer Conditions.

Using GFP as a reporter in SEC based buffer optimization is straightforward and time saving. Protein purification is not necessary and detection can be carried out on-line using a chromatography system (25). However, one drawback using GFP-fusions is that it has to be cleaved off for down-stream applications, such as crystallization. This process has to be optimized so as to avoid loss of protein activity and protein yield. We thus used an alternative approach where a sample from each SEC fraction was dot-blotted on a membrane and developed using an antibody directed against a short C-terminal tag. By using a short SEC column with only a 3-ml bed volume, up to 12 runs with different buffers could be performed in a single day. This time saving step allowed us to investigate the effect of 12 different detergents, 6 different concentrations of NaCl, 2 pH points and the presence of a reducing agent at 3 different concentrations.

Figure 15A:
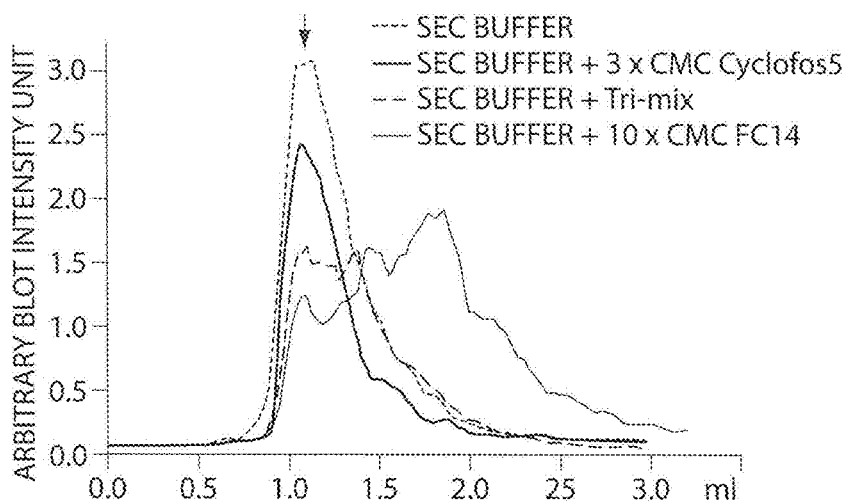
FIGS. 15A-C are plots showing size-exclusion chromatography (SEC) analysis of hOR17-4 aggregation states; (A)
Figure 15B:
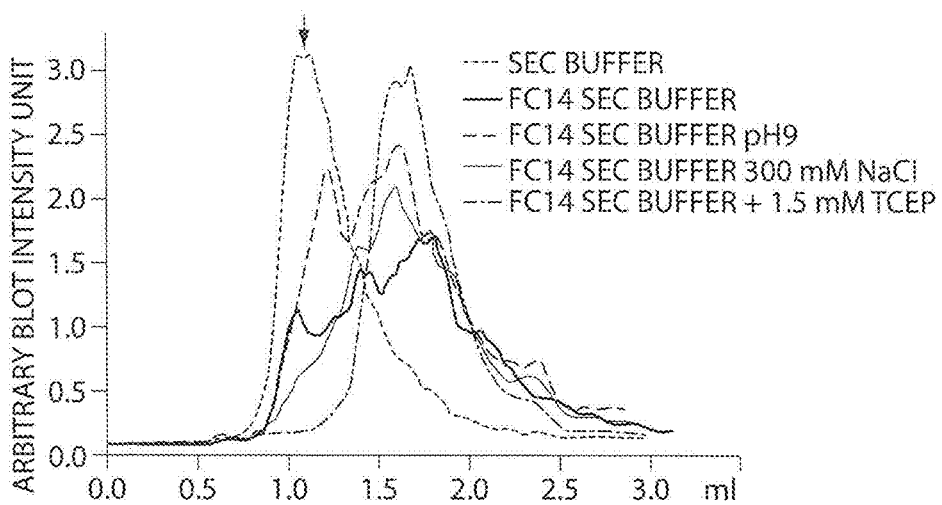

Initially, the presence of 10 different detergents (Table 1) in the run was evaluated. Immediately after cell-free production the protein was captured on 1D4 coated beads and the new buffer was introduced during the washing step. The beads were washed with 100-bed volumes for complete detergent exchange. Exchange to buffers containing $C_8E_4$, DDOMG, LDAO or no detergent resulted in very low or non-detectable levels of hOR17-4 in the eluate from the beads, possibly due to receptor aggregation on the beads. The Tri-mix, Cyclophos5 and DDM on the other hand resulted in high yields, but the receptor eluted from the SEC with the void, indicating that the protein had aggregated to complexes larger than 600 kDa, which is the exclusion volume of the SEC column (FIG. 15). Three of the detergents, Anzergent3-14, Brij58 and FC14, resulted in protein eluting as monomers or as higher molecular-weight oligomers (FIG. 15). The receptor in FC14 buffer eluted at 1.71 ml, corresponding to 114 kDa. The amount of FC14 that binds to hOR17-4 molecule has been calculated to be 76 kDa and when added to the molecular weight of the receptor (36 kDa), it is very close to the observed molecular weight of 112 kDa. The buffers including the 3 most promising detergents were further optimized by varying the pH (pH 7.5 and pH 9.5), NaCl concentration (150 mM and 300 mM) and the presence of a reducing agent TCEP (0 mM and 1.5 mM).

Figure 15C:
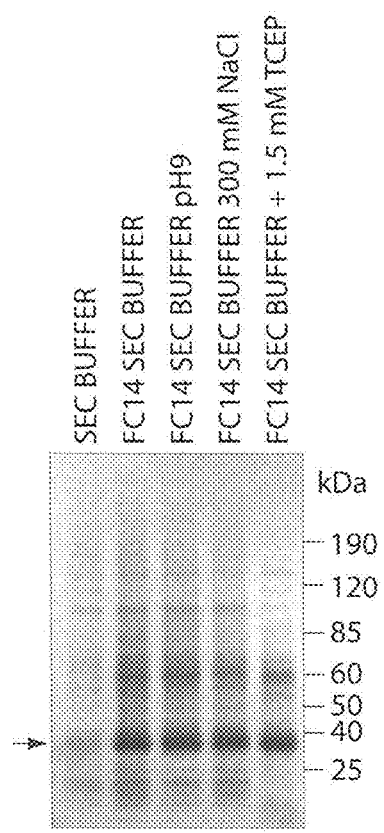

The elution profiles from SEC in the buffers containing Anzergent3-14 and Brij58 respectively were not affected by the different salt concentrations, pH and reducing agent; the receptor was eluted as larger aggregates/oligomeric forms. In the case of FC14 detergent containing buffers there was a marked difference between the buffers (FIG. 15). Higher pH decreased the monomer: aggregate ratio, higher salt concentration increased the same ratio. TCEP fully prevented aggregation and as indicated by the Gaussian shaped peak from SEC, the eluted protein is monodisperse. Addition of TCEP also resulted in a more pure sample from affinity purification (FIG. 15C). As a consequence, FC14 was chosen as detergent for further studies.

As high salt and detergent concentration could be detrimental for crystallization and because high concentration of reducing agent could hamper protein activity, a careful screening of those variables was performed to find the lowest concentration that still kept the protein in a mono-dispersed form. Increasing detergent concentration, up to 200×CMC, resulted in faster elution; 1.56 ml compared to 1.71 ml. This corresponds to a difference in calculated molecular weight of 100 kDa indicating resulting in a lower protein: detergent ratio at 200×CMC compared to 3×CMC (FIG. 16A). High protein: detergent ratio has been reported to impede crystallization and protein activity. Three×CMC resulted in the most well-defined peaks. The salt concentration was screened between 50 mM and 300 mM NaCl and concentrations below 150 mM were found with lower yields of receptor (FIG. 16B). Interestingly, varying salt concentration did not affect the receptor retention volume. Addition of reducing agent prevented aggregation at as low as 1 mM (FIG. 16C). The optimal buffer conditions were finally identified after testing different combinations of the salt, detergent and TCEP concentrations identified above. Two buffers, one with TCEP and one without, were chosen for further studies. Buffer 1:25 mM Tris pH 7, 10% glycerol, 3×CMC FC14 and 200 mM NaCl and buffer 2:25 mM Tris pH 7, 10% glycerol, 3×CMC FC14, 150 mM NaCl and 1 mM TCEP. SEC in a TCEP containing buffer resulted in a single Gaussian shaped peaks, indicative of a mono-dispersed protein sample. SEC without TCEP resulted in monomer, dimer as well as aggregation peaks but monomers could be separated from the other forms. Models of hOR17-4 predict the presence of disulphide bonds and their reduction by TCEP could hinder protein folding and function. TCEP however, breaks down over time and disulphide bonds will form again.

Large-Scale Purification.

For further studies of secondary and tertiary structure as well as crystallization studies pure receptor at high concentration is needed. Crystallization is usually required at concentration greater than 5 mg/ml and circular dichroism measurements require concentrations ~0.2 mg/ml. Large-scale purification of the hOR17-4 receptor from up to 6 ml reaction solution was carried out by increasing the bed volume of 1D4 antibody coated beads. The same pattern as in the buffer optimization experiments was observed with TCEP resulting in a purer sample. The 1D4 antibody is highly specific and in comparison with a $Ni^{2+}$-chelate based affinity purification the 1D4 was able to purify the receptor from very low levels in the reaction solution to 70% purity in one step (results not shown). For further purification the eluted fractions were concentrated and applied to a 24 ml SEC column. The peaks containing hOR17-4 were pooled and concentrated again. The yield was determined to be ~0.3 mg pure hOR17-4/ml cell-free reaction solution. Eleven GPCRs have previously been produced in cell-free lysates at high levels. The yield of unpurified receptors ranged between 0.15-6 mg/ml reaction lysate (20, 21). A few of the receptors have been purified but no yields have been reported. Each purification step always results in protein loss, for example, a 50% yield has been reported for a 2-step purification scheme of the GPCR neurotensin (26). The yield of pure hOR17-4 is well in agreement with what could be expected from the literature of unpurified GPCRs produced in cell-free systems.

Secondary Structure Analysis of Purified Receptors.

Correct protein structural folding largely depends on the mode of production and on the properties of the buffer milieu in which the protein is stored. Olfactory receptors are one member of the GPCRs, which are predicted to have mostly alpha-helical structure with seven trans-membrane helices. The GPCR alpha helical feature has been verified by the two high resolution structures that has been solved (27-29). Both CD spectra from purified hOR17-4 in buffer with and without reducing agent (buffer 1 and buffer 2) display the typical alpha helical features (FIG. 17). The mean residue ellipticity was more distinct from hOR17-4 purified in buffer 2 that contains the reducing agent TCEP.

Surface Plasmon Resonance (Biacore T100) Detection of Odorant Interaction with hOR17-4.

Figure 18B:
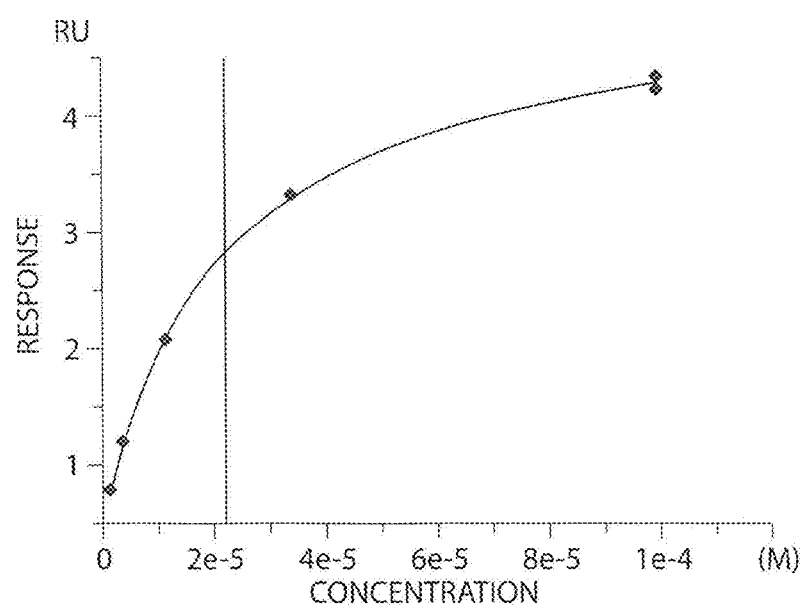

The CD measurements suggest that hOR17-4 is correctly folded. We ask whether the receptor is able to bind to the odorants. The activity of a solubilized olfactory receptor is very difficult to assess since its ligands are mostly below 300 Da, the receptor itself is more than 100 times larger 36,000 Da. Furthermore, the ligand binding pocket is predicted to be buried within the protein, which makes it difficult to measure odorant binding. SPR is a label free technology, sensitive enough to detect the extremely small difference in mass when the odorant binds to the receptor captured on the sensor chip surface. We here demonstrate the dose response binding in binding (RU) of the known ligand undecanal to the hOR17-4 receptor on the Biacore chip (FIG. 18A). The binding response increases by increasing odorant concentration as expected. All concentrations reached equilibrium and the data was used to derive the affinity constant, $K_D$, of 22 uM Other in vitro experiments have shown that odorants bind to hOR17-4 with EC in the micro-molar range (30) (FIG. 18B).

While these experiments represent preliminary exploration into understanding such interactions; future experiments where odorants or ligands having more homogenous aqueous solution behavior are utilized, will yield further mechanistic or functional information.

Conclusion

Our study of producing three olfactory receptors using wheat germ cell-free extracts proved the simple technology to be very useful to obtain functional GPCR membrane proteins. Together with efficient buffer scouting using small volume size exclusion chromatography, appropriate detergent and other buffer components could be identified. In addition, the high-yield production provided enough olfactory receptor to initiate detail structural analysis. Since most membrane proteins are natural molecular devices, our work will likely facilitate the design of membrane protein based nano-bio devices for a wide range of applications, from detection of extremely infinitesimal amounts of odorants, emitted from diverse diseases and environment, to direct harvest of solar energy.

TABLE 2

Detergents used for cell-free production of olfactory receptors

| Detergent | Charge* | CMC (%)** | Concentration (×CMC)*** |
|---|---|---|---|
| Anzergent 3-14 | zw | 0.007 | 3 |
| Brij 58 | ni | 0.00045 | 3300 |
| Cymal 5 | ni | 0.12 | 4 |
| digitonin | | 0.089 | 4 |
| DDM | ni | 0.0087 | 11 |
| FC14 | zw | 0.0046 | 3 |
| Tri-mix (CHAPS, CHS, DDM) | zw. a. ni | 0.49. na. 0.0087 | 2. na. 115 |

*a = anionic; zw = zwitter ionic; ni = non-ionic,
**CMC in $H_2O$ from www.anatrace.com,
***concentration of detergent used during initial cell free experiments

TABLE 3

Detergents used for cell free production of olfactory receptors

| Detergent | Charge* | CMC (%)** | Concentration (×CMC)*** |
|---|---|---|---|
| Anzergent 3-14 | zw | 0.007 | 3 |
| Brij 58 | ni | 0.00045 | 22 |
| C8E4 | ni | 0.25 | 3 |
| Tri-mix (CHAPS, CHS, DDM) | zw. a. ni | 0.49. na. 0.0087 | 2. na. 115 |
| Cyklophos 5 | zw | 0.15 | 3 |
| Cymal 5 | ni | 0.12 | 3 |
| DDM | ni | 0.0087 | 4.5 |

TABLE 3-continued

Detergents used for cell free production of olfactory receptors

| Detergent | Charge* | CMC (%)** | Concentration (×CMC)*** |
|---|---|---|---|
| DDOMG | zw | 0.041 | 3 |
| FC14 | zw | 0.0046 | 10 |
| LDAO | zw | 0.023 | 4 |

*a. anionic; zw. zwitter ionic; ni. non-ionic,
**CMC in H20 from www.anatrace.com,
***concentration of detergent used during buffer screening Materials and Methods
Reagents.

All detergents where purchased from Anatrace, Maumee, Ohio, US, exempt Digitonin EMD (Merck), Darmstadt, Germany. The cell-free protein production kits (both E. coli and wheat germ systems) were purchased from Roche Diagnostics, Indianapolis, Ind., USA. Protein purification materials are purchased from GE Healthcare Life Science, Uppsala, Sweden. Others are described below.

Cell-Free Production.
Generation of DNA Template.

The open reading frame for the human olfactory receptor 17-4 (hOR17-4) (UniProt accession number P34982) was generated using PCR-based gene synthesis. By using the free program DNAWorks (http://helixweb.nih.gov/dnaworks) oligonucleotides were designed to build the open reading frames of the olfactory receptors for PCR-based gene synthesis. The open reading frame of hOR17-4 was optimized for E. coli class II codon usage with the addition of a six residue long C-terminal histidine tag followed by a stop codon and N and C-terminal att-sites. The following parameters were used for automatic design of the oligos: oligo size 45 nucleotides, annealing temperature 58° C., 25 nM oligonucleotide, 10 mM sodium, 2.0 mM Mg$^2$ and the codon frequency threshold was set at 100%. The PCR product was cloned into pDEST42 and pBAD-DEST49 (Invitrogen Carlsbad, Calif., USA) for non-fused and thioredoxin-fused protein production, respectively, according to manufacturer's instructions. Linear templates for production in RTS100 HY E. coli kit was generated using RTS E. coli Linear Template Generation Set (Roche), according manufacturer's instructions with a six residue long C-terminal histidine tag. For production of hOR17-4, OR23 and S51 in wheat germ extract a human codon optimized version was produced in a similar manner but with Nco I and Sma I restriction sites for cloning into pIVEX1.3 WG and pVEX1.4 WG which includes a six residue long C- or N-terminal histidine tag, respectively, according to manufacturer's instructions. A third construct for production in wheat germ extract was generated with the nine residues long Rho-tag (TETSQVAPA (SEQ ID NO: 50)) instead of the C-terminal histidine tag. The constructs encoding the olfactory receptors were verified by DNA sequencing. Plasmid DNA template for cell-free production was obtained from Genopure Maxi Kit (Roche) with an OD260/280<1.7. The plasmid was aliquoted and stored at −20° C. and the same batch was used throughout the study.

Cell-Free Production in Escherichia coli Extracts.

Production of hOR17-4 in E. coli extracts was performed using RTS 100 HY E. coli kit, RTS E. coli Disulphide kit, and EasyXpress Protein Synthesis Mini Kit (Qiagen, Valencia, Calif., USA) according to manufacturer's instructions in pDEST42 and pBAD-DEST49 production plasmids. A linear template was also used in the case of the RTS 100 HY E. coli kit.

Cell-Free Production in Wheat Germ Extracts.

Small-scale production in wheat germ lysate was performed in 50 μl reaction chambers using RTS 100 Wheat Germ CECF kit. Large scale 1 ml reactions, was carried out using RTS 500 Wheat Germ CECF kit.

An initial screen was set up to test the effect of detergents on the yield of soluble receptor hOR17-4 by adding different detergents to the reaction chambers, see Table 1. The concentrations tested were all above the CMC of the respective detergent. The concentrations of respectively Digitonin, Brij58, DDM, OG and DDM were based on previous results of production of GPCRs in E. coli cell-free systems (20). The optimal concentration of FC14, Digitonin and the Tri-mix to keep the freshly produced receptor soluble was further tested at concentrations between 0.014-0.055%, 0.2-0.6% and 1-3×, respectively. Initial detergent screening for soluble production of OR23 and S51 was performed in FC14, Digitonin and the Tri-mix and the optimal concentration was identified by titration of the detergent that resulted in the highest production in the initial screen with hOR17-4. When the production cycle had terminated the reaction solution was centrifuged for ten minutes at 16,000×g at four degrees Celsius to separate soluble and insoluble proteins.

To analyze the effect of the different detergents 1.5 μl of the soluble and insoluble fraction was dotted on a Protran BA85 nitrocellulose membrane (Whatman, Dassel, Germany). The membrane was blocked, washed, and probed with either a 1D4 antibody directed against the Rho-tag or an anti-His antibody (Novagen/Merck, Darmstadt, Germany), and developed as previously described (31). The intensity of the spot was recorded using an AlphaImager (Alpha Innotech, San Leandro, Calif., US).

Olfactory Receptor Purification.

Purification of the receptor was carried out using Sepharose-4B beads (GE Healthcare, Uppsala, Sweden) with covalently linked 1D4 antibodies specific for the Rho-tag. The antibody coated beads were prepared as described earlier (32). For small scale purification from 75 μl production reaction solution 50 μl beads washed in PBS was used. The reaction solution-bead mix was incubated end over end for four hours at 4° C. Purification was hereafter performed in empty spin columns and unbound material was removed by gravity flow. The beads were washed five times using in total five ml of purification buffer. Finally, hOR17-4 was eluted by adding 50 μl purification buffer containing 200 μM of the peptide TETSQVAPA (SEQ ID NO: 50) to the beads and the column was capped and incubated one hour at room temperature shaking. The protein was collected by centrifugation at 800×g for ten seconds.

Large scale purification was performed as described above with the following exceptions. The amount of 1D4 antibody coated beads was increased to a final 3:2 ratio of cell-free reaction solution to beads. The receptor was eluted in 5-7 bed volumes of buffer supplemented with the elution peptide. The eluted protein was concentrated to one third of the volume using a ten NMWL Microcon spin filter (Millipore, Billerica, Mass., USA) and injected on a Superdex 200 10/300 24 ml SEC column (GE Healthcare Life Science) for further purification and to remove elution peptide from the sample. For stabilization studies and crystallization the eluted receptor was concentrated using a ten NMWL Amicon Ultra-4 Centrifugal Filter (Millipore). Protein concentration was measured throughout the study by a reducing agent compatible microplate BCA assay (Pierce, Rockford, Ill., USA).

Optimization of Buffer Conditions.

After small scale affinity purification using 1D4-coupled beads the oligomeric state of the protein eluted in different buffers was assayed using a short three ml size exclusion column, Superdex 200 25/150GL (GE Healthcare Life Science). 50 µl fractions were collected in micro well plates and 1.5 µl of each fraction was dotted on a cellulose membrane (Protran BA85 nitrocellulose membrane) to assay protein amount. The intensity recorded from each spot was inserted in an activity histogram in the ÄKTA software Unicorn version 5.11 (GE Healthcare Life Science) and smoothed over two fraction volumes. For buffer optimization a one ml wheat germ reaction was used for scouting up to twelve buffers.

Secondary Structural Analysis Using Circular Dichroism.

CD measurements of the hOR17-4 were performed at protein at 0.3 mg/ml. The investigations were carried out on an Aviv 202 spectropolarimeter (Aviv Biomedical, Lakewood, N.J., USA) using a one mm path length cell, equilibrated at 25° C. Spectra were recorded between 200 and 250 nm with one nm resolution with a two second averaging time. The final spectra were baseline-corrected by subtracting the corresponding buffer spectra obtained under identical conditions. Results were expressed as the molar mean residue ellipticity (θ) at a given wavelength.

Surface Plasmon Resonance (Biacore T100) Odorant Binding Assay.

All odorant binding experiments were performed on a Biacore™ T100 (GE Healthcare, Uppsala, Sweden) at 25° C. The sensor chip CM4, amine coupling kit, HBS (10 mM Hepes, 0.15 M NaCl, pH 7.4) and PBS were from (GE Healthcare, Uppsala, Sweden).

A anti His-tag antibody (R&D Systems, Minneapolis, Minn., USA) at 5 µg/ml in 10 mM sodium acetate pH 4.75 was immobilized onto a series S sensor chip using standard amine-coupling chemistry in HBS running buffer at 10 µl/min (33). The amount of coupled antibody was about 13000 RU. Control surfaces were prepared similarly without protein derivatization and utilized as a reference surfaces for compound binding experiments. Cell-free lysate containing the expressed olfactory receptor was centrifuged for 15 at 14000×g at 4° C., to remove larger particles. The supernatant, containing about 0.6 mg/ml olfactory receptor, was immediately captured on the surface plasmon resonance (SPR) chip using PBS and 3% (v/v) DMSO as running buffer at 10 µl/min. A four-minute injection resulted in a surface density of about 6000 RU. A 30 sec pulse of coupling reagents was injected to achieve the stable baseline needed for the kinetic assay.

Fresh odorant undecanal solutions were made as follows. Pure odorant was diluted in DMSO to 0.5 M. This solution was diluted 33.3 times in PBS to obtain a 500 mM odorant solution in running buffer with 3% (v/v) DMSO. Further dilutions were made in running buffer containing 3% (v/v) DMSO to obtain a concentration series of 1.2 µM, 3.7 µM, 11 µM 33 µM and 500 µM of odorant undecanal.

For the actual binding measurements, the odorant concentration series were injected from low to high concentration over control and derivatized surfaces for 60 seconds with a flow rate of 60 µl/min. Zero concentration blank buffer cycles were included as negative control samples. Solvent correction procedures were included to compensate for any DMSO related bulk refractive index variations and performed as described previously[34]. Non-specific binding effects to sensor surface CM4 were absent for all analyses reported.

Data analysis was carried out using Biacore T100 evaluation software. Data were prepared by subtraction of reference surface data and blank buffer sample data, a procedure commonly referred to as double referencing[35]. Solvent correction was then applied as described previously[34].

Other methods and results are described in Kaiser et al. (2008). PNAS 105(41): 15726-15731, the contents of which are expressly incorporated by reference herein.

REFERENCES

1. Wallin, E., von Heijne, G. (1998) Genome-wide analysis of integral membrane proteins from eubacterial, archaean, and eukaryotic organisms. Protein Sci 7: 1029-1038.
2. Loll, P. J. (2003) Membrane protein structural biology: the high throughput challenge. J Struct Biol 142: 144-153.
3. Nilsson, J., Persson, B., von Heijne, G. (2005) Comparative analysis of amino acid distributions in integral membrane proteins from 107 genomes. Proteins 60: 606-616.
4. Strader, C. D., Fong, T. M., Tota, M. R., Underwood, D., Dixon, R. A. (1994) Structure and function of G protein-coupled receptors. Annu Rev Biochem 63: 101-132.
5. Burne, H., Horuk, R., Kuhnke, J., Micheal, H. (2007) GPCRs: From deorphanization to lead structure identification (Spriner-Verlag, Berlin, Heidelberg, N.Y.).
6. Buck, L., Axel, R. (1991) A novel multigene family may encode odorant receptors: a molecular basis for odor recognition. Cell 65: 175-187.
7. Araneda, R. C., Kini, A. D., Firestein, S. (2000) The molecular receptive range of an odorant receptor. Nat Neurosci 3: 1248-1255.
8. Breer, H., Krieger, J., Meinken, C., Kiefer, H., Strotmann, J. (1998) Expression and functional analysis of olfactory receptors. Ann NY Acad Sci 855: 175-181.
9. Kiefer, H., Krieger, J., Olszewski, J. D., Von Heijne, G., Prestwich, G. D., et al. (1996) Expression of an olfactory receptor in *Escherichia coli*: purification, reconstitution, and ligand binding. Biochemistry 35: 16077-16084.
10. Vidic, J. M., Grosclaude, J., Persuy, M. A., Aioun, J., Salesse, R., et al. (2006) Quantitative assessment of olfactory receptors activity in immobilized nanosomes: a novel concept for bioelectronic nose. Lab Chip 6: 1026-1032.
11. Ivic, L., Zhang, C., Zhang, X., Yoon, S. O., Firestein, S. (2002) Intracellular trafficking of a tagged and functional mammalian olfactory receptor. J Neurobiol 50: 56-68.
12. Lundstrom, K. (2004) Structural genomics on membrane proteins: mini review. Comb Chem High Throughput Screen 7: 431-439.
13. Tate, C. G. (2001) Overexpression of mammalian integral membrane proteins for structural studies. FEBS Lett 504: 94-98.
14. Wagner, S., Bader, M. L., Drew, D., de Gier, J. W. (2006) Rationalizing membrane protein overexpression. Trends Biotechnol 24: 364-371.
15. Buchner, J., Pastan, I., Brinkmann, U. (1992) A method for increasing the yield of properly folded recombinant fusion proteins: single-chain immunotoxins from renaturation of bacterial inclusion bodies. Anal Biochem 205: 263-270.
16. Spirin, A. S., Baranov, V. I., Ryabova, L. A., Ovodov, S. Y., Alakhov, Y. B. (1988) A continuous cell-free translation system capable of producing polypeptides in high yield. Science 242: 1162-1164.
17. Endo, Y., Sawasaki, T. (2006) Cell-free expression systems for eukaryotic protein production. Curr Opin Biotechnol 17: 373-380.
18. Yokoyama, S. (2003) Protein expression systems for structural genomics and proteomics. Curr Opin Chem Biol 7: 39-43.
19. Yokoyama, S., Terwilliger, T. C., Kuramitsu, S., Moras, D., Sussman, J. L. (2007) RIKEN aids international structural genomics efforts. Nature 445: 21.

20. Klammt, C., Schwarz, D., Fendler, K., Haase, W., Dotsch, V., et al. (2005) Evaluation of detergents for the soluble expression of alpha-helical and beta-barrel-type integral membrane proteins by a preparative scale individual cell-free expression system. FEBS J 272: 6024-6038.
21. Ishihara, G., Goto, M., Saeki, M., Ito, K., Hori, T., et al. (2005) Expression of G protein coupled receptors in a cell-free translational system using detergents and thioredoxin-fusion vectors. Protein Expr Purif 41: 27-37.
22. Columbus, L., Lipfert, J., Klock, H., Millett, I., Doniach, S., et al. (2006) Expression, purification, and characterization of *Thermotoga maritima* membrane proteins for structure determination. Protein Sci 15: 961-975.
23. Savage, D. F., Anderson, C. L., Robles-Colmenares, Y., Newby, Z. E., Stroud, R. M. (2007) Cell-free complements in vivo expression of the *E. coli* membrane proteome. Protein Sci 16: 966-976.
24. Jasti, J., Furukawa, H., Gonzales, E. B., Gouaux, E. (2007) Structure of acid-sensing ion channel 1 at 1.9 A resolution and low pH. Nature 449: 316-323.
25. Kawate, T., Gouaux, E. (2006) Fluorescence-detection size-exclusion chromatography for precrystallization screening of integral membrane proteins. Structure 14: 673-681.
26. Grisshammer, R., White, J. F., Trinh, L. B., Shiloach, J. (2005) Large-scale expression and purification of a G-protein-coupled receptor for structure determination—an overview. J Struct Funct Genomics 6: 159-163.
27. Cherezov, V., Rosenbaum, D. M., Hanson, M. A., Rasmussen, S. G., Thian, F. S., et al. (2007) High-resolution crystal structure of an engineered human beta2-adrenergic G protein-coupled receptor. Science 318: 1258-1265.
28. Rasmussen, S. G., Choi, H. J., Rosenbaum, D. M., Kobilka, T. S., Thian, F. S., et al. (2007) Crystal structure of the human beta2 adrenergic G-protein-coupled receptor. Nature 450: 383-387.
29. Rosenbaum, D. M., Cherezov, V., Hanson, M. A., Rasmussen, S. G., Thian, F. S., et al. (2007) GPCR engineering yields high-resolution structural insights into beta2-adrenergic receptor function. Science 318: 1266-1273.
30. Spehr, M., Gisselmann, G., Poplawski, A., Riffell, J. A., Wetzel, C. H., et al. (2003) Identification of a testicular odorant receptor mediating human sperm chemotaxis. Science 299: 2054-2058.
31. Reeves, P. J., Callewaert, N., Contreras, R., Khorana, H. G. (2002) Structure and function in rhodopsin: high-level expression of rhodopsin with restricted and homogeneous N-glycosylation by a tetracycline-inducible N-acetylglucosaminyltransferase I-negative HEK293S stable mammalian cell line. Proc Natl Acad Sci USA 99: 13419-13424.
32. Oprian, D. D., Molday, R. S., Kaufman, R. J., Khorana, H. G. (1987) Expression of a synthetic bovine rhodopsin gene in monkey kidney cells. Proc Natl Acad Sci USA 84: 8874-8878.
33. Biacore (2003) Biacore sensor surface handbook (Biacore Uppsala, Sweden).
34. Karlsson, R., Kullman-Magnusson, M., Hamalainen, M. D., Remaeus, A., Andersson, K., et al. (2000) Biosensor analysis of drug-target interactions: direct and competitive binding assays for investigation of interactions between thrombin and thrombin inhibitors. Anal Biochem 278: 1-13.
35. Myszka, D. G. (1999) Improving biosensor analysis. J Mol Recognit 12: 279-284.

Example 11

Expression and Purification of Synthetic Human Olfactory Receptor 17-4 from an Inducible Mammalian Cell Line In order to begin to study the structural and functional mechanisms of olfactory receptors, methods for milligram-scale purification are required. Here we demonstrate the production and expression of a synthetically engineered human olfactory receptor hOR17-4 gene in a stable tetracycline-inducible mammalian cell line (HEK293S). The OR gene was fabricated from scratch using PCR-based gene-assembly, which facilitated codon optimization and attachment of a 9-residue bovine rhodopsin affinity tag for detection and purification. Induction of adherent cultures with tetracycline together with sodium butyrate led to hOR17-4 expression levels of ~30 μg per 150 mm tissue culture plate. Fos-choline-based detergents proved highly capable of extracting the receptors, and fos-choline-14 (N-tetradecylphosphocholine) was selected for optimal solubilization and subsequent purification. Analysis by SDS-PAGE revealed both monomeric and dimeric receptor forms, as well as higher MW oligomeric species. A two-step purification method of immunoaffinity and size exclusion chromatography was optimized which enabled 0.13 milligrams of hOR17-4 monomer to be obtained at >90% purity. This high purity of hOR17-4 is not only suitable for secondary structural and functional analyses but also for subsequent crystallization trials. Thus, this system demonstrates the feasibility of purifying milligram quantities of the GPCR membrane protein hOR17-4.

Introduction

Membrane proteins are of vital importance to life, as evidenced by the fact that ~30% of the genes in almost all sequenced genomes code for membrane proteins [1-3]. However, our understanding of the structures and functions of membrane proteins has lagged behind the known soluble proteins. As of June 2008, there are only 160 unique membrane protein structures known [http://blanco.biomol.uci.edu/Membrane_Proteins_xtal.html], which constitutes less than 1% of all known protein structures. The major bottleneck in obtaining membrane protein structures is the notorious difficulty involved in expressing and purifying the large quantities of membrane protein sample required for X-ray crystallography. In order to accelerate membrane protein structural and function studies, new and simple methods for membrane protein production must be developed.

Olfactory receptors (or odorant receptors) are an extremely large class of G-Protein Coupled Receptors (GPCRs) that function together combinatorially to allow discrimination between a wide range of volatile molecules [4,5]. All GPCRs are integral membrane proteins with seven transmembrane domains arranged in a barrel-like conformation. In olfactory receptors, it is believed that this configuration forms a funnel-shaped pocket for odorant recognition [6]. The olfactory receptor (OR) gene family constitutes the largest single class of genes in the vertebrate genome (2-3% in the human). Current estimates put the number of human olfactory receptor genes at 636, with only 339 being functional and the rest being non-functional pseudogenes [7]. This is considerably less than the mouse OR gene family of 1209 (913 functional) [8] or the canine OR gene family of roughly 1200 (~1000 functional) [9]. Despite the fact that they represent the largest class of known membrane proteins, no detailed structure exists for any olfactory receptor and the functional mechanisms of these amazing receptors remains unknown. The crucial first step to enable such pivotal studies is to engineer systems with the capacity to generate and purify milligram quantities of an olfactory receptor.

Mammalian olfactory receptors are expressed on the cilia of olfactory neurons within the nasal cavity. Odorant binding and recognition leads to activation and release of the olfactory G-protein $G_{olf}$, which triggers cyclic-AMP production, ion-channel-mediated $Ca2+$ influx, and finally the firing of an action potential into the olfactory bulb to be interpreted by the brain [10]. Through an unknown mechanism of allelic inactivation, every olfactory neuron chooses a single OR gene to express. Signals from neurons that express the same olfactory receptor later converge downstream at neural foci called glomeruli [11]. As the same odorant will stimulate multiple ORs (and to various strengths), the brain receives a spatial map of receptor activity through these glomeruli [12]. Odorants are thought to be recognized by matching a specific spatial pattern (a combinatorial code) [5].

The human olfactory receptor 17-4 (hOR17-4, alternately known as OR1D2) is of particular interest since, in addition to olfactory neurons, it is also expressed on the midpiece of human spermatozoa [13]. Sperm expressing hOR17-4 were found to migrate towards known hOR17-4-responsive odorants such as bourgeonal. Thus the receptor serves a dual role in that it recognizes odorants in the nose as well as plays a potential role in sperm chemotaxis and fertilization. As structural studies of hOR17-4 would not only provide information crucial to understanding the molecular mechanism(s) of olfaction but also have application to human reproduction, we selected this receptor as our prototype OR for expression and purification trials.

The GPCR family represents one of the most important known receptor classes as evidenced by the fact that half of all pharmaceutical drugs target GPCRs [14]. Despite their crucial role in mediating such diverse physiological processes as sight, smell, and the response to hormones and neurotransmitters, extremely little is known about these receptors at the structural level. A major breakthrough in 2007 was the determination of only the second GPCR crystal structure—that of a highly engineered human beta2-adrenergic receptor expressed in Sf9 insect cells [15, 16]. Rhodopsin is perhaps the only GPCR that can be easily extracted from tissue, and this may explain why it was the first GPCR to have a detailed structure determined [17-19]. However, recent advances in the Khorana laboratory have led to the development of specific mammalian HEK293 cell lines for heterologous expression as well as methods for purification that yield milligram quantities of functional rhodopsin which is suitable for functional analysis and structural study [20-22]. Here we show that this system can be adapted to facilitate the production and purification of another GPCR, the human olfactory receptor 17-4.

In order to carry out biochemical and structural analyses of olfactory receptors as well as engineer olfactory receptor-based biosensor devices, large quantities of receptors are required. Here we here report inducible expression, large-scale production of human olfactory receptor hOR17-4. We bioengineered the synthetic hOR17-4 gene into 50 oligonucleotide fragments, self-assembled them through high cycle PCR and inserted the assembled gene into an inducible human embryonic kidney cell line (HEK293S). We then induced its production using a combination of tetracycline and sodium butyrate. After systematic detergent screening, the zwitterionic detergent fos-choline-14 (FC14) was found to be most effective for solubilization and was subsequently used throughout the entire solubilization and purification. To our knowledge this is the first time an olfactory receptor has been purified from a mammalian cell line.

Results
Construction of Synthetic hOR17-4 Gene

To fabricate synthetic gene constructs we utilized a PCR-based method of gene synthesis [23] that involves parsing the DNA sequence into a set of small overlapping oligonucleotides. During an initial assembly PCR, these oligos function as both primer and template, while the DNA polymerase successively builds longer and longer fragments with each round of PCR. A second amplification PCR then enriches for the full-length gene. This process has more recently become known as PCA, or polymerase construction and amplification. To assist in parsing the sequence into oligos, we used the online program DNAWorks (http://helixweb.nih.gov/dnaworks) developed by Hoover and Lubkowski [24]. The 312 amino acid sequence of wild-type human olfactory receptor hOR17-4 was obtained from GenBank and directly inputted into the software in protein mode. To adapt the resulting gene for use in our specific expression system and to facilitate purification and detection, the reverse-translated DNA sequence was human codon-optimized and appended with a C-terminal rho1D4 epitope tag (TETSQVAPA (SEQ ID NO: 50)) [20-22]. The synthetic DNA corresponding to the hOR17-4 gene consisted of 1004 bp, encoding a receptor protein of 323 amino acids (FIG. 19). Other than the addition of the rho1D4 tag and linker, the hOR17-4 protein sequence is wild-type and completely full length. Noteworthy in the synthesis procedure was the requirement for a high number of PCR cycles (45) during the assembly PCR, presumably due to inefficiencies resulting from non-productive oligo mispairings.

Induction of hOR17-4 Expression in Stable HEK293S Cell Lines

Figure 20A:
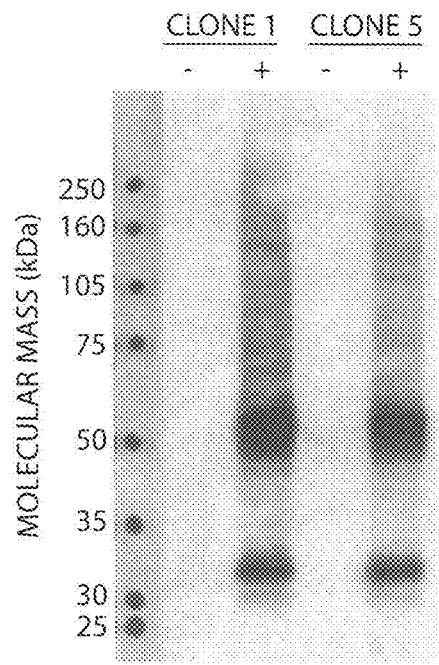

To minimize the toxic effects of receptor overexpression, stable hOR17-4-inducible HEK293S cell lines were created using the Invitrogen T-REx tetracycline regulation system (Materials and Methods). This allowed large-scale cell culture batches to be grown and then, when desired, concerted production of fresh olfactory receptor to be induced in nearly 100% of the cells. Results for the induction of hOR17-4 expression in two of the subcloned HEK293 lines are shown in FIG. 20A. Western immunoblotting using a monoclonal antibody against the rho1D4 tag revealed major immunoreactive bands at approximately 32 kD and 60 kD, which correspond in size to monomeric and dimeric forms of the hOR17-4 receptor. This size pattern has been reported previously for several solubilized olfactory receptors expressed in Sf9 and mammalian cells [25-27]. Larger molecular weight complexes were also present, presumably due to aggregation and precipitation of the receptor. As sample boiling only increases the precipitation, it is possible that increased temperatures (above 4° C.) caused by the electrophoresis could be causing the receptor to partially aggregate. Thus these high MW species could be a side effect of the SDS-PAGE electrophoresis and not originally present in the solubilized receptor fractions.

Figure 20B:
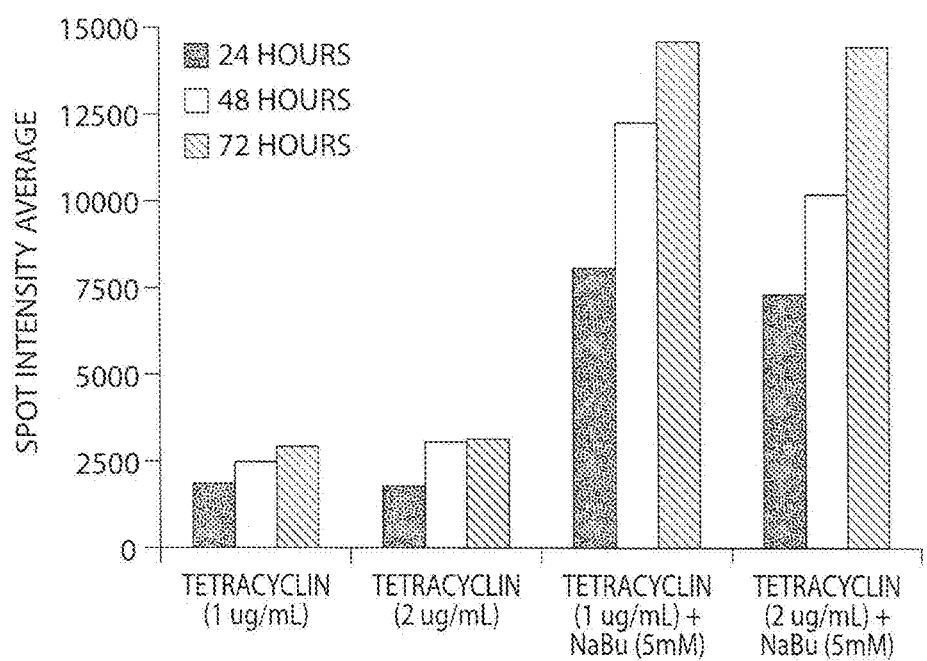

The histone deacetylyase inhibitor sodium butyrate has been demonstrated to synergistically enhance expression when used with tetracycline-regulated systems [21]. Induction of hOR17-4 in HEK293S cells using tetracycline in conjunction with sodium butyrate increased expression by approximately 4-5 fold over tetracycline alone at all time points tested (FIG. 20B). There was no detectable expression of hOR17-4 in the absence of tetracycline or with sodium butyrate alone. Significant cell toxicity and death was observed in treatments combining tetracycline and sodium butyrate (5 mM) at the 48 and 72 hours time points. Treatment with sodium butyrate or tetracycline alone did not show this toxicity, indicating it to be a result of the high level expression induced by the drugs in conjunction.

Figure 21B:
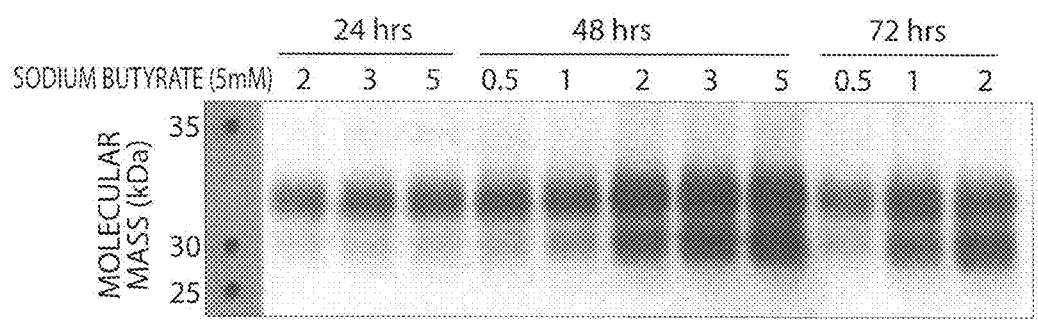

To characterize this effect the samples were subjected SDS-PAGE analysis (FIG. 21A). The gel showed two monomer band sizes, approximately 30 kD and 32 kD, suggesting distinct monomer forms (and corresponding dimer forms). It is possible these size discrepancies are due to differences in glycosylation of the receptor. Sodium butyrate addition for 24 hours showed a very large increase in expression over tetracycline alone, with the monomer band running at approximately 32 kD. Sodium butyrate addition for longer periods further increased total expression, however this caused the appearance of the additional monomer form running at 30 kD. The 48 hour time point contained roughly equal parts of both forms while the 72 hour time point consisted predominantly of the 30 kD form. To attempt to avoid the aforementioned toxicity we next performed a time course using a range of sodium butyrate concentrations (FIG. 21B). We discovered that high levels of expression appeared to correlate with the appearance of the 30 kD form (and correspondingly smaller dimer form) and the observed cytotoxicity noted previously.

For subsequent purification experiments, we selected a treatment consisting of sodium butyrate (1 mM) with tetracycline (1 µg/ml) for 48 hours for attempts to purify primarily the 32 kD form. However, to further compare and characterize both forms, increasing the sodium butyrate concentration to 5 mM could be used, as relatively equal amounts of both monomer forms would be present.

Purification of Heterologously Expressed hOR17-4

Figure 22B:
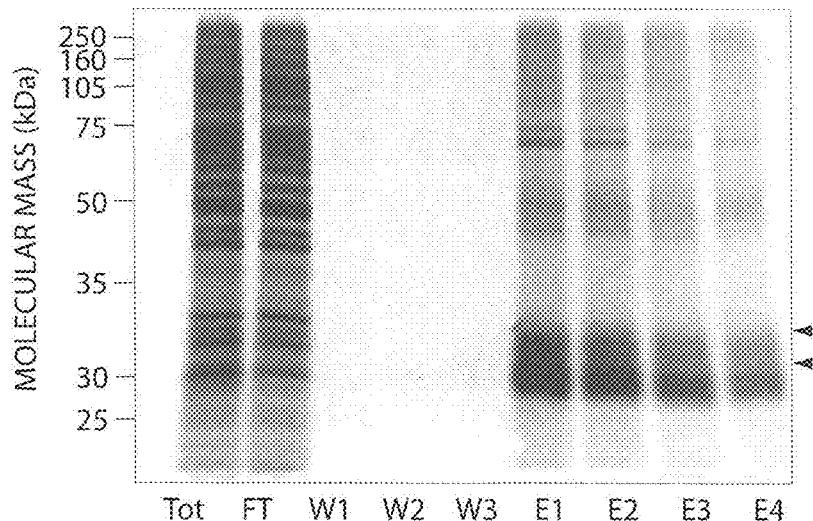

We incorporated a C-terminal rho1D4-tag utilized by the Khorana lab for rhodopsin purification and detection [20-22], namely the nine C-terminal amino acid sequence (TETSQVAPA (SEQ ID NO: 50)) against which a specific monoclonal antibody has been generated (rho1D4). This tag has already facilitated early-stage immunoaffinity purifications of several other GPCRs and membrane proteins [28-31]. For the initial immunoaffinity purification, we used CNBr-activated Sepharose 4B beads linked to the mouse monoclonal rho1D4 antibody to capture detergent solubilized receptors [21]. We first performed a small scale purification from six 150 mm culture plates of hOR17-4-inducible HEK293S cells. The plates were treated as to have equal amounts of the 30 kD and 32 kD bands upon harvesting (tetracycline plus 5 mM sodium butyrate, 48 hours). Following a thorough wash procedure to remove non-specific impurities, the bound receptors were eluted by the addition of an excess of epitope peptide (TETSQVAPA (SEQ ID NO: 50)). Fractions were subjected to SDS-PAGE followed by either western immunoblotting (FIG. 22A) or total protein staining using highly-sensitive SYPRO-Ruby (FIG. 22B). The receptor was completely captured by the bead matrix, as no hOR17-4 was detected in the flow through by western blot. The bound OR eluted primarily in the first and second elution fractions. Total yield of hOR17-4 was approximately 30 µg per 150 mm plate. Mass spectrometry analysis on samples isolated from SDS-PAGE gel bands confirmed the identity of putative monomer and dimer protein bands as hOR17-4 receptor (see Materials and Methods).

Figure 23B:
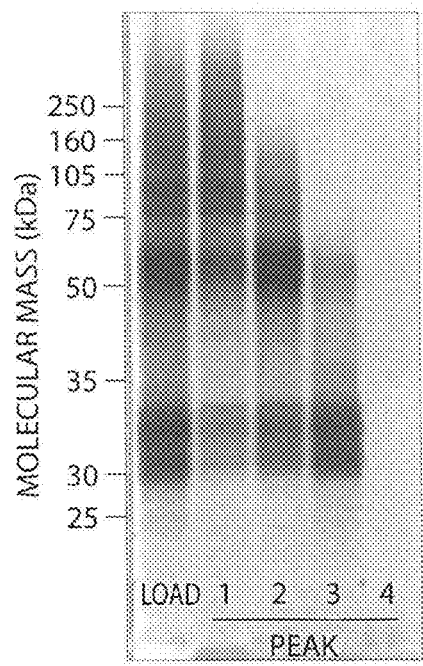

To expand the system to potential milligram scale, fifty 150 mm culture plates of hOR17-4-inducible HEK293S cells were used. The plates were treated tetracycline plus 5 mM sodium butyrate, 48 hours). The total yield of hOR17-4 following immunoaffinity purification was 1.5 milligrams. To further purify the receptor and to remove the elution peptide, the hOR17-4 was subjected to size exclusion chromatography (SEC) using a gel filtration column on an Äkta HPLC system. Column flowthrough was monitored by UV absorption (280 nm and 215 nm) and separated into fractions by an auto-fraction collector. As seen in FIG. 23A, five distinct peaks were observed. The peak fractions were then pooled, concentrated and subjected to SDS-PAGE followed by total protein staining. As seen in FIG. 23B, peak 3 contains monomeric hOR17-4 (>90% purity) while earlier peaks contained largely dimeric (peak 2) and aggregated/oligomerized (peak 1) forms. Peak 4 showed no visible protein and peak 5 corresponds to the residual elution peptide (TETSQVAPA (SEQ ID NO: 50)) from the immunoaffinity purification. The final yield of purified hOR17-4 monomer was 0.13 milligrams (2.6 µg per plate). Thus, using a two-step procedure we have successfully obtained significant amounts of hOR17-4 in a highly pure form.

Discussion

In this study, we successfully developed methods for the construction of inducible mammalian cell lines that generate large quantities of olfactory receptor on demand. To our knowledge this is the first olfactory receptor to be purified from a mammalian cell line. Currently, we have demonstrated the production of the human olfactory receptor hOR17-4 in a stable tetracycline-inducible human embryonic kidney cell line (HEK293S). Expressed OR genes were fabricated from scratch using PCR-based gene synthesis (polymerase construction and amplification, aka PCA), which facilitated codon optimization for high level expression and attachment of affinity tags for detection and purification. The HEK293S cells can be grown and OR expression induced in adherent cultures (yield of ~30 micrograms/150-mm plate). Using methods originally adapted from the production and purification of the GPCR rhodopsin [20-22] and further optimized (including the full-spectrum screening of over 70 detergents), the olfactory receptor is solubilized and extracted from the cells using fos-choline-14. The OR protein is then isolated using a two-step purification method (immunoaffinity followed by size-exclusion chromatography) which yields hOR17-4 monomer at greater than 90% purity (FIG. 23B).

There have been a host of previous studies that have expressed and studied olfactory receptors in native and heterologous systems. However, to date there has not been a case where olfactory receptors have been overexpressed and purified to homogeneity in significant quantities. While purification of ORs has been attempted in bacterial [32] and Sf9 insect systems [25, 26], these were unable to produce large quantities of native full-length olfactory receptor. Additionally, these organisms lack mammalian post-translational machinery and thus purified receptors may be improperly folded or missing critical modifications. It is known that most, if not all, GPCRs are glycosylated, and indeed the olfactory receptors have conserved N-linked glycosylation sites (Asn-X-Ser/Thr) at their N-terminus [33, 34]. Several studies have indicated that loss of glycosylation can lead to improper folding and targeting, resulting in decreased function and compromised structure [35, 36]. Loss of either N-terminal glycosylation site (Asn-2 or Asn-15) of rhodopsin is sufficient to cause loss of signal transduction despite no apparent change in localization or folding [37, 38]. This indicates that purification of olfactory receptors from mammalian systems might be crucial for functional expression and purification.

Characterization of Purified hOR17-4

It is interesting to note that the engineered hOR17-4-rho protein (with theoretical molecular mass of 36.2 kD) migrates slightly faster than expected on SDS-PAGE gels (30 kD and 32 kD). One possible explanation for this discrepancy is incomplete receptor denaturation by SDS since boiling the samples results in aggregation. Indeed, many other membrane proteins have been found to migrate faster than their actual size on SDS-PAGE, and this has been reported for other olfactory receptors as well [26, 32]. We believe both monomer forms of the expressed hOR17-4 receptor to be intact, full-length proteins as evidenced by: 1) detection by the C-terminal rho1D4 monoclonal antibody, 2) detection by custom anti-hOR17-4 polyclonal antibodies raised against the hOR17-4 N-terminus or C-terminus, 3) detection of a 30 kD N-terminally 6×His-tagged hOR17-4 variant using anti-His antibodies (data not shown). Additionally, we see only the 32 kD form at low levels of induction while the kD form only begins to appear at higher levels of induction. One explanation is that the receptor is glycosylated at low induction but that the toxicity associated with higher expression causes the receptor to begin to accumulate in the ER and not be properly processed.

The appearance of two distinct hOR17-4 monomer bands following purification could pose a problem for structural studies using X-ray crystallography, since typically a high degree of protein homogeneity is required for protein crystallization. We initially believed that it was possible to obtain primarily 32 kD form using lower levels of induction (FIG. 21B). However, we have observed that the rho1D4 immunoaffinity purification appears to increase the proportion of 30 kD monomer form relative to 32 kD form given the original treatment. For example, the treatment dosages for the small-scale (FIG. 22) and large-scale (FIG. 23) purifications were chosen (based on data in FIG. 21b) to result in equal amounts of both forms or primarily 32 kD form, respectively. However, following immunoaffinity purification the resulting elution samples were enriched in the 30 kD monomer form. One hypothesis is that the 30 kD (potentially non-glycosylated form) binds more readily to the rho1D4-coupled bead matrix. Therefore, to obtain truly homogeneous hOR17-4 monomer it might be necessary to use even lower levels of induction where no 30 kD form exists. Another option would be to mutate the asparagine in the consensus N-glycosylation site of the receptor, located at amino acid position 5. We predict such a change to result in exclusive production of the 30 kD monomer form. However, the functional effect of abolishing glycosylation on the receptor is unknown.

There have been numerous reports in the literature citing difficulties in expressing functional olfactory receptors in heterologous systems. The main problem seems to be improper membrane targeting and resulting cytosolic localization of the majority of ORs [34, 35, 39, 40]. Several studies have been able to alleviate this problem by the addition of putative membrane import signals to the N-terminus of the olfactory receptor [41, 42]. However, more recent studies [43, 44] have expressed functional olfactory receptors in HEK293 cells without the use of such signal tags. We also investigated the use of an N-terminal "membrane import" sequence composed of the first twenty amino acids of bovine rhodopsin but found no significant increase in receptor yield or localization (results not shown).

Our largest adherent culture experiment consisted of fifty 150 mm tissue culture plates. While the total yield of crude hOR17-4 following immunoaffinity purification was 1.5 milligrams, the subsequent size exclusion chromatography and associated concentration steps reduced this yield to 0.13 milligrams of purified hOR17-4 monomer (2.6 µg per plate). The monomer was >90% pure, with the only other major contaminating band consisting of hOR17-4 dimer. While this represents a significant milestone, using adherent culture for milligram-scale purification of the receptor monomer poses a substantial challenge. However, the HEK293S cell line is capable of suspension culture, and we plan to scale-up purification yields by adapting the system to culture in a large volume (5-10 liter) liquid bioreactor. The high cell densities allowed should allow the production and subsequent purification of milligram quantities of olfactory receptors, which will be necessary for future experiments in determining receptor structure and function.

General Application for the Purification of Other Olfactory Receptors

Here we show that a GPCR olfactory receptor gene can be designed, synthesized, placed into an inducible mammalian expression system and the resulting full-length protein purified to near homogeneity in a two-step process. In addition to our experiments on hOR17-4, we have constructed optimized synthetic genes for several mouse olfactory receptors and initial expression trials have proven successful. The small size of the rho1D4 tag and its extremely mild elution conditions provide a minimum of disruption to the purified protein. In contrast to previous attempts at OR purification using bacterial systems which required fusion to GST and truncated or mutated OR protein sequences [32], the system described here allows for the production of full-length wild-type OR. The application of this technique to other olfactory receptors could feasibly lead to a generalized method for obtaining large quantities of any olfactory receptor in a rapid and simple manner. Such methods could prove extremely useful in elucidating the structural and functional mechanism(s) of olfactory receptors and in their integration into OR-based biosensor devices.

Experimental Procedures

Experimental Procedures

Gene Construction—

The protein sequence for hOR17-4 (also known as OR1D2) was obtained from GenBank (NCBI Accession # NP002539). DNAWorks online software (http://helixweb.nih.gov/dnaworks) was used in protein mode to design the synthetic gene and parse it into an oligonucleotide set. To adapt the synthetic hOR17-4 olfactory receptor gene for use in mammalian cell expression and purification, the following sequence modifications were made: i) human codon optimization; ii) addition of a C-terminal rho1D4 epitope tag (TETSQVAPA (SEQ ID NO: 50)) preceded by a two glycine linker to facilitate detection and purification; iii) addition of a Kozak consensus sequence (GCCACCACC (SEQ ID NO: 53)) immediately 5' to the ATG start codon; iv) addition of an EcoRI restriction site at the 5' end and a NotI restriction site at 3' end of the gene to enable cloning into expression vectors. The synthetic hOR17-4 gene consisted of 1004 bp, of which 969 by code for the 323 amino acid hOR17-4-GlyGly-rho1D4 protein. The designed oligonucleotide primers were purchased from IDT (Coralville, Iowa) with a maximum length of 45 bp. PCR-based gene synthesis was performed using a 2-step assembly/amplification protocol [45] with the exception that the assembly PCR was run for 45 cycles. PCR reactions were then analyzed by gel electrophoresis and stained with ethidium bromide. Full length product was excised, extracted, and then digested with the pertinent restriction enzymes. The genes were then ligated into the T-REx pcDNA4/To inducible expression plasmid (Invitrogen, Carlsbad, Calif.), sequenced, and a correct clones grown up using a MaxiPrep kit (Qiagen, Valencia, Calif.). The plasmid containing the optimized hOR17-4 gene was designated pcDNA4/To-hOR17-4-rho1D4.

Generation of Stable Inducible Cell Lines—

HEK293S (suspension adapted HEK293 cells) containing the stable expression of pcDNA6/Tr (Invitrogen) which encodes the Tet repressor protein (TetR) had previously been generated and cloned [21]. HEK293S cell monolayers were grown in DMEM/F12 with GlutaMAX (Invitrogen catalog

10565-042) supplemented with fetal bovine serum (10%), HEPES (15 mM), non-essential amino acids (0.1 mM), sodium pyruvate (0.5 mM), penicillin (100 units/ml), streptomycin (100 µg/ml) and grown at 37° C. at 5% $CO_2$. All tissue culture and media components were purchased from Invitrogen unless otherwise noted. The pcDNA4/To-hOR17-4-rho1D4 plasmid was then transfected into these cells using Lipofectamine 2000 and after 48 hours cells were subjected to drug selection in 5 µg/ml blasticidin and 250 µg/ml zeocin for 2 weeks and then subcloned. 28 colonies were expanded and screened for inducible expression using media supplemented with or without 1 µg/ml tetracycline for 48 hours. Samples were then scrape harvested, solubilized in phosphate buffered saline (PBS) with 2% w/v Fos-Choline-14 (Anatrace, Maumee, Ohio) and Complete Protease Inhibitor Cocktail (Roche, Basel, CH) for 1 hour at 4° C. Expression was assayed via dot blotting and SDS-PAGE western blotting using the mouse monoclonal antibody rho1D4. Clone 5, the colony showing the best expression of hOR17-4 under induction conditions while maintaining undetectable expression without induction, was selected and expanded into large-scale culture and used for all subsequent experiments. The hOR17-4-inducible HEK293S cell line was maintained using 5 µg/ml blasticidin and 250 µg/ml zeocin.

Cell Extract Preparation—

Buffers used were as follows: PBS buffer: 137 mM NaCl, 2.7 mM KCl, 1.8 mM $KH_2PO_4$, 10 mM $Na_2HPO_4$ (pH 7.4); Solubilization buffer: PBS containing Complete Protease Inhibitor Cocktail (Roche, Basel, Switzerland) and 2% wt/vol FC14; and Wash buffer: PBS containing 0.2% FC14; Elution buffer: Wash buffer containing 100 µM Ac-TETSQVAPA-$CONH_2$ (SEQ ID NO: 50) elution peptide. The detergent FC14 was purchased from Anatrace (Maumee, Ohio). Sodium butyrate was purchased from Sigma (Saint Louis, Mo.).

For initial dosage and time course experiments, hOR17-4-inducible HEK293S cells were grown to 80-90% confluency at 37° C. in 6-well tissue culture plates, treated as indicated and then scrape harvested into ice-cold PBS containing Complete Protease Inhibitor Cocktail. The hOR17-4 was then solubilized by resuspending the cell pellets in 150 µl solubilization buffer and rotating for 1 hour at 4° C. The non-solubilized fraction was then pelleted using at 13,000 g for 30 minutes. The supernatant was then removed and analyzed by SDS-PAGE.

For purification experiments, up to fifty 150 mm tissue culture plates were used per experiment. Briefly, hOR17-4-inducible HEK293S cells were seeded at a density of $5\times10^6$ cells per 150 mm dish and grown for 72 hours at 37° C., at which point they reached 80-90% confluency. The cells were then induced with medium containing tetracycline (1 µg/ml) plus sodium butyrate (as indicated). After 48 hours, the cells were harvested by scraping (at 4° C.) each plate into 2 ml PBS containing Complete Protease Inhibitor Cocktail. The cells were then pooled and snap frozen in liquid nitrogen and stored at −80° C. until purification was carried out. On the day of purification, cells were thawed on wet ice and spun down by centrifugation at 4000 g for 1 minute. All further steps were performed at 4° C. unless noted. The hOR17-4 was then solubilized by resuspending the cells in solubilization buffer (1-2 ml per 150 mm plate) and rotating for 4 hours. The non-solubilized fraction was then pelleted using an ultracentrifuge at >100,000 g for 30 minutes. The resulting supernatant was removed and put at 4° C. A small amount of supernatant (100 µl) was set aside, labeled "total lysate" and stored at −20° C. The remainder was directly applied to immunoaffinity purification.

Immunoblotting and Total Protein Staining—

Samples were assayed via polyacrylamide gel electrophoresis (SDS-PAGE) under both reducing and denaturing conditions. Samples were prepared and loaded according to standard Novex gel protocols with the exception that the samples were incubated at room temperature prior to loading, as boiling caused membrane protein aggregation. Full Range Rainbow (GE Healthcare, Waukesha, Wis.) molecular weight marker was loaded as the protein size standard. Samples were resolved on Novex 10% Bis-Tris SDS-PAGE gels (Invitrogen) were run using NuPAGE MOPS buffer at 100V and were subsequently transferred to a 0.45 µm nitrocellulose membrane and subjected to western immunoblotting using the rho1D4 as primary antibody, followed by a secondary HRP-linked goat anti-mouse IgG (Pierce, Rockford, Ill.) and detection using the ECL-Plus Kit (GE Healthcare). For total protein staining, SDS-PAGE gels were run as above, stained using SYPRO-Ruby (a more sensitive alternative to Coomassie; Invitrogen), and visualized by fluorescence using UV transillumination (excitation wavelength 300 nm). All western blot and SYPRO-Ruby images were captured using a Fluor Chem gel documentation system (Alpha Innotech, San Leandro, Calif.).

Immunoaffinity Purification—

For immunoaffinity purification we utilized rho1D4 monoclonal antibody (Cell Essentials, Cambridge, Mass.) chemically linked to CNBr-activated Sepharose 4B beads (GE Healthcare). The rho1D4 elution peptide Ac-TETSQVAPA-$CONH_2$ (SEQ ID NO: 50) was synthesized by CBC Scientific (San Jose, Calif.). Rho1D4-sepharose immunoaffinity purification has been described previously [21]. Briefly, the cell extract supernatant was mixed with rho1D4-coupled sepharose bead slurry (binding capacity 0.7 mg/ml) and rotated overnight at 4° C. to capture the rho1D4-tagged olfactory receptors. The beads were then pelleted by centrifugation at 2000 g for one minute and the supernatant collected, labeled as "flow-through" and saved for future analysis. The beads were then resuspended in 100 bead volumes of cold wash buffer (PBS+0.2% Fos-Choline-14), rotated for 10 minutes at 4° C., then repelleted. A total of five washes were carried out and 100 µl of each sequential wash was saved for subsequent analysis. After the final wash, the beads were pelleted again and transferred to a new tube for elution. A series of five elutions (each rotated 1 hour at room temperature) was then carried out, each using 1 bead volume of elution buffer (PBS+0.2% FC14+100 µM TETSQVAPA (SEQ ID NO: 50) peptide). Total protein concentration was measured using BCA assay (Pierce).

Mass Spectrometry—

Immunoaffinity-purified samples of hOR17-4 were seperated via SDS-PAGE, stained with SYPRO-Ruby and gel bands at 30 kD, 32 kD, and 60 kD were excised into sterile, methanol-rinsed microcentrifuge tubes. The samples subjected to trypsin digestion and the resulting fragments analyzed by Ion Trap LCMS for protein identification by the MIT Biopolymers Laboratory (Cambridge, Mass.). All bands were identified as hOR17-4, indicating monomeric and dimeric forms.

Size Exclusion Chromatography—

For further purification, hOR17-4 proteins were subjected to gel filtration chromatography using a HiLoad 16/60 Superdex 200 column on an Äkta Purifier HPLC system (GE Healthcare). The column was first equilibrated using wash buffer (PBS+0.2% w/v Fos-Choline-14). Pooled hOR17-4 elution fractions from the rho1D4 immunoaffinity purification were concentrated to 0.75 mg/ml using a 10 kD MWCO filter column (Millipore, Billerica, Mass.) and then applied to the Äkta system. After loading, the column was run with wash buffer at 1 ml/min and column flowthrough monitored via UV absorbance at 280 nm and 215 nm. Protein fractions were collected using an automated fraction collector. Peak fractions were then pooled, concentrated and subjected to SDS-PAGE and analysis via Sypro Ruby staining Total protein concentration was measured using BCA assay (Pierce).

PCR-Based Gene Synthesis.

Fabrication of the custom hOR17-4 gene was accomplished using a two-step PCR method using an overlapping oligonucleotide set designed using DNAWorkds. (A) The first step is an assembly PCR in which all oligos function as both primer and template to effectively extend their 3' ends with successive PCR cycles. After many cycles of assembly, the full-length gene is constructed. However, the assembly reaction contains not only full-length product but also a mixture of all other extended oligos. Thus a second PCR reaction (B) is performed using a small amount of the assembly PCR reaction as template and the two terminal oligos (oligos A and L) as primers in order to selectively amplify the full-length gene product.

The primers used for PCR are described in Cook et al. (2008). Study of a synthetic human olfactory receptor 17-4: Expression and purification from an inducible mammalian cell line. PLoS One 3(8) e2920:1-9, the contents of which are expressly incorporated by reference herein.

REFERENCES

1. Wallin E, von Heijne G (1998) Genome-wide analysis of integral membrane proteins from eubacterial, archaean, and eukaryotic organisms. Protein Sci 7: 1029-1038.
2. Loll P J (2003) Membrane protein structural biology: the high throughput challenge. J Struct Biol 142: 144-153.
3. Nilsson J, Persson B, von Heijne G (2005) Comparative analysis of amino acid distributions in integral membrane proteins from 107 genomes. Proteins 60: 606-616.
4. Buck L, Axel R (1991) A novel multigene family may encode odorant receptors: a molecular basis for odor recognition. Cell 65: 175-187.
5. Malnic B, Hirono J, Sato T, Buck L B (1999) Combinatorial receptor codes for odors. Cell 96: 713-723.
6. Breer H (2003) Olfactory receptors: molecular basis for recognition and discrimination of odors. Anal Bioanal Chem 377: 427-433.
7. Malnic B, Godfrey P A, Buck L B (2004) The human olfactory receptor gene family. Proc Natl Acad Sci USA 101: 2584-2589.
8. Godfrey P A, Malnic B, Buck L B (2004) The mouse olfactory receptor gene family. Proc Natl Acad Sci USA 101: 2156-2161.
9. Olender T, Fucks T, Linhart C, Shamir R, Adams M, et al. (2004) The canine olfactory subgenome. Genomics 83: 361-372.
10. Ebrahimi F A, Chess A (1998) Olfactory G proteins: simple and complex signal transduction. Curr Biol 8: R431-433.
11. Touhara K (2002) Odor discrimination by G protein-coupled olfactory receptors. Microsc Res Tech 58: 135-141.
12. Mombaerts P (1999) Molecular biology of odorant receptors in vertebrates Annu Rev Neurosci 22: 487-509.
13. Spehr M, Gisselmann G, Poplawski A, Riffell J A, Wetzel C H, et al. (2003) Identification of a testicular odorant receptor mediating human sperm chemotaxis. Science 299: 2054-2058.
14. Filmore D (2004) It's a GPCR world. Modern Drug Discovery 7: 24-28.
15. Rasmussen S G, Choi H J, Rosenbaum D M, Kobilka T S, Thian F S, et al. (2007) Crystal structure of the human beta2 adrenergic G-protein-coupled receptor. Nature 450: 383-7.
16. Cherezov V, Rosenbaum D M, Hanson M A, Rasmussen S G, Thian F S, et al. (2007) High-resolution crystal structure of an engineered human beta2-adrenergic G protein-coupled receptor. Science 318: 1258-65.
17. Palczewski K, Kumasaka T, Hori T, Behnke C A, Motoshima H, Fox B A, et al. (2000) Crystal structure of rhodopsin: A G protein-coupled receptor. Science 289: 739-745.
18. Li J, Edwards P C, Burghammer M, VIIIa C, Schertler G F (2004) Structure of bovine rhodopsin in a trigonal crystal form. J Mol Biol 343: 1409-1438.
19. Krebs A, Edwards P C, VIIIa C, Li J, Schertler G F (2003) The three-dimensional structure of bovine rhodopsin determined by electron cryomicroscopy. J Biol Chem 278: 50217-50225.
20. Reeves P J, Thurmond R L, Khorana H G (1996) Structure and function in rhodopsin: high level expression of a synthetic bovine opsin gene and its mutants in stable mammalian cell lines. Proc Natl Acad Sci USA 93: 11487-11492.
21. Reeves P J, Kim J M, Khorana H G (2002) Structure and function in rhodopsin: a tetracycline-inducible system in stable mammalian cell lines for high-level expression of opsin mutants. Proc Natl Acad Sci USA 99: 13413-13418.
22. Reeves P J, Callewaert N, Contreras R, Khorana H G (2002) Structure and function in rhodopsin: high-level expression of rhodopsin with restricted and homogeneous N-glycosylation by a tetracycline-inducible N-acetylglucosaminyltransferase I-negative HEK293S stable mammalian cell line. Proc Natl Acad Sci USA 99: 13419-13424.
23. Stemmer W P, Crameri A, Ha K D, Brennan T M, Heyneker H A (1995) Single-step assembly of a gene and entire plasmid from large numbers of oligodeoxyribonucleotides. Gene 164: 49-53.
24. Hoover D M, Lubkowski J (2002) DNAWorks: an automated method for designing oligonucleotides for PCR-based gene synthesis. Nucleic Acids Res 30: e43.
25. Gat U, Nekrasova E, Lancet D, Natochin M (1994) Olfactory receptor proteins. Expression, characterization and partial purification. Eur J Biochem 225: 1157-1168.
26. Nekrasova E, Sosinskaya A, Natochin M, Lancet D, Gat U (1996) Overexpression, solubilization and purification of rat and human olfactory receptors. Eur J Biochem 238: 28-37.
27. Katada S, Nakagawa T, Kataoka H, Touhara K (2003) Odorant response assays for a heterologously expressed olfactory receptor. Biochem Biophys Res Commun 305: 964-969.
28. Shimada M, Chen X, Cvrk T, Hilfiker H, Parfenova M, et al. (2002) Purification and characterization of a receptor for human parathyroid hormone and parathyroid hormone-related peptide. J Biol Chem 277: 31774-31780.
29. Farrens D L, Dunham T D, Fay J F, Dews I C, Caldwell J, et al. (2002) Design, expression, and characterization of a synthetic human cannabinoid receptor and cannabinoid receptor/G-protein fusion protein. J Pept Res 60: 336-347.
30. Liu B, Krieger M (2002) Highly purified scavenger receptor class B, type I reconstituted into phosphatidylcholine/cholesterol liposomes mediates high affinity high density lipoprotein binding and selective lipid uptake. J Biol Chem 277: 34125-34135.

31. Chelikani P, Reeves P J, Rajbhandary U L, Khorana H G (2006) The synthesis and high-level expression of a beta2-adrenergic receptor gene in a tetracycline-inducible stable mammalian cell line. Protein Sci 15: 1433-40.
32. Kiefer H, Krieger J, Olszewski J D, Von Heijne G, Prestwich G D, et al. (1996) Expression of an olfactory receptor in *Escherichia coli*: purification, reconstitution, and ligand binding. Biochemistry 35: 16077-16084.
33. Liu A H, Zhang X, Stolovitzky G A, Califano A, Firestein S J (2003) Motif-based construction of a functional map for mammalian olfactory receptors. Genomics 81: 443-56.
34. Katada S, Tanaka M, Touhara K (2004) Structural determinants for membrane trafficking and G protein selectivity of a mouse olfactory receptor. J Neurochem 90: 1453-1463.
35. Gimelbrant A A, Haley S L, McClintock T S (2001) Olfactory receptor trafficking involves conserved regulatory steps. J Biol Chem 276: 7285-7290.
36. Jayadev S, Smith R D, Jagadeesh G, Baukal A J, Hunyady L (1999) N-linked glycosylation is required for optimal AT1a angiotensin receptor expression in COS-7 cells. Endocrinology 140: 2010-2017.
37. Kaushal S, Ridge K D, Khorana H G (1994) Structure and function in rhodopsin: the role of asparagine-linked glycosylation. Proc Natl Acad Sci USA 91: 4024-4028.
38. Zhu L, Jong G F, Jastrzebska B, Filipek S, Pearce-Kelling S E, et al. (2004) A naturally occurring mutation of the opsin gene (T4R) in dogs affects glycosylation and stability of the G protein-coupled receptor. J Biol Chem 279: 53828-53839.
39. Lu M, Staszewski L, Escheverri F, Xu H, Moyer B D (2004) Endoplasmic reticulum degradation impedes olfactory G-protein coupled receptor functional expression. BMC Cell Biol 5: 34.
40. Lu M, Echeverri F, Moyer B D (2003) Endoplasmic reticulum retention, degradation, and aggregation of olfactory G-protein coupled receptors. Traffic 4: 416-433.
41. Wetzel C H, Oles M, Wellerdieck C, Kuczkowiak M, Gisselmann G, et al. (1999) Specificity and sensitivity of a human olfactory receptor functionally expressed in human embryonic kidney 293 cells and *Xenopus Laevis* oocytes. J Neurosci 19: 7426-7433.
42. Krautwurst D, Yau K W, Reed R R (1998) Identification of ligands for olfactory receptors by functional expression of a receptor library. Cell 95: 917-926.
43. Ivic L, Zhang C, Zhang X, Yoon S O, Firestein S (2002) Intracellular trafficking of a tagged and functional mammalian olfactory receptor. J Neurobiol 50: 56-68.
44. Levasseur G, Persuy M A, Grebert D, Remy J J, Salesse R, et al. (2003) Ligand-specific dose-response of heterologously expressed olfactory receptors. Eur J Biochem 270: 2905-2912.
45. Can P A, Park J S, Lee Y J, Yu T, Zhang S, et al. (2004) Protein-mediated error correction for de novo DNA synthesis. Nucleic Acids Res 32: e162.

Footnotes
[1]The abbreviations: OR(s), olfactory receptor(s); HEK, human embryonic kidney; GPCR(s), G protein-coupled receptor(s); mAb, monoclonal antibody; PCR, polymerase chain reaction; PBS, phosphate-buffered saline; FC14, foscholine-14 (N-tetradecylphosphocholine); SEC, size exclusion chromatography.

Example 12

Large-Scale Production and Study of a Synthetic G Protein-Coupled Receptor: Human Olfactory Receptor 17-4

Although understanding of the olfactory system has progressed at the level of downstream receptor signaling and the wiring of olfactory neurons, the system remains poorly understood at the molecular level of the receptors and their interaction with and recognition of odorant ligands. The structure and functional mechanisms of these receptors still remain a tantalizing enigma, because numerous previous attempts at the large-scale production of functional olfactory receptors (ORs) have not been successful to date. To investigate the elusive biochemistry and molecular mechanisms of olfaction, we have developed a mammalian expression system for the large-scale production and purification of a functional OR protein in milligram quantities. Here we report the study of human OR17-4 (hOR17-4) purified from a HEK293S tetracycline-inducible system. Scale-up of production yield was achieved through suspension culture in a bioreactor, which enabled the preparation of >10 mg of monomeric hOR17-4 receptor following immunoaffinity and size exclusion chromatography, with expression yields reaching 3 mg/L of culture medium. Several key post-translational modifications were identified using MS, and CD showed the receptor to be ~50% α-helix, similar to other recently determined G-protein coupled receptor structures. Using surface plasmon resonance (SPR), detergent-solubilized hOR17-4 specifically bound its known activating odorants lilial and floralozone in vitro. The hOR17-4 also recognized specific odorants in heterologous cells as determined by calcium ion mobilization. Our system is feasible for the production of large quantities of olfactory receptor necessary for structural and functional analyses and research into OR biosensor devices.

Introduction

Animal noses have evolved the ability to rapidly detect a seemingly infinite array of odors at minute concentrations. The basis of this sensitivity are the olfactory (smell) receptors, a large class of G-protein coupled receptors (GPCRs) that function together combinatorially to allow discrimination between a wide range of volatile and soluble molecules (1, 2). As GPCRs, all olfactory receptors (ORs) are integral membrane proteins with 7 predicted transmembrane domains (7™). To date, crystal structures exist for only 5 GPCR proteins (3). Despite the fact that olfactory receptors represent the largest class of known membrane proteins, no detailed structure exists for any OR, as the major obstacle to structural and functional studies on membrane proteins is the notorious difficulty involved in expressing and purifying the large quantities of receptor protein sample required for techniques such as X-ray crystallography. The first crucial step to enable such pivotal biochemical and structural analyses is to engineer systems with the capacity to produce and purify milligram quantities of an olfactory receptor.

hOR17-4 (alternately known as OR1D2) is of particular interest since, in addition to olfactory neurons, it is also expressed on the midpiece of human spermatozoa (4). Sperm expressing hOR17-4 were found to migrate towards known hOR17-4 odorants ligands, such as bourgeonal, lilial, and floralozone (4). Thus the receptor serves a dual role in that it recognizes odorants in the nose as well as plays a potential role in sperm chemotaxis and fertilization. Structural studies of hOR17-4 would not only provide information crucial to understanding the molecular basis of olfaction, but also have application to human reproduction.

We recently developed an OR expression system (5) using stably-inducible mammalian HEK293S (human embryonic kidney) cell lines by optimizing methods originally developed to generate milligram quantities of functional rhodopsin (6-7) In adherent culture, this adapted rho-tag system was used to express and purify monomeric hOR17-4 to >90% purity (5). Here we report that this system can be scaled up using bioreactor culture to facilitate the production and purification of milligram amounts of hOR17-4. Key to the efficient extraction of hOR17-4 was a comprehensive screen of diverse detergents and the selection of zwitter-ionic fos-choline detergents as solubilizing agents, as all non-ionic detergents proved ineffective. The purified hOR17-4 protein was structurally and functionally characterized using several spectroscopy methods.

Results

Construction of Stable hOR17-4-Inducible HEK293S GnTI⁻ Cell Lines.

Figure 24A:
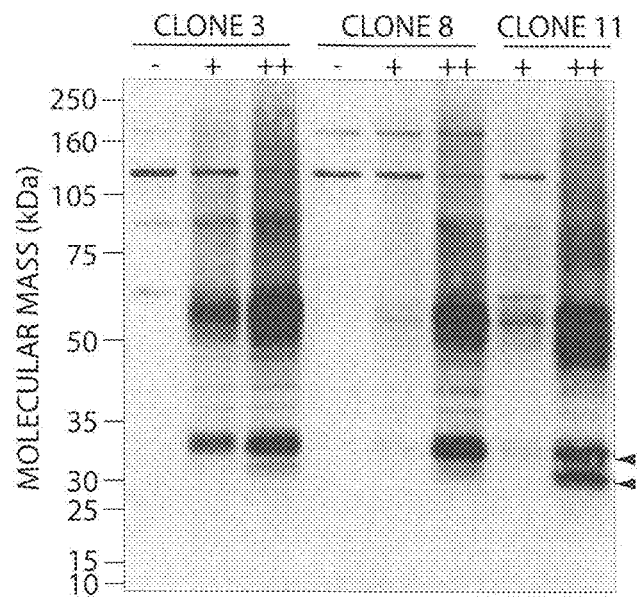
Figure 24B:
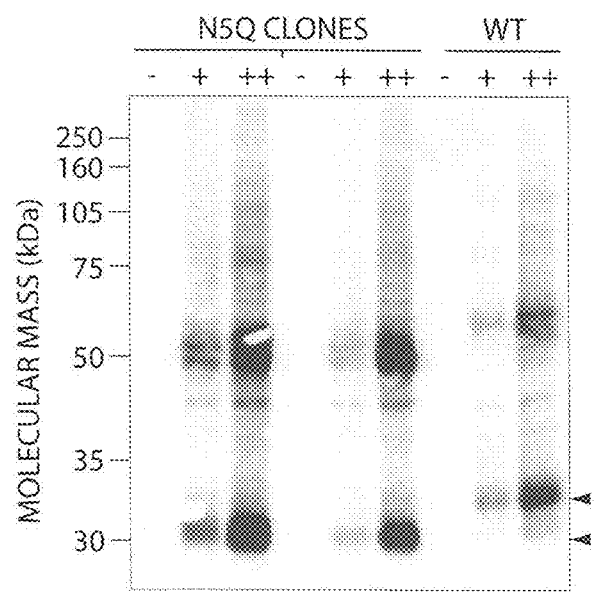

We recently described the fabrication of a synthetic hOR17-4 gene using PCR-based gene synthesis and the subsequent construction of stable HEK293S cell lines with tetracycline-inducible expression of the hOR17-4 receptor protein (5). When induced with a combination of tetracycline and sodium butyrate, these HEK293S cells generate over 30 µg of hOR17-4 per 15-cm plate. However, when assayed by SDS-PAGE, the receptor monomer migrated as a doublet at approximately 30 kD and 32 kD (the full-length rho-tagged hOR17-4 protein, with theoretical molecular mass of 36.2 kD, migrates slightly faster on SDS-PAGE gels). Our initial hypothesis was that the 32 kD band constituted a glycosylated form of the receptor. As heterogeneity could potentially interfere with future structural analysis and crystallization, we sought to achieve a homogeneous glycosylation pattern by porting the hOR17-4-inducible expression system into a HEK293S N-acetylglucosaminyltransferase I-negative (GnTI⁻) cell line shown to produce homogeneously glycosylated rhodopsin (8). During colony screening we isolated subclonal strains that exclusively expressed the slower migrating (32 kD) form of the receptor even under high-level expression (FIG. 24A).

Olfactory receptors possess a conserved N-linked glycosylation consensus sequence (Asn-X-Ser/Thr) at their N-termini (9), and the resulting glycosylation may be important for receptor functionality and proper folding (10), as is the case for other GPCRs (11). To investigate whether the observed size discrepancy was due to N-linked glycosylation, we generated a stable cell line that expressed a mutated form of hOR17-4 (N5Q) where the consensus asparagine was replaced by a glutamine. This hOR17-4 N5Q mutant ran solely at 30 kD with no 32 kD form present (FIG. 24B), indicating that the 32 kD form of wild-type hOR17-4 is N-glycosylated on Asn5. As lack of glycosylation could potentially compromise receptor function, all subsequent experiments were performed using the wild-type hOR17-4 inducible cell line (Clone 3, FIG. 24A).

Detergent Screening and Optimization of hOR17-4 Solubilization from HEK293S Cells.

Initial transient transfection into HEK293S cells and subsequent solubilization using the detergent dodecyl maltoside (DDM), which has been successfully used to solubilize several other GPCRs (6-8, 12), revealed low levels of hOR17-4 protein yield in comparison to constructs encoding opsin. To investigate whether DDM was insufficient to solubilize hOR17-4, we performed a large detergent screen that included representatives from the non-ionic, zwitter-ionic, polar, and ionic detergent classes. Immunoblot analysis showed that the majority of commercially available detergents were poor choices for extracting the hOR17-4 GPCR protein from HEK293S cells (FIG. 25). However, the fos-choline class of detergents proved highly effective and showed a clear relationship between chain length and solubilization yield, with fos-choline-16 (FC16) showing a >10-fold increase over DDM. However, the critical micelle concentration (CMC) of FC16 is so low (0.00053%) as to make any subsequent detergent exchange nearly impossible. Therefore, fos-choline-14 (FC14), with a CMC nearly 10× higher (0.0046%) was selected as optimal solubilization agent. Importantly, FC14 showed greater hOR17-4 yield than solubilization with harsher ionic detergents such as sarcosine and deoxycholate. The fos-choline detergents are structurally related to phosphatidylcholine (PC), a phospholipid and major constituent of the lipid bilayer of mammalian cells. Additional solubilization yield studies were carried out to determine the optimal FC14 concentration and extraction buffer. Addition of glycerol or increasing salt concentration was found to substantially decrease receptor yield.

After solubilization of hOR17-4 from native cell membranes, we attempted to exchange the zwitter-ionic fos-choline for the milder non-ionic dodecyl maltoside (DDM) during the immunoaffinity bead immobilization, as DDM has been successfully used to keep many other GPCRs soluble. However, this process resulted in a near total loss of hOR17-4 yield due to aggregation, indicating that FC14 is crucial not only for OR extraction but to maintain the solubility of OR proteins in solution. All subsequent purifications used FC14 exclusively.

Milligram-Scale Bioreactor Production of hOR17-4 and Subsequent Purification.

The use of adherent cell culture for milligram-scale purification of the receptor monomer poses a substantial challenge, as many hundreds of plates would be required. As the HEK293S GnTI⁻ cell line is capable of suspension culture at high cell densities, we chose to scale-up production using a bioreactor and methods previously optimized for the milligram-scale production of bovine rhodopsin$^{12}$. Each bioreactor run consisted of 1.25 liters of culture media inoculated with hOR17-4-inducible HEK293S GnTI⁻ cells at an initial density of 6-8×10⁵ cells/ml. The media was supplemented on day 5 and hOR17-4 expression induced on day 6 using tetracycline and sodium butyrate and harvested 40 hours later (day 8). Cell density at time of induction was 6.0×10⁶ cells/ml and had increased to 9.6×10⁶ cells/ml at the time of harvest. Thus a single 1.25 liter bioreactor run produced 12 billion cells (a cell pellet of 16 grams), the equivalent of ~200 15-cm tissue culture plates.

Figure 26B:
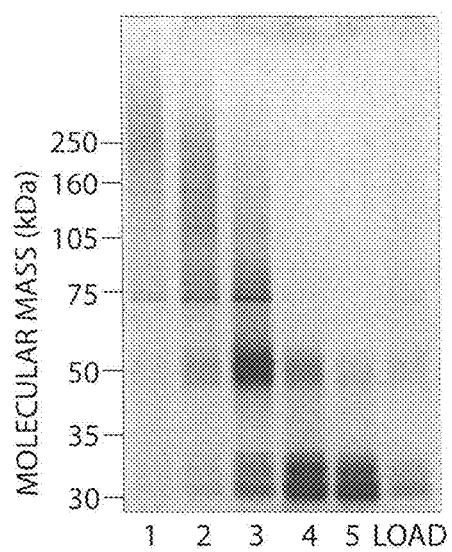

Cell pellets from two separate bioreactor runs were combined and subjected to solubilization using FC14 (molecular weight=379.5) followed by immunoaffinity purification using the rho1D4 monoclonal antibody (mAb) conjugated to sepharose beads in order capture the rho-tagged hOR17-4 protein. The eluate (containing 10.3 mg of hOR17-4) was then subjected to size exclusion chromatography to isolate the monomeric receptor fraction using gel filtration. Several peaks were observed (FIG. 26A) and were found to correspond to aggregate, dimeric, and monomeric receptor (FIG. 26B). The dimeric and monomer peaks eluted at 63.4 ml (0.51 column volumes (CV)) and 72.1 ml (0.58 CV), respectively, which was identical to that observed in our hOR17-4 purification using adherent culture (5). Using gel filtration standards we estimated the apparent masses of the hOR17-4-detergent complexes at 140 kD (monomer) and 275 kD (dimer), indicating that each hOR17-4 protein unit is solubilized in a complex with approximately 270 molecules of FC14 (2.8 g of FC14/g of protein). While this might seem high, the mass of detergent bound to most membrane proteins is far greater than the detergent micellar mass (i.e., ~47 kD for FC14) (13). For example, monomeric rhodopsin/DDM complexes are ~126 kD (14). Were our 140 kD complex to contain dimeric hOR17-4, each would be complexed with approximately 90 molecules of FC14 which is well below the aggregation number of 120 (14). Thus, we believe that the two peaks at 0.51 CV and 0.58 CV represent dimeric and monomeric receptor-detergent complexes, respectively.

Peak fractions were collected, pooled and concentrated and subjected to SDS-PAGE (FIG. 26B). The final yield of hOR17-4 monomer was 2.68 mg at >90% purity, the only other band visible being dimeric hOR17-4. Additionally, the putative dimer peak contained a total of 2.45 mg of largely dimeric receptor. Importantly, the appearance of monomer form in earlier peaks is likely due to the effects of SDS dissociating the dimeric and oligomeric receptor forms during gel electrophoresis.

Following the initial milligram scale purification, we repeated the experiment using two additional bioreactor runs (2.5 liters of suspension culture). However, a large excess of rho1D4-sepharose beads (60 ml bead slurry, total binding capacity 42 mg) was added to ensure complete capture of solubilized hOR17-4. Total yield of receptor following immunoaffinity chromatography was 30.5 mg, which led to the purification of 7.5 mg of hOR17-4 monomer following gel filtration chromatography. This constitutes nearly a three-fold increase over the first run and a yield of ~3 mg/liter for purified hOR17-4 monomer, which approaches yields of rhodopsin and rhodopsin mutants when similarly expressed (7). The resulting OR protein is at sufficiently high purity (>90%) for immediate concentration and application to crystallization screening.

Spectroscopic Characterization of Purified hOR17-4.

Figure 27A:
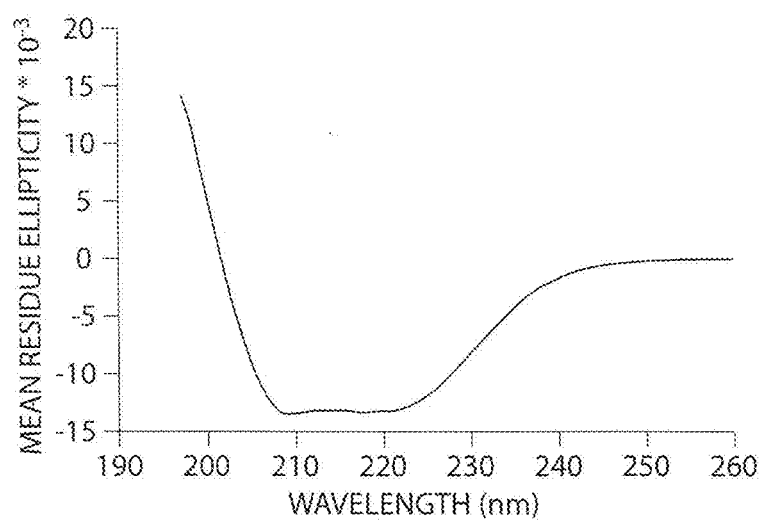

We asked if the purified, FC14-solubilized hOR17-4 retained proper structure and functionality. Our prediction for hOR17-4 secondary structure, based on structural modeling (15) and transmembrane domain calculations (http://www.uniprot.org/uniprot/P34982), was ~50% α-helix. When subjected to far-UV circular dichroism spectroscopy, the monomeric hOR17-4 displayed a spectrum characteristic of a predominantly alpha helical protein with minima at 208 nm and 222 nm (FIG. 27A). Analysis of the spectrum using the K2D algorithm (16) returned values of 49% α-helix, 18% β-sheet, and 33% random coil content, in agreement with predicted hOR17-4 secondary structure.

Figure 27B:
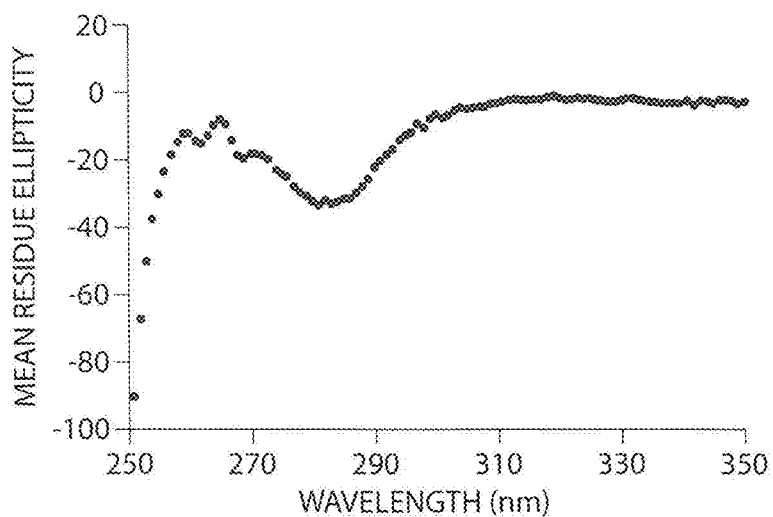

The ability to purify milligram quantities of purified hOR17-4 also allowed us to probe tertiary structure using near-UV CD spectroscopy (FIG. 27B). Several significant peaks were observed which suggest a defined tertiary structure. Wild-type opsin has similar near-UV peaks in this region, whereas functionally inactive opsin mutants showed flat spectra, indicating misfolded protein (17). Characterization by tryptophan fluorescence spectroscopy using excitation at 280 nm showed an emission maximum at 335 nm, which is similar to the value experimentally determined for rat OR5 of 328 nm (18).

hOR17-4 Activation Monitored by Intracellular Calcium-Ion Mobility Assay.

Since the C-terminal rho-tag could potentially interfere with G protein-mediated signal transduction, we also confirmed that our synthetic hOR17-4 displayed wild-type function in the HEK293S cell membranes. The functional activity and specificity of hOR17-4 was probed in heterologous HEK293S cells by monitoring intracellular calcium-ion concentrations using time-lapse confocal microscopy (19). In our HEK293S cells, olfactory receptors can signal through the inositol triphosphate ($IP_3$) pathway to release intracellular $Ca^{2+}$ from the ER, mediated by the "promiscuous" G-protein $G_{\alpha q}$. Induced cells responded to the specific odorant bourgeonal at concentrations as low as 1 μM (FIG. 28). Odorant response could be blocked by co-application of the hOR17-4 antagonist undecanal. No response was seen for the non-specific odorants octanal and anithole. Importantly, nearly 100% of the cells were responsive to bourgeonal due to the stable-inducible nature of this system, a vast improvement over expression methods that relied on transient transfection with less than 5% of cells being responsive (3).

Analysis of hOR17-4 Odorant Binding using SPR.

To assay the binding activity of detergent-solubilized hOR17-4, we developed an assay using surface plasmon resonance (SPR) to demonstrate that the solubilized receptor retains selectivity in binding odorant ligands in a concentration-dependent manner. First, the rho1D4 mAb was covalently attached to the dextran surface of a Biacore CM4 chip using standard amine-coupling chemistry. The hOR17-4 receptor protein was then non-covalently captured on the antibody via its C-terminal rho tag (TETSQVAPA (SEQ ID NO: 50)). Odorant ligands were then applied and odorant binding detected in real time via the mass-based refractive index change. Solubilized hOR17-4 receptors bound the specific odorants lilial and floralozone in a dose-dependent manner (FIG. 29). Due to low odorant solubility above 40 μM, the equilibrium dissociation constant could not be rigorously determined, but was approximately in the low micromolar range. Low affinity Biacore data is typically characterized by fast on- and off-rates, where curvature in the association and dissociation phase may not be observable. The different extents of curvature suggest different kinetic behavior for the two compounds, but further experiments would be required to fully characterize these differences. However, the sensorgram data shown reinforces the prediction of low, micromolar affinities for the two odorants. Additionally, no binding activity was detected for the non-specific odorant sulfuryl acetate (FIG. 29 inset). Thus, these results indicate that hOR17-4 receptor retains its specific binding activity in the solubilized state.

Characterization of hOR17-4 Post-Translational Modifications.

We next used mass spectrometry (chymotrypsin digest followed by LC-MS) to identify any post-translational modifications. Olfactory receptors are believed to possess two disulfide bonds between four conserved cysteine residues located in extracellular loops 1 and 2 (EC1 and EC2) (9). For hOR17-4, these two bonds are Cys97-Cys179 (EC1-EC2) and Cys169-Cys189 (EC2-EC2). Analysis confirmed the presence of the intra-EC2 disulfide bond (Cys169-Cys189) predicted for olfactory receptors (Table S1). No corresponding unlinked peptides were detected, indicating homogeneity. Presence of the remaining disulfide bond (Cys97-Cys179) was unconfirmed, as no corresponding peptides (disulfide-linked or unlinked) were detected, presumably due to the resistance of the detergent-solubilized OR to complete protease digestion.

Additionally, mass spectrometry determined the N-linked glycosylation present on Asn-5 to be $Man_3GlcNac_3$. This hexasaccharide is also the predominant glycosylation seen in retina-derived bovine opsin on Asn-2 and Asn-15 (20). However, it is worthwhile to note that rhodopsin heterologously prepared using the HEK293S GnTI⁻ cell line was found to have the N-glycan $Man_5GlcNac_2$ (8) indicating hOR17-4 follows a different glycosylation pathway in this system.

Discussion

Aspects of Glycosylation.

The appearance of two-distinct hOR17-4 monomer bands following purification could pose a problem for structural studies using X-ray diffraction, since typically a high degree of protein homogeneity is required for protein crystallization. We initially believed that it was possible to obtain primarily 32 kD form using the new HEK293S GnTI⁻ cell line clones (FIG. 24A). However, the rho1D4 immunoaffinity purification appears to significantly increase the proportion of 30 kD monomer form relative to 32 kD form, as seen in FIG. 26B. One hypothesis is that the 30 kD (potentially non-glycosylated form) binds more readily to the rho1D4-coupled bead matrix. Therefore, to obtain truly homogeneous hOR17-4 monomer it may be necessary to perform purifications using the hOR17-4 (N5Q) mutant cell line (FIG. 24), where only the 30 kD monomer form is produced. However, the functional effect of abolishing glycosylation on this receptor is unknown. Several studies have indicated that loss of GPCR glycosylation can lead to improper folding and targeting, resulting in decreased function and compromised structure and stability (11). Loss of either N-terminal glycosylation site (Asn-2 or Asn-15) of rhodopsin is sufficient to cause loss of signal transduction despite no apparent change in localization or folding (21, 22). Additionally, mutating out the glycosylation site of a mouse OR (mOR-EG) was found to completely abolished its ability to localize to the membrane (10), indicating that this modification may be necessary for OR function. As other heterologous expression systems (bacterial, insect, etc) lack mammalian post-translational machinery, purification of olfactory receptors from mammalian systems might be crucial for functional production.

In addition to the N-glycosylation site at Asn5, hOR17-4 has a potential site at Asn195. However, this residue does not appear to be glycosylated in this system as evidenced by: i) the N5Q mutation causes a complete shift in mobility from 32 kD (glycosylated) to the 30 kD form, which corresponds to the mass of the deglycosylated hOR17-4 protein (28); ii) mass spectrometry analysis did not detect glycosylation at this site but did detect unglycosylated peptides containing Asn195; iii) the consensus sequence is at the hypothetical EC2/TM5 border and thus is not likely to have the flexibility required for N-linked glycosylation. We did see a minor band running at ~33 kD for both the wild-type and N5Q mutant versions of hOR17-4 (FIGS. 24B and 26B), which we have not yet ruled out as due to potential Asn195 glycosylation. Since this band does not appear to shift with N5Q mutation, were this band glycosylated it would be on Asn195 alone (and not both sites). Should this be the case, a double mutant (N5Q, N195Q) might be advantageous, as it would eliminate both forms.

Detergent Screening.

Following a full-spectrum screening of over 45 different detergents, we demonstrated the utility of the fos-choline-based detergents (most notably FC14) in extracting and solubilizing olfactory receptors. Fos-choline-12 was recently found to refold the integral membrane protein diacylglycerol kinase and maintain its functional state (23). Additionally, the $E.\ coli$ mechanosensitive ion channel MscS was successfully crystallized using Fos-choline-14 and a high-resolution structure obtained (24). We also previously reported using a wheat germ cell-free system to produce hOR17-4, mOR23 and mS51 and using FC14 to stabilize them for purifications and activity binding assays (25). The promise of this detergent class in future membrane protein research is underscored by our recent findings which identified the fos-choline series as the best detergent class for extracting and solubilizing the GPCR human chemokine receptors CCR3, CCR5, CXCR4 and CX3CR1 (26).

Future Perspectives.

There have been a host of previous studies that have expressed and studied olfactory receptors in native and heterologous systems. While purification of ORs has been attempted in bacterial (18) and Sf9 insect (27, 28) systems, these were unable to produce large quantities of native full-length olfactory receptor. Our methods and results presented here constitute a cell-based platform for the production of milligram quantities of purified olfactory receptor. Currently, we have demonstrated the production of >10 milligrams of full-length human olfactory receptor hOR17-4 in a stable tetracycline-inducible HEK293S cell line. The application of this method to other olfactory receptors may lead to a generalized procedure for obtaining large quantities of any olfactory receptor in a rapid and simple manner. Such methods could prove extremely useful in discerning the elusive structure and functional mechanism of olfactory receptors, which would provide key insights into understanding the sense of smell at the molecular level. Additionally, the large-scale production of olfactory receptors is the prerequisite for their integration into OR-based biosensor devices.

TABLE S1

Analysis of purified hOR17-4 by mass spectrometry. List of chymotryptic hOR17-4 peptides identified by LC-MS. Amino acids in parentheses are those before and after the assigned peptide in the protein sequence. "Ox" indicates oxidation (e.g. of Met).

| Position | Assigned peptide sequence | Measured mass | Calc. (M + H) + m/z |
|---|---|---|---|
| 290-323 | (Y)SLRNKD . . . SQVAPA( )-ox (SEQ ID NO: 54) | 3720.1 | 3720.97 |
| 290-323 | (Y)SLRNKD . . . SQVAPA( ) (SEQ ID NO: 54) | 3704.1 | 3704.98 |
| 114-136 | (L)ILAVMA . . . HYTTAM(S) (SEQ ID NO: 55) | 2617.3 | 2618.26 |
| 61-82 | (Y)FFLANL . . . TIPKML(V) (SEQ ID NO: 56) | 2578.3 | 2579.36 |
| 267-289 | (Y)SVKDSV . . . MNPFIY(S) (SEQ ID NO: 57) | 2562.3 | 2563.26 |
| 73-94 | (F)FVTNTI . . . NKAISY(A) (SEQ ID NO: 58) | 2517.4 | 2518.41 |
| 123-143 | (R)YVAICC . . . PKLCIL(L) (SEQ ID NO: 59) | 2339.1 | 2340.16 |

TABLE S1-continued

Analysis of purified hOR17-4 by mass spectrometry. List of chymotryptic hOR17-4 peptides identified by LC-MS. Amino acids in parentheses are those before and after the assigned peptide in the protein sequence. "Ox" indicates oxidation (e.g. of Met).

| Position | Assigned peptide sequence | Measured mass | Calc. (M + H) + m/z |
|---|---|---|---|
| 99-118 | (L)TQLYFL . . . LILAVM(A) (SEQ ID NO: 60) | 2235.2 | 2236.27 |
| 267-283 | (Y)SVKDSV . . . AVVTPM(M) (SEQ ID NO: 61) | 1796.9 | 1797.91 |
| 277-288 | (Y)AVVTPMMNPFIY(S)-ox (SEQ ID NO: 62) | 1397.7 | 1398.68 |
| 83-94 | (L)VNLQSHNKAISY(A)-ox (SEQ ID NO: 63) | 1388.7 | 1389.71 |
| 277-288 | (Y)AVVTPMMNPFIY(S) (SEQ ID NO: 62) | 1381.7 | 1382.68 |
| 83-94 | (L)VNLQSHNKAISY(A) (SEQ ID NO: 63) | 1372.8 | 1373.72 |
| 28-36 | (L)FWMFLSMYL(V)-ox (SEQ ID NO: 64) | 1252.6 | 1253.57 |
| 28-36 | (L)FWMFLSMYL(V) (SEQ ID NO: 64) | 1236.6 | 1237.58 |
| 267-277 | (Y)SVKDSVATVMY(A)-ox (SEQ ID NO: 65) | 1214.6 | 1215.59 |
| 267-277 | (Y)SVKDSVATVMY(A) (SEQ ID NO: 65) | 1198.6 | 1199.60 |
| 73-82 | (F)FVTNTIPKML(V)-ox (SEQ ID NO: 66) | 1178.7 | 1179.64 |
| 73-82 | (F)FVTNTIPKML(V) (SEQ ID NO: 66) | 1162.7 | 1163.65 |
| 277-286 | (Y)AVVTPMMNPF(I) (SEQ ID NO: 67) | 1105.6 | 1106.54 |
| 267-276 | (Y)SVKDSVATVM(Y) (SEQ ID NO: 68) | 1035.6 | 1036.53 |
| 1-14 | ( )MDGGN*QSEGSEFLL(L) (SEQ ID NO: 69) | 2578.3 *Asn-5 modified with $Man_3$-$GlcNAc_3$ | 2578.33 |
| 169-178 | (F)C*GSRKIHYIF(C) (SEQ ID NO: 70) | 2819.1 | 2819.44 |
| 186-199 | (L)RMAC*SNIQINHTVL(I) (SEQ ID NO: 71) | *Peptides linked via disulfide bond | |

Buffers and Solutions.

Buffers used were as follows: Phosphate-buffered saline (PBS): 137 mM NaCl, 2.7 mM KCl, 1.8 mM $KH_2PO_4$, 10 mM $Na_2HPO_4$ (pH 7.4); Rinse buffer: PBS containing Complete Protease Inhibitor Cocktail (Roche); Solubilization buffer: Rinse buffer containing 2% wt/vol FC14; Wash buffer: PBS containing 0.2% FC14; Elution buffer: Wash buffer containing 100 μM Ac-TETSQVAPA-$CONH_2$ (SEQ ID NO: 50) elution peptide. All detergents, including FC14, were purchased from Anatrace (Maumee, Ohio) except digitonin, which was purchased from Sigma. All tissue culture and media components were purchased from Invitrogen unless otherwise noted. Sodium butyrate was purchased from Sigma.

Systematic Detergent Screening.

For initial solubilization trials, the wild-type pcDNA4/To-hOR17-4-rho plasmid was transiently transfected into 15-cm tissue culture plates of HEK293S cells using Lipofectamine 2000. After 48 hours, cells were scrape harvested and pooled. Cells were spun down and re-suspended in ice-cold rinse buffer at a density of $2 \times 10^7$ cells/ml and then aliquotted into microcentrifuge tubes. Detergent was then added from stock solutions (10% wt/vol) such that the final concentration was 2%, except where noted. Care was taken not to vortex or pipette-mix the samples after detergent was added in order to avoid breaking cell nuclei. Samples were then rotated at 4° C. for 4 hours before being centrifuged at 13,000×g for 30 minutes to pellet insoluble material. Supernatants were then removed and subjected to dot blot and SDS-PAGE analysis using the rho1D4 mAb. As dot blotting also detects aggregated/oligomerized receptor, the solubilization was quantified via SDS-PAGE western blotting as the total amount of monomeric and dimeric hOR17-4 present, as determined by spot densitometry. Relative solubilization corresponds to the fold increase over dodecyl maltoside (DDM).

Immunoblotting and Total Protein Staining.

Samples were assayed via polyacrylamide gel electrophoresis (SDS-PAGE) under both reducing and denaturing conditions as described previously (5).

Immunoaffinity Purification.

For immunoaffinity purification we utilized rho1D4 monoclonal antibody (Cell Essentials, Cambridge, Mass.) chemically linked to CNBr-activated Sepharose 4B beads (GE Healthcare). The rho1D4 elution peptide Ac-TETSQVAPA-CONH$_2$ (SEQ ID NO: 50) was synthesized by CBC Scientific. Rho1D4-sepharose immunoaffinity purification has been described previously (5, 7, 25, 26).

Size Exclusion Chromatography.

For further purification, hOR17-4 proteins were subjected to gel filtration chromatography using a HiLoad 16/60 Superdex 200 column (GE Healthcare) on a Äkta Purifier FPLC system (GE Healthcare), as described previously (5). Pooled hOR17-4 elution fractions from the rho1D4 immunoaffinity purification were concentrated to 3 mg/ml using a 10 kD MWCO filter column (Millipore) and then applied to the Äkta system. After loading, the column was run with wash buffer at 0.3 ml/min and column flow-through monitored via UV absorbance at 280 nm, 254 nm and 215 nm. The molecular mass of hOR17-4-detergent complexes was estimated by calibrating the column with gel-filtration standard mixture (Bio-Rad). Molecular mass was correlated to retention volume using a power law curve-fit.

Circular Dichroism Spectroscopy.

Spectra were recorded at 15° C. using a CD spectrometer (Aviv Associates, Model 202). Far-UV CD spectra were measured over the wavelength range of 195-260 nm with a step size of 1 nm and an averaging time of 5 s. Near-UV CD spectra were measured over the wavelength range of 250-350 nm with a step size of 1 nm and an averaging time of 10 seconds. All spectra were the average of 5 replicate scans. Spectra shown for purified hOR17-4 were blanked to wash buffer (concentrated to same extent as hOR17-4 sample) to remove effects of the detergent FC14. All measurements are reported in mean residue ellipticity (degrees×cm$^2$×dmole$^{-1}$). Protein concentration was determined from the aromatic absorption in 6 M Guanidinium HCl, pH 6.5 (29). All spectra were collected using a QS quartz sample cell (Hellma) with a path length of 1 mm. The secondary structural content was estimated using the program K2D (http://www.embl-heidelberg.de/%7Eandrade/k2d.html).

Calcium Signaling.

hOR17-4 expression in the stable HEK293S cell line was induced by 48-hour incubation in DMEM/F12 medium with GlutaMAX, supplemented with 1 μg/ml tetracycline. Then cells were loaded at 37° C. for 30 min with 10 mM Fura-Red-AM (Molecular Probes) in serum-free DMEM/F12 medium and were subsequently washed with PBS and incubated in DMEM/F12 medium containing 10% FCS for 30 min to allow complete hydrolysis of intracellular Fura-Red-AM. Cytosolic Ca$^{2+}$ responses were recorded by confocal fluorescence microscopy (Zeiss LSM 510) using a water immersion objective (Zeiss Achroplan 63×, NA 1.2). Excitation was at 488 nm (Ar$^+$ laser); the 650 nm long pass emission filter was used to image Fura-Red at a rate of 1 image per second. Stock solutions of the tested odorants were prepared freshly in DMSO and diluted 1000-fold into PBS to give the desired concentrations.

Surface Plasmon Resonance (Biacore™ A100) Odorant Binding Assay.

All odorant binding experiments were performed at 25° C. on a Biacore™ A100 (GE Healthcare), which has a parallel flow configuration, allowing assay development (e.g., solubilization conditions) to be tested and optimized in parallel and multiplexed format. The sensor chip CM4, amine-coupling kit, HBS (10 mM Hepes, 0.15 M NaCl, pH 7.4) and PBS were from GE Healthcare. The detailed protocol (see Supporting Information) was adapted, with several key modifications, from that previously reported by Kaiser et al. (25).

Site Directed Mutagenesis.

The pcDNA4/To-hOR17-4-rho plasmid, containing a synthetic, codon optimized hOR17-4-rho gene construct (30), was mutated to eliminate the hOR17-4 N-linked glycosylation consensus sequence. The codon corresponding to hOR17-4 residue Asn5 was converted from AAC (Asn) to CAG (Gln) by site directed mutagenesis using the Quikchange kit (Stratagene) according to the manufacturer's instructions. The oligonucleotides used were: 5'-CCATG-GACGGAGGCCAGCAAAGCGAGGGCAG-3' (top) (SEQ ID NO: 48) and 5'-CTGCCCTCGCTTTGCTGGCCTC-CGTCCATGG-3' (bottom) (SEQ ID NO: 49). The successfully mutated plasmid was designated pcDNA4/To-hOR17-4(N5Q)-rho.

Generation of Stable hOR17-4-Inducible Cell Lines.

HEK293S GnTI$^-$ (suspension adapted, N-acetylglucosaminyltransferase I-negative HEK293) cells containing the stable expression of pcDNA6/Tr (Invitrogen), which encodes the Tet repressor protein (TetR) had previously been generated and cloned (31). Adherent HEK293S GnTI$^-$ cell monolayers were cultured as described previously for HEK293S cells (1). Either the pcDNA4/To-hOR17-4-rho plasmid, containing a synthetic, codon optimized, rho-tagged hOR17-4 gene construct (hOR17-4-GG-TETSQVAPA (SEQ ID NO: 50)) (30) or the pcDNA4/To-hOR17-4(N5Q)-rho plasmid were then transfected into these cells using Lipofectamine 2000 and after 48 hours cells were subjected to drug selection in 5 μg/ml blasticidin and 50 μg/ml zeocin for 2 weeks and then subcloned. For each variant, at least 25 colonies were expanded and screened for inducible expression in 6-well plates after a 48 hour treatment of plain media (control) or media supplemented with 1 ug/ml tetracycline or tetracycline plus 5 mM sodium butyrate. Cell extracts were then prepared as described previously (30) and then analyzed via dot blotting and SDS-PAGE western blotting using the mouse mAb rho1D4. For wild-type hOR17-4, Clone 3 was selected and expanded into large-scale culture and used for all subsequent experiments. The hOR17-4-inducible HEK293S GnTI$^-$ cell lines were maintained using 5 μg/ml blasticidin and 25 μg/mlzeocin.

Bioreactor Culture.

Suspension culture of HEK293S GnTI– cells was carried out in a Celligen Plus bioreactor (New Brunswick Scientific) according to the protocol developed by Reeves et at (32). Media formulation was identical except that Primatone RL-UF was used at 3.0 g/liter. On day 0, the bioreactor media was inoculated with cells trypsinized from 6-9 confluent 15-cm tissue culture plates such that the inoculation density was 6×10$^5$ cells/ml. The four-gas mixture (air, O$_2$, N$_2$, and CO$_2$) was supplied by direct sparge only. Gas flow rate was initially 21 ml/min but was increased as needed throughout the run to regulate the pH and dissolved oxygen. If required, 20 ml of 8% sodium bicarbonate was added to increase the buffering capacity of the media if the gas mixture was unable to adequately regulate the pH. On day 5, the reactor was supplemented with 30 ml of 10% Primatone RL-UF and 10 ml of 20% glucose. On day 6, the expression of hOR17-4 was induced by the addition of tetracycline (2 µg/ml) and sodium butyrate (2 mM) and the cells harvested 40 hours post-induction. Harvested cells were pelleted and washed with cold rinse buffer. The cell pellets were then weighed and snap-frozen in liquid nitrogen and stored at −80° C. until purification was carried out. On the day of purification, cells were thawed on wet ice and spun down by centrifugation at 4,000 g for 1 minute. All further steps were performed at 4° C. unless noted. The hOR17-4 was then solubilized by resuspending the cells in solubilization buffer (12.5 ml per gram of cell pellet) and rotating for 4 hours. The non-solubilized fraction was then pelleted using an ultracentrifuge at >100,000×g for 45 minutes. The resulting supernatant (total lysate) was removed and directly applied to immunoaffinity purification at 4° C.

Mass Spectrometry.

Liquid samples of purified monomeric hOR17-4 were subjected to chymotrypsin digestion and the resulting fragments analyzed using LC-MS by the MIT Koch Institute Proteomics Core Facility (Cambridge, Mass.). Proteolytic peptides were separated using 0.075 mm×15 cm C18 column on a nano-HPLC system (TEMPO from Applied Biosystems). Gradient elution with a water-acetonitrile-formic acid solvent system of peptides was carried out at a flow rate of 250 nl/min over 87 min. Electrospray mass spectra were acquired with a quadrupole time-of-flight mass spectrometer (QSTAR Elite from Applied Biosystems).

Surface Plasmon Resonance Odorant Binding Assay.

The rho1D4 monoclonal antibody (40 µg/ml in 10 mM sodium acetate, pH 5.5) was immobilized onto a series S sensor chip CM4 using standard amine-coupling chemistry in HBS running buffer at 10 µl/min according to Biacore handbook (33). The amount of coupled rho1D4 was 5,500 RU. Control surfaces were prepared similarly without protein derivatization and utilized as a reference surfaces for odorant binding experiments.

HEK293S hOR17-4-rho cells were induced with 1 µg/ml tetracycline plus 5 mM sodium butyrate for 48 hours and then scrape harvested 48 h post-induction. The cells (5×10⁶ cells/ml) were lysed with 1.5% FC-14 for 90 min at 4° C. The lysed cell suspension was centrifuged for 10 minutes at 14,000×g at 4° C. to remove cell debris. The supernatant, containing the solubilized olfactory receptor, was immediately captured on the surface plasmon resonance (SPR) chip using PBS, 1 mM Anzergent 3-14 (5×CMC), 5 mM TCEP, and 1.5% (v/v) ethanol as running buffer at 10 µl/min. A four-minute injection resulted in a surface density of 2,800 RU.

Fresh odorant solutions were made as follows. Pure odorant was diluted in ethanol to 0.5 M. This solution was diluted 67 times in PBS, 1 mM Anzergent 3-14, 5 mM TCEP, to obtain a 7.5 mM odorant solution in running buffer with 1.5% (v/v) ethanol. Further dilutions were made in running buffer containing 1.5% (v/v) ethanol to obtain a concentration series of 5, 10, 20 and 40 µM of the odorants.

For the actual odorant binding measurements, the odorant concentration series were injected from low to high concentration over control and derivatized surfaces for 30 seconds with a flow rate of 30 µl/min. Zero concentration blank buffer cycles were included as negative control samples. Solvent correction procedures were included to compensate for any ethanol related bulk refractive index variations and performed as described previously (34). Non-specific binding effects to sensor surface CM4 were absent for all analyses reported.

Data analysis was carried out using Biacore A100 evaluation software. Data were prepared by subtraction of reference surface data and blank buffer sample data, a procedure commonly referred to as double referencing (35). Solvent correction was then applied as described previously (36).

REFERENCES

1. Buck, L. & Axel, R. (1991) A novel multigene family may encode odorant receptors: a molecular basis for odor recognition. *Cell* 65: 175-187.
2. Malnic, B., Hirono, J., Sato, T. & Buck, L. B. (1999) Combinatorial receptor codes for odors. *Cell* 96: 713-723.
3. Spehr, M., Gisselmann, G., Poplawski, A., Riffell, J. A., Wetzel, C. H., et al. (2003) Identification of a testicular odorant receptor mediating human sperm chemotaxis. *Science* 299: 2054-2058.
4. Hanson M A and Stevens R C. (2009) Discovery of new GPCR biology: one receptor structure at a time. *Structure* 17(1): 8-14.
5. Cook, B. L., Ernberg, K. E., Chung, H. & Zhang S. (2008) Study of a Synthetic Human Olfactory Receptor 17-4: Expression and Purification from an Inducible Mammalian Cell Line. *PLoS ONE* 3(8): e2920.
6. Reeves, P. J., Thurmond, R. L. & Khorana, H. G. (1996) Structure and function in rhodopsin: high level expression of a synthetic bovine opsin gene and its mutants in stable mammalian cell lines. *Proc. Natl. Acad. Sci. USA* 93: 11487-11492.
7. Reeves, P. J., Kim, J. M. & Khorana, H. G. (2002) Structure and function in rhodopsin: a tetracycline-inducible system in stable mammalian cell lines for high-level expression of opsin mutants. *Proc. Natl. Acad. Sci. USA* 99: 13413-13418.
8. Reeves, P. J., Callewaert, N., Contreras, R. & Khorana, H. G. (2002) Structure and function in rhodopsin: high-level expression of rhodopsin with restricted and homogeneous N-glycosylation by a tetracycline-inducible N-acetylglucosaminyltransferase I-negative HEK293S stable mammalian cell line. *Proc. Natl. Acad. Sci. USA* 99: 13419-13424.
9. Liu, A. H., Zhang, X., Stolovitzky, G. A., Califano, A. & Firestein, S. J. (2003) Motif-based construction of a functional map for mammalian olfactory receptors. *Genomics* 81: 443-456.
10. Katada, S., Tanaka, M. & Touhara, K. (2004) Structural determinants for membrane trafficking and G protein selectivity of a mouse olfactory receptor. *J. Neurochem.* 90: 1453-1463.
11. Wheatley, M. & Hawtin, S. R. (1994) Glycosylation of G-protein-coupled receptors for hormones central to normal reproductive functioning: its occurrence and role. *Hum. Reprod. Update* 5: 356-364.
12. Chelikani, P., Reeves, P. J., Rajbhandary, U. L. & Khorana, H. G. The synthesis and high-level expression of a beta2-adrenergic receptor gene in a tetracycline-inducible stable mammalian cell line. *Protein Sci.* 15: 1433-1440 (2006).
13. Strop, P. & Brunger, A. T. Refractive index-based determination of detergent concentration and its application to the study of membrane proteins. *Protein Sci.* 14: 2207-2211 (2005).
14. Chabre, M. & le Maire, M. Monomeric (2005) G-protein-coupled receptor as a functional unit. *Biochemistry* 44: 9395-9403.

15. Pilpel, Y. & Lancet, D. (1999) The variable and conserved interfaces of modeled olfactory receptor proteins. *Protein Sci.* 8: 969-977.
16. Andrade, M. A., Chacon, P., Merelo, J. J. & Moran, F. (1993) Evaluation of secondary structure of proteins from UV circular dichroism using an unsupervised learning neural network. *Prot. Eng.* 6: 383-390.
17. Liu, X., Garriga, P. & Khorana, H. G. (1996) Structure and function in rhodopsin: correct folding and misfolding in two point mutants in the intradiscal domain of rhodopsin identified in retinitis pigmentosa. *Proc. Natl. Acad. Sci. USA* 93: 4554-4559.
18. Kiefer H. et al. (1996) Expression of an olfactory receptor in *Escherichia coli*: purification, reconstitution, and ligand binding. *Biochemistry* 35: 16077-16084.
19. Jacquier, V., Pick, H. & Vogel, H. (2006) Characterization of an extended receptive ligand repertoire of the human olfactory receptor OR17-40 comprising structurally related compounds. *J. Neurochem.* 97: 537-544.
20. Fukuda, M. N., Papermaster, D. S. & Hargrave, P. A. (1979) Rhodopsin carbohydrate. Structure of small oligosaccharides attached at two sites near the $NH_2$ terminus. *J. Biol. Chem.* 254: 8201-8207.
21. Kaushal, S., Ridge, K. D. & Khorana, H. G. (1994) Structure and function in rhodopsin: the role of asparagine-linked glycosylation. *Proc. Natl. Acad. Sci. USA* 91: 4024-4028.
22. Zhu L, Jong G F, Jastrzebska B, Filipek S, Pearce-Kelling S E, Aguirre G D, Stenkamp R E, Acland G M, Palczewski K (2004). A naturally occurring mutation of the opsin gene (T4R) in dogs affects glycosylation and stability of the G protein-coupled receptor. *J. Biol. Chem.* 279: 53828-53839.
23. Gorzelle B M, Nagy J K, Oxenoid K, Lonzer W L, Cafiso D S, Sanders C R. (2002) Reconstitutive refolding of diacylglycerol kinase, an integral membrane protein. *Biochemistry* 38: 16373-16382.
24. Bass, R. B., Strop, P., Barclay, M., Rees, D. C. (2002) Crystal structure of *Escherichia coli* MscS, a voltage-modulated and mechanosensitive channel. *Science* 298: 1582-1587.
25. Kaiser, L., Graveland-Bikker, J., Steuerwald, D., Vanberghem, M., Herlihy, K., Zhang, S. (2008) Efficient cell-free production of olfactory receptors: detergent optimization, structure and odorant binding analyses *Proc. Natl. Acad. Sci. USA* 105: 15726-15731.
26. Ren, H., Yu, D., Ge, B., Cook, B. L., Xu, Z., & Zhang, S (2009) High-level production, solubilization and purification of synthetic human GPCR chemokine receptors CCR5, CCR3, CXCR4 and CX3CR1. *PLoS ONE* 4(2): e4509.
27. Gat, U., Nekrasova, E., Lancet, D. & Natochin, M. (1994) Olfactory receptor proteins. Expression, characterization and partial purification. *Eur. J. Biochem.* 225: 1157-1168.
28. Nekrasova, E., Sosinskaya, A., Natochin, M., Lancet, D. & Gat, U. (1996) Overexpression, solubilization and purification of rat and human olfactory receptors. *Eur. J. Biochem.* 238: 28-37.
29. Greenfield, N. J. (2006) Using circular dichroism spectra to estimate protein secondary structure. *Nat. Protoc.* 1: 2876-2890.
30. Cook, B. L., Ernberg, K. E., Chung, H. & Zhang S. (2008) Study of a Synthetic Human Olfactory Receptor 17-4: Expression and Purification from an Inducible Mammalian Cell Line. *PLoS ONE* 3(8): e2920.
31. Reeves, P. J., Callewaert, N., Contreras, R. & Khorana, H. G. (2002) Structure and function in rhodopsin: high-level expression of rhodopsin with restricted and homogeneous N-glycosylation by a tetracycline-inducible N-acetylglucosaminyltransferase I-negative HEK293S stable mammalian cell line. *Proc. Natl. Acad. Sci. USA* 99: 13419-13424.
32. Reeves, P. J., Kim, J. M. & Khorana, H. G. (2002) Structure and function in rhodopsin: a tetracycline-inducible system in stable mammalian cell lines for high-level expression of opsin mutants. *Proc. Natl. Acad. Sci. USA* 99: 13413-13418.
33. Biacore sensor surface handbook (2003) (Biacore Uppsala, Sweden).
34. Karlsson R, Kullman-Magnusson M, Hamalainen M D, Remaeus A, Andersson K, Borg P, Gyzander E, Deinum J. (2000) Biosensor analysis of drug-target interactions: direct and competitive binding assays for investigation of interactions between thrombin and thrombin inhibitors. *Anal. Biochem.* 278: 1-13.
35. Myszka, D. G. (1999) Improving biosensor analysis. *J. Mol. Recognit.* 12: 279-284.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A bio-sensing nanodevice comprising: a plurality of stabilized olfactory receptors on a detector comprising a receptor binding surface, a test composition delivery system [5] and a test composition recognition program [7] wherein the detector comprises a dielectric/metal/dielectric sandwich structure, wherein a laser light source is irradiated across a metal layer of the dielectric/metal/dielectric sandwich structure on a horizontal plane causing Plasmon to be generated on both the top and bottom of the metal layer;

wherein the nanodevice comprises a plurality of optical waveguide sensors, wherein each optical waveguide sensor comprises a first optical waveguide and a second optical waveguide, wherein a shifted amount of light from the first optical waveguide to the second optical waveguide changes when the test composition comprises a substance to be detected, wherein each detector comprises a microsurface plasmon polariton and measures the amount of outgoing light from the second optical waveguide, wherein each detector is disposed between the first optical waveguide and the second optical waveguide and wherein a stabilized olfactory receptor is disposed on the surface of each detector such that a plurality of test compositions can be detected; and wherein the stabilized olfactory receptors are stabilized with a surfactant peptide.

2. The bio-sensing device of claim 1, wherein the laser light source is irradiated to the olfactory receptor via light fiber.

3. The bio-sensing nanodevice of claim 1, wherein the surfactant peptides have a formula selected from the group consisting of:

a. $(\Phi)_m(+)_n$ (Formula (1)), b. $(+)_n(\Phi)_m$ (Formula (2)), c. $(\Phi)_m(-)_n$ (Formula (3)), d. $(-)_n(\Phi)_m$ (Formula (4)), e. $(-)_n(\Phi)_m(-)_n$ (Formula (5)), f. $(+)_n(\Phi)_m(+)_n$ (Formula (6)), g. $(\Phi)_m(-)_n(\Phi)_m$ (Formula (7)), h. $(\Phi)_m(+)_n(\Phi)_m$ (Formula (8)), i. $(+)_n(\Phi)_m(-)_n$ (Formula (9)), j. $(-)_n(\Phi)_m(+)_n$ (Formula (10)), k. $(\tau)_m(\Phi)_m$ (Formula (11)), l. $(\Phi)_m(\tau)_n$ (Formula (12)), m. $(\tau)_n(\Phi)_m(\tau)_n$, (Formula (13)), and n. $(\Phi)_m(\tau)_n(\Phi)_m$, (Formula (14)), wherein:

($\Phi$) represents independently for each occurrence a natural or non-natural amino acid comprising a hydrophobic sidechain;

(+) represents independently for each occurrence a natural or non-natural amino acid comprising a sidechain that is cationic at physiological pH;

(−) represents independently for each occurrence a natural or non-natural amino acid comprising a sidechain that is anionic at physiological pH;

($\tau$) represents independently a polar amino acid containing a non-charged side chain at physiological pH, wherein the terminal amino acids are optionally substituted;

m for each occurrence represents an integer greater than or equal to 5; and n for each occurrence represents an integer greater than or equal to 1.

4. The bio-sensing nanodevice of claim 3, wherein the surfactant peptide is selected from the group consisting of:

| | |
|---|---|
| AAAAAAD, | (SEQ ID NO: 1) |
| VVVVVVD, | (SEQ ID NO: 2) |
| AAAAAADD, | (SEQ ID NO: 3) |
| VVVVVVDD, | (SEQ ID NO: 4) |
| LLLLLLDD, | (SEQ ID NO: 5) |
| KKIIIIII, | (SEQ ID NO: 6) |
| KKLLLLLL, | (SEQ ID NO: 7) |
| KKAAAAAA, | (SEQ ID NO: 8) |
| KKVVVVVV, | (SEQ ID NO: 9) |
| DDDDDDDDDDAAAAAAAAAA, | (SEQ ID NO: 10) |
| AAAAAAAAAADDDDDDDDDD, | (SEQ ID NO: 11) |
| EEEEEEEEEEAAAAAAAAAA, | (SEQ ID NO: 12) |
| AAAAAAAAAAEEEEEEEEEE, | (SEQ ID NO: 13) |
| DDDDDDDDDDVVVVVVVVVV, | (SEQ ID NO: 14) |
| VVVVVVVVVVDDDDDDDDDD, | (SEQ ID NO: 15) |
| DDDDDDDDDDPPPPPPPPPP, | (SEQ ID NO: 16) |
| PPPPPPPPPPDDDDDDDDDD, | (SEQ ID NO: 17) |
| AAAAAAAAAAHHHHHHHHHH, | (SEQ ID NO: 18) |
| HHHHHHHHHHAAAAAAAAAA, | (SEQ ID NO: 19) |
| KKKKKKKKKKAAAAAAAAAA, | (SEQ ID NO: 20) |
| AAAAAAAAAAKKKKKKKKKK, | (SEQ ID NO: 21) |
| RRRRRRRRRRAAAAAAAAAA, | (SEQ ID NO: 22) |

-continued

| | |
|---|---|
| AAAAAAAAAARRRRRRRRRR, | (SEQ ID NO: 23) |
| DDDDDDDDDDAAAAAAAAAADDDDDDDDDD, | (SEQ ID NO: 24) |
| EEEEEEEEEEAAAAAAAAAAEEEEEEEEEE, | (SEQ ID NO: 25) |
| DDDDDDDDDDVVVVVVVVVVDDDDDDDDDD, | (SEQ ID NO: 26) |
| DDDDDDDDDDPPPPPPPPPPDDDDDDDDDD, | (SEQ ID NO: 27) |
| HHHHHHHHHHAAAAAAAAAAHHHHHHHHHH, | (SEQ ID NO: 28) |
| KKKKKKKKKKAAAAAAAAAAKKKKKKKKKK, | (SEQ ID NO: 29) |
| RRRRRRRRRRAAAAAAAAAARRRRRRRRRR, | (SEQ ID NO: 30) |
| AAAAAAAAAADDDDDDDDDDAAAAAAAAAA, | (SEQ ID NO: 31) |
| AAAAAAAAAAEEEEEEEEEEAAAAAAAAAA, | (SEQ ID NO: 32) |
| VVVVVVVVVVDDDDDDDDDDVVVVVVVVVV, | (SEQ ID NO: 33) |
| PPPPPPPPPPDDDDDDDDDDPPPPPPPPPP, | (SEQ ID NO: 34) |
| AAAAAAAAAAHHHHHHHHHHAAAAAAAAAA, | (SEQ ID NO: 35) |
| AAAAAAAAAAKKKKKKKKKKAAAAAAAAAA, | (SEQ ID NO: 36) |
| AAAAAAAAAARRRRRRRRRRAAAAAAAAAA, | (SEQ ID NO: 37) |
| KKKKKKKKKKAAAAAAAAAADDDDDDDDDD, | (SEQ ID NO: 38) |
| KKKKKKKKKKAAAAAAAAAAEEEEEEEEEE, | (SEQ ID NO: 39) |
| RRRRRRRRRRVVVVVVVVVVDDDDDDDDDD, | (SEQ ID NO: 40) |
| KKKKKKKKKKPPPPPPPPPPDDDDDDDDDD, | (SEQ ID NO: 41) |
| HHHHHHHHHHAAAAAAAAAAEEEEEEEEEE, | (SEQ ID NO: 42) | and

| | |
|---|---|
| AAAAAAK | (SEQ ID NO: 47). |

5. The bio-sensing nanodevice of claim 3, wherein the surfactant peptide is AAAAAAD (SEQ ID NO: 1), VVVVVVD (SEQ ID NO: 2) or AAAAAAK (SEQ ID NO: 47).

6. The bio-sensing nanodevice of claim 1, wherein the test composition is an odorant.

7. The bio-sensing nanodevice of claim 6, wherein the olfactory receptor is a mammalian receptor.

8. The bio-sensing nanodevice of claim 6, wherein at least one olfactory receptor is hOR17-4.

9. The bio-sensing nanodevice of claim 1, wherein the detector [15] comprises a material selected from gold, silver, platinum, glass, silicon, silica, polystyrene and polymer films, which is coated or non-coated.

10. The bio-sensing nanodevice of claim 1, wherein the test composition delivery system [5] is passive exposure to air or microfluidic bubble logic operation.

11. The bio-sensing nanodevice of claim 10, wherein the microfluidic bubble logic operation comprises micron-sized droplets and bubbles of chemical in a microfluidic chip [11].

12. The bio-sensing nanodevice of claim 1, wherein the test composition recognition program [7] comprises a 1 dimensional peak-recognition program.

* * * * *

SEQUENCE LISTING

```
<160> NUMBER OF SEQ ID NOS: 71

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Ala Ala Ala Ala Ala Ala Asp
```

```
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Val Val Val Val Val Val Asp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Ala Ala Ala Ala Ala Ala Asp Asp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Val Val Val Val Val Val Asp Asp
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Leu Leu Leu Leu Leu Leu Asp Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Lys Lys Ile Ile Ile Ile Ile Ile
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Lys Lys Leu Leu Leu Leu Leu Leu
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Lys Lys Ala Ala Ala Ala Ala Ala Ala
 1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Lys Lys Val Val Val Val Val Val
 1               5

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Asp Asp Asp Asp Asp Asp Asp Asp Asp Asp Ala Ala Ala Ala Ala
 1               5                  10                  15

Ala Ala Ala Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Ala Ala Ala Ala Ala Ala Ala Ala Ala Ala Asp Asp Asp Asp Asp
 1               5                  10                  15

Asp Asp Asp Asp
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Glu Glu Glu Glu Glu Glu Glu Glu Glu Glu Ala Ala Ala Ala Ala
 1               5                  10                  15

Ala Ala Ala Ala
            20

<210> SEQ ID NO 13
<211> LENGTH: 20
<212> TYPE: PRT
<213> ORGANISM: Artificial Sequence
<220> FEATURE:
```

<223> OTHER INFORMATION: Synthetic

<400> SEQUENCE: 13

Ala Ala Ala Ala Ala Ala Ala Ala Glu Glu Glu Glu Glu Glu Glu
1               5                   10                  15

Glu Glu Glu Glu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Asp Asp Asp Asp Asp Asp Asp Asp Asp Val Val Val Val Val Val
1               5                   10                  15

Val Val Val Val
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic

<400> SEQUENCE: 15

Val Val Val Val Val Val Val Val Val Asp Asp Asp Asp Asp Asp
1               5                   10                  15

Asp Asp Asp Asp
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Asp Asp Asp Asp Asp Asp Asp Asp Asp Asp Pro Pro Pro Pro Pro
1               5                   10                  15

Pro Pro Pro Pro
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic

<400> SEQUENCE: 17

Pro Pro Pro Pro Pro Pro Pro Pro Pro Pro Asp Asp Asp Asp Asp
1               5                   10                  15

Asp Asp Asp Asp
            20

<210> SEQ ID NO 18
<211> LENGTH: 20
<212> TYPE: PRT
<213> ORGANISM: Artificial Sequence
<220> FEATURE:

<223> OTHER INFORMATION: Synthetic

<400> SEQUENCE: 18

Ala Ala Ala Ala Ala Ala Ala Ala Ala His His His His His
1               5                   10                  15

His His His His
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

His His His His His His His His His Ala Ala Ala Ala Ala
1               5                   10                  15

Ala Ala Ala Ala
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Lys Lys Lys Lys Lys Lys Lys Lys Lys Ala Ala Ala Ala Ala
1               5                   10                  15

Ala Ala Ala Ala
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Ala Ala Ala Ala Ala Ala Ala Ala Ala Lys Lys Lys Lys Lys
1               5                   10                  15

Lys Lys Lys Lys
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic

<400> SEQUENCE: 22

Arg Arg Arg Arg Arg Arg Arg Arg Arg Ala Ala Ala Ala Ala
1               5                   10                  15

Ala Ala Ala Ala
            20

<210> SEQ ID NO 23
<211> LENGTH: 20
<212> TYPE: PRT
<213> ORGANISM: Artificial Sequence
<220> FEATURE:

<223> OTHER INFORMATION: Synthetic

<400> SEQUENCE: 23

Ala Ala Ala Ala Ala Ala Ala Ala Arg Arg Arg Arg Arg
1               5                   10                  15

Arg Arg Arg Arg
        20

<210> SEQ ID NO 24
<211> LENGTH: 30
<212> TYPE: PRT
<213> ORGANISM: Artificial Sequence
<220> FEATURE:
<223> OTHER INFORMATION: Synthetic

<400> SEQUENCE: 24

Asp Asp Asp Asp Asp Asp Asp Asp Asp Ala Ala Ala Ala Ala
1               5                   10                  15

Ala Ala Ala Ala Asp Asp Asp Asp Asp Asp Asp Asp Asp
        20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic

<400> SEQUENCE: 25

Glu Glu Glu Glu Glu Glu Glu Glu Glu Ala Ala Ala Ala Ala
1               5                   10                  15

Ala Ala Ala Ala Glu Glu Glu Glu Glu Glu Glu Glu Glu
        20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic

<400> SEQUENCE: 26

Asp Asp Asp Asp Asp Asp Asp Asp Asp Val Val Val Val Val
1               5                   10                  15

Val Val Val Val Asp Asp Asp Asp Asp Asp Asp Asp Asp
        20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic

<400> SEQUENCE: 27

Asp Asp Asp Asp Asp Asp Asp Asp Asp Pro Pro Pro Pro Pro
1               5                   10                  15

Pro Pro Pro Pro Asp Asp Asp Asp Asp Asp Asp Asp Asp
        20                  25                  30

<210> SEQ ID NO 28
<211> LENGTH: 30
<212> TYPE: PRT
<213> ORGANISM: Artificial Sequence
<220> FEATURE:

-continued

<223> OTHER INFORMATION: Synthetic

<400> SEQUENCE: 28

```
His His His His His His His His Ala Ala Ala Ala Ala
1               5                   10                  15
Ala Ala Ala Ala His His His His His His His His
            20                  25                  30
```

<210> SEQ ID NO 29
<211> LENGTH: 30
<212> TYPE: PRT
<213> ORGANISM: Artificial Sequence
<220> FEATURE:
<223> OTHER INFORMATION: Synthetic

<400> SEQUENCE: 29

```
Lys Lys Lys Lys Lys Lys Lys Lys Lys Ala Ala Ala Ala Ala
1               5                   10                  15
Ala Ala Ala Ala Lys Lys Lys Lys Lys Lys Lys Lys Lys
            20                  25                  30
```

<210> SEQ ID NO 30
<211> LENGTH: 30
<212> TYPE: PRT
<213> ORGANISM: Artificial Sequence
<220> FEATURE:
<223> OTHER INFORMATION: Synthetic

<400> SEQUENCE: 30

```
Arg Arg Arg Arg Arg Arg Arg Arg Arg Arg Ala Ala Ala Ala Ala
1               5                   10                  15
Ala Ala Ala Ala Arg Arg Arg Arg Arg Arg Arg Arg Arg
            20                  25                  30
```

<210> SEQ ID NO 31
<211> LENGTH: 30
<212> TYPE: PRT
<213> ORGANISM: Artificial Sequence
<220> FEATURE:
<223> OTHER INFORMATION: Synthetic

<400> SEQUENCE: 31

```
Ala Ala Ala Ala Ala Ala Ala Ala Ala Asp Asp Asp Asp Asp Asp
1               5                   10                  15
Asp Asp Asp Asp Ala Ala Ala Ala Ala Ala Ala Ala Ala
            20                  25                  30
```

<210> SEQ ID NO 32
<211> LENGTH: 30
<212> TYPE: PRT
<213> ORGANISM: Artificial Sequence
<220> FEATURE:
<223> OTHER INFORMATION: Synthetic

<400> SEQUENCE: 32

```
Ala Ala Ala Ala Ala Ala Ala Ala Ala Ala Glu Glu Glu Glu Glu
1               5                   10                  15
Glu Glu Glu Glu Ala Ala Ala Ala Ala Ala Ala Ala Ala
            20                  25                  30
```

<210> SEQ ID NO 33
<211> LENGTH: 30
<212> TYPE: PRT
<213> ORGANISM: Artificial Sequence
<220> FEATURE:

<223> OTHER INFORMATION: Synthetic

<400> SEQUENCE: 33

Val Val Val Val Val Val Val Val Asp Asp Asp Asp Asp
1               5                   10                  15

Asp Asp Asp Asp Val Val Val Val Val Val Val Val
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Synthetic

<400> SEQUENCE: 34

Pro Pro Pro Pro Pro Pro Pro Pro Asp Asp Asp Asp Asp
1               5                   10                  15

Asp Asp Asp Asp Pro Pro Pro Pro Pro Pro Pro Pro
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Synthetic

<400> SEQUENCE: 35

Ala Ala Ala Ala Ala Ala Ala Ala Ala His His His His His
1               5                   10                  15

His His His His Ala Ala Ala Ala Ala Ala Ala Ala
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic

<400> SEQUENCE: 36

Ala Ala Ala Ala Ala Ala Ala Ala Ala Lys Lys Lys Lys Lys
1               5                   10                  15

Lys Lys Lys Lys Ala Ala Ala Ala Ala Ala Ala Ala
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic

<400> SEQUENCE: 37

Ala Ala Ala Ala Ala Ala Ala Ala Ala Arg Arg Arg Arg Arg
1               5                   10                  15

Arg Arg Arg Arg Ala Ala Ala Ala Ala Ala Ala Ala
            20                  25                  30

<210> SEQ ID NO 38
<211> LENGTH: 30
<212> TYPE: PRT
<213> ORGANISM: Artificial Sequence
<220> FEATURE:

<223> OTHER INFORMATION: Synthetic

<400> SEQUENCE: 38

Lys Lys Lys Lys Lys Lys Lys Lys Lys Ala Ala Ala Ala Ala Ala
1               5                   10                  15

Ala Ala Ala Ala Asp Asp Asp Asp Asp Asp Asp Asp Asp Asp Asp
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic

<400> SEQUENCE: 39

Lys Lys Lys Lys Lys Lys Lys Lys Lys Ala Ala Ala Ala Ala Ala
1               5                   10                  15

Ala Ala Ala Ala Glu Glu Glu Glu Glu Glu Glu Glu Glu Glu
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic

<400> SEQUENCE: 40

Arg Arg Arg Arg Arg Arg Arg Arg Arg Val Val Val Val Val Val
1               5                   10                  15

Val Val Val Val Asp Asp Asp Asp Asp Asp Asp Asp Asp Asp
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic

<400> SEQUENCE: 41

Lys Lys Lys Lys Lys Lys Lys Lys Lys Pro Pro Pro Pro Pro Pro
1               5                   10                  15

Pro Pro Pro Pro Asp Asp Asp Asp Asp Asp Asp Asp Asp Asp
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic

<400> SEQUENCE: 42

His His His His His His His His His Ala Ala Ala Ala Ala Ala
1               5                   10                  15

Ala Ala Ala Ala Glu Glu Glu Glu Glu Glu Glu Glu Glu Glu
            20                  25                  30

<210> SEQ ID NO 43
<211> LENGTH: 24
<212> TYPE: PRT
<213> ORGANISM: Artificial Sequence
<220> FEATURE:

```
<223> OTHER INFORMATION: Synthetic

<400> SEQUENCE: 43

Arg Ser Asn Thr Arg Met Thr Ala Arg Gln His Arg Ser Ala Asn His
1               5                   10                  15

Lys Ser Thr Gln Arg Ala Arg Ser
            20

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Gly Leu His Ile Pro Thr Ser His Arg
1               5

<210> SEQ ID NO 45
<211> LENGTH: 12
<212> TYPE: PRT
<213> ORGANISM: Artificial Sequence
<220> FEATURE:
<223> OTHER INFORMATION: Synthetic

<400> SEQUENCE: 45

Glu Ala His Val Met His Lys Val Ala Pro Arg Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46

Arg Ile Gly His Gly Arg Gln Ile Arg Lys Pro Leu
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Ala Ala Ala Ala Ala Ala Lys
1               5

<210> SEQ ID NO 48
<211> LENGTH: 31
<212> TYPE: DNA
<213> ORGANISM: Artificial Sequence
<220> FEATURE:
<223> OTHER INFORMATION: Synthetic

<400> SEQUENCE: 48
ccatggacgg aggccagcaa agcgagggca g                                    31

<210> SEQ ID NO 49
<211> LENGTH: 31
<212> TYPE: DNA
<213> ORGANISM: Artificial Sequence
<220> FEATURE:
```

<210> SEQ ID NO 49
<211> LENGTH: 31
<212> TYPE: DNA
<213> ORGANISM: Artificial Sequence
<220> FEATURE:
<223> OTHER INFORMATION: Synthetic

<400> SEQUENCE: 49
ctgccctcgc tttgctggcc tccgtccatg g                                31

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Thr Glu Thr Ser Gln Val Ala Pro Ala
 1               5

<210> SEQ ID NO 51
<211> LENGTH: 1000
<212> TYPE: DNA
<213> ORGANISM: Artificial Sequence
<220> FEATURE:
<223> OTHER INFORMATION: Synthetic

<400> SEQUENCE: 51
cctgaattcg ccgccaccat ggacggaggc aaccaaagcg agggcagcga gtttctgctg      60
ctgggcatgt ccgagagccc cgagcaacag cagatcctct tttggatgtt tctgagcatg     120
tatctggtca ccgtggtcgg aaatgtcctg attatcctcg ctattagctc cgacagcaga     180
ctccataccc ccgtctactt ctttctggct aacctctcct ttacagacct gttttcgctc     240
acaaacacca ttcccaaaat gctcgtcaac ctccaaagcc acaacaaagc tattagctat     300
gccggctgcc tcacacaact ctattttctc gtgagcctgg tggccctgga taatctgatt     360
ctcgccgtca tggcttacga tcggtacgtg gctatttgtt gccctctcca ctatacaaca     420
gctatgagcc ctaaactgtg catcctgctc ctgtccctgt gctgggtgct ctccgtgctg     480
tatggactca ttcacacact gctcatgaca agagtgacct tttgtggctc agaaagatc      540
cactacattt tctgcgaaat gtacgtcctc ctccggatgg cctgtagcaa cattcagatt     600
aaccataccg tgctgattgc taccggatgc tttattttcc tcatcccctt cggattcgtg     660
atcatcagct acgtcctcat tatcagagcc attctccgga tcccttccgt cagcaaaaaa     720
tataaggctt tcagcaccct gtgccagcca ctgggagccg tcagcctgtt ttatggaaca     780
ctgtgtatgg tctatctcaa acctctccac acctacagcg tcaaggactc cgtcgctaca     840
gtgatgtatg ccgtcgtcac ccccatgatg aacccccttca tctactccct cagaaacaaa     900
gatatgcatg cgctctcgg aagactcctg acaaacact ttaaaagact gaccggaggc      960
acagagacat cccaagtcgc tcctgcttaa gcggccgcga                          1000

<210> SEQ ID NO 52
<211> LENGTH: 323
<212> TYPE: PRT
<213> ORGANISM: Artificial Sequence
<220> FEATURE:
<223> OTHER INFORMATION: Synthetic

<400> SEQUENCE: 52

Met Asp Gly Gly Asn Gln Ser Glu Gly Ser Glu Phe Leu Leu Leu Gly
 1               5                  10                  15

Met Ser Glu Ser Pro Glu Gln Gln Gln Ile Leu Phe Trp Met Phe Leu
             20                  25                  30

Ser Met Tyr Leu Val Thr Val Val Gly Asn Val Leu Ile Ile Leu Ala

```
                    35                  40                  45
Ile Ser Ser Asp Ser Arg Leu His Thr Pro Val Tyr Phe Phe Leu Ala
 50                  55                  60

Asn Leu Ser Phe Thr Asp Leu Phe Phe Val Thr Asn Thr Ile Pro Lys
 65                  70                  75                  80

Met Leu Val Asn Leu Gln Ser His Asn Lys Ala Ile Ser Tyr Ala Gly
                     85                  90                  95

Cys Leu Thr Gln Leu Tyr Phe Leu Val Ser Leu Val Ala Leu Asp Asn
                100                 105                 110

Leu Ile Leu Ala Val Met Ala Tyr Asp Arg Tyr Val Ala Ile Cys Cys
            115                 120                 125

Pro Leu His Tyr Thr Thr Ala Met Ser Pro Lys Leu Cys Ile Leu Leu
        130                 135                 140

Leu Ser Leu Cys Trp Val Leu Ser Val Leu Tyr Gly Leu Ile His Thr
145                 150                 155                 160

Leu Leu Met Thr Arg Val Thr Phe Cys Gly Ser Arg Lys Ile His Tyr
                165                 170                 175

Ile Phe Cys Glu Met Tyr Val Leu Leu Arg Met Ala Cys Ser Asn Ile
            180                 185                 190

Gln Ile Asn His Thr Val Leu Ile Ala Thr Gly Cys Phe Ile Phe Leu
        195                 200                 205

Ile Pro Phe Gly Phe Val Ile Ser Tyr Val Leu Ile Ile Arg Ala
    210                 215                 220

Ile Leu Arg Ile Pro Ser Val Ser Lys Lys Tyr Lys Ala Phe Ser Thr
225                 230                 235                 240

Cys Ala Ser His Leu Gly Ala Val Ser Leu Phe Tyr Gly Thr Leu Cys
                245                 250                 255

Met Val Tyr Leu Lys Pro Leu His Thr Tyr Ser Val Lys Asp Ser Val
            260                 265                 270

Ala Thr Val Met Tyr Ala Val Val Thr Pro Met Met Asn Pro Phe Ile
        275                 280                 285

Tyr Ser Leu Arg Asn Lys Asp Met His Gly Ala Leu Gly Arg Leu Leu
    290                 295                 300

Asp Lys His Phe Lys Arg Leu Thr Gly Gly Thr Glu Thr Ser Gln Val
305                 310                 315                 320

Ala Pro Ala

<210> SEQ ID NO 53
<211> LENGTH: 9
<212> TYPE: DNA
<213> ORGANISM: Artificial Sequence
<220> FEATURE:
<223> OTHER INFORMATION: Synthetic

<400> SEQUENCE: 53 gccaccacc                                                            9

<210> SEQ ID NO 54
<211> LENGTH: 34
<212> TYPE: PRT
<213> ORGANISM: Artificial Sequence
<220> FEATURE:
<223> OTHER INFORMATION: Synthetic

<400> SEQUENCE: 54

Ser Leu Arg Asn Lys Asp Met His Gly Ala Leu Gly Arg Leu Leu Asp
 1               5                  10                  15
```

```
Lys His Phe Lys Arg Leu Thr Gly Gly Thr Glu Thr Ser Gln Val Ala
            20                  25                  30

Pro Ala

<210> SEQ ID NO 55
<211> LENGTH: 23
<212> TYPE: PRT
<213> ORGANISM: Artificial Sequence
<220> FEATURE:
<223> OTHER INFORMATION: Synthetic

<400> SEQUENCE: 55

Ile Leu Ala Val Met Ala Tyr Asp Arg Tyr Val Ala Ile Cys Cys Pro
1               5                   10                  15

Leu His Tyr Thr Thr Ala Met
            20

<210> SEQ ID NO 56
<211> LENGTH: 22
<212> TYPE: PRT
<213> ORGANISM: Artificial Sequence
<220> FEATURE:
<223> OTHER INFORMATION: Synthetic

<400> SEQUENCE: 56

Phe Phe Leu Ala Asn Leu Ser Phe Thr Asp Leu Phe Phe Val Thr Asn
1               5                   10                  15

Thr Ile Pro Lys Met Leu
            20

<210> SEQ ID NO 57
<211> LENGTH: 23
<212> TYPE: PRT
<213> ORGANISM: Artificial Sequence
<220> FEATURE:
<223> OTHER INFORMATION: Synthetic

<400> SEQUENCE: 57

Ser Val Lys Asp Ser Val Ala Thr Val Met Tyr Ala Val Val Thr Pro
1               5                   10                  15

Met Met Asn Pro Phe Ile Tyr
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic

<400> SEQUENCE: 58

Phe Phe Val Thr Asn Thr Ile Pro Lys Met Leu Val Asn Leu Gln Ser
1               5                   10                  15

His Asn Lys Ala Ile Ser Tyr
            20

<210> SEQ ID NO 59
<211> LENGTH: 21
<212> TYPE: PRT
<213> ORGANISM: Artificial Sequence
<220> FEATURE:
<223> OTHER INFORMATION: Synthetic

<400> SEQUENCE: 59

Tyr Val Ala Ile Cys Cys Pro Leu His Tyr Thr Thr Ala Met Ser Pro
```

```
                    1               5                  10                  15
Lys Leu Cys Ile Leu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic

<400> SEQUENCE: 60

Thr Gln Leu Tyr Phe Leu Val Ser Leu Val Ala Leu Asp Asn Leu Ile
  1               5                  10                  15

Leu Ala Val Met
            20

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

Ser Val Lys Asp Ser Val Ala Thr Val Met Tyr Ala Val Val Thr Pro
  1               5                  10                  15

Met

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Tyr Ala Val Val Thr Pro Met Met Asn Pro Phe Ile
  1               5                  10

<210> SEQ ID NO 63
<211> LENGTH: 12
<212> TYPE: PRT
<213> ORGANISM: Artificial Sequence
<220> FEATURE:
<223> OTHER INFORMATION: Synthetic

<400> SEQUENCE: 63

Val Asn Leu Gln Ser His Asn Lys Ala Ile Ser Tyr
  1               5                  10

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Phe Trp Met Phe Leu Ser Met Tyr Leu
  1               5

<210> SEQ ID NO 65
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 65

Ser Val Lys Asp Ser Val Ala Thr Val Met Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic

<400> SEQUENCE: 66

Phe Val Thr Asn Thr Ile Pro Lys Met Leu
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Tyr Ala Val Val Thr Pro Met Met Asn Pro
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Ser Val Lys Asp Ser Val Ala Thr Val Met
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Synthetic

<400> SEQUENCE: 69

Met Asp Gly Gly Asn Gln Ser Glu Gly Ser Glu Phe Leu Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic

<400> SEQUENCE: 70

Cys Gly Ser Arg Lys Ile His Tyr Ile Phe
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic
```

<400> SEQUENCE: 71

Arg Met Ala Cys Ser Asn Ile Gln Ile Asn His Thr Val Leu
 1               5                  10